US006992086B2

(12) United States Patent
Laborde et al.

(10) Patent No.: US 6,992,086 B2
(45) Date of Patent: Jan. 31, 2006

(54) ANTAGONISTS OF MCP-1 FUNCTION AND METHODS OF USE THEREOF

(75) Inventors: Edgardo Laborde, Foster City, CA (US); Louise Robinson, San Carlos, CA (US); Fanying Meng, San Francisco, CA (US); Brian T. Peterson, San Francisco, CA (US); Hugo O. Villar, La Jolla, CA (US); Steven E. Anuskiewicz, San Bruno, CA (US); Yoshiro Ishiwata, Aichi-gun (JP); Shoji Yokochi, Inabe-gun (JP); Yukiharu Matsumoto, Gifu (JP); Takuji Kakigami, Inabe-gun (JP); Hideaki Inagaki, Anjoh (JP); Takahito Jomori, Nagoya (JP); Kouji Matsushima, Matsudo (JP)

(73) Assignee: Telik, Inc., Palo Alto, CA (US)

( * ) Notice: Subject to any disclaimer, the term of this patent is extended or adjusted under 35 U.S.C. 154(b) by 0 days.

(21) Appl. No.: 10/716,363

(22) Filed: Nov. 17, 2003

(65) Prior Publication Data
US 2004/0077680 A1   Apr. 22, 2004

Related U.S. Application Data

(62) Division of application No. 10/060,967, filed on Jan. 29, 2002, now Pat. No. 6,670,364.

(60) Provisional application No. 60/265,841, filed on Jan. 31, 2001.

(51) Int. Cl.
*A61K 31/496* (2006.01)
*A61K 31/437* (2006.01)
*C07D 498/04* (2006.01)
*C07D 471/04* (2006.01)
*A61P 37/00* (2006.01)

(52) U.S. Cl. .............. 514/253.04; 514/302; 514/234.2; 514/303; 514/252.11; 514/218; 540/575; 544/127; 544/362; 544/121; 544/357; 546/115; 546/120

(58) Field of Classification Search ................ 546/115; 544/127, 362; 514/302, 234.2, 253.04
See application file for complete search history.

(56) References Cited

U.S. PATENT DOCUMENTS

| 3,823,144 | A |   | 7/1974 | Schmitt et al. ............. 544/377 |
| 4,269,990 | A |   | 5/1981 | May et al. .................. 548/315 |
| 5,977,108 | A |   | 11/1999 | Kikuchi et al. ............. 514/249 |
| 6,140,338 | A |   | 10/2000 | Naya et al. ................. 514/299 |
| 6,228,869 | B1 | * | 5/2001 | Levin et al. ................ 514/310 |
| 6,288,103 | B1 |   | 9/2001 | Faull et al. ................. 514/419 |
| 6,316,449 | B1 |   | 11/2001 | Bratton et al. ......... 514/252.04 |
| 6,329,402 | B1 |   | 12/2001 | Kikuchi et al. ............. 514/341 |
| 6,342,516 | B1 |   | 1/2002 | Umeda et al. .............. 514/397 |

FOREIGN PATENT DOCUMENTS

| FR | 2 001 284 | 9/1969 |
| GB | 1 250 611 | 10/1974 |
| JP | 9-255572 | 9/1997 |
| WO | 92/14710 | 9/1992 |
| WO | 97/24325 | 7/1997 |
| WO | 97/44329 | 11/1997 |
| WO | 98/02151 | 1/1998 |
| WO | 98/06703 | 2/1998 |
| WO | 98/27815 | 7/1998 |
| WO | 98/04554 | 5/1999 |
| WO | 99/40072 | 8/1999 |
| WO | 00/46198 | 8/2000 |
| WO | WO 01/36403 A1 | 5/2001 |
| WO | 01/57003 | 8/2001 |
| WO | 01/57021 | 8/2001 |
| WO | 01/57044 | 8/2001 |
| WO | WO 02/060900 A2 | 8/2002 |

OTHER PUBLICATIONS

Alam et al., "Increased MCP-1, RANTES, and MIP-1α in Bronchoalveolar Lavage Fluid of Allergic Asthmatic Patients", *Am J Respir Crit Care Med*, 153:1398-1404. (1996).

Alcami et al., "Blockade of Chemokine Activity by a Soluble Chemokine Binding Protein form Vaccinia Virus", *J Immunol*, 160:624-633 (1998).

Antoniades et al., "Expression of monocyte chemoattractant protein 1 mRNA in human idiopathic pulmonary fibrosis", *Proc Natl Acad Sci USA*, 89:5371-5375 (1992).

Ajuebor et al., "Endogenous monocyte chemoattractant protein-1 recruits monocytes in the zymosan peritonitis model", *Journal of Leukocyte Biology*, vol. 63:108-116, Jan. 1998.

Baggiolini et al., "Human Chemokines; an update", Annu rev Immunol (1997), pp. 15:675-705.

(Continued)

*Primary Examiner*—Evelyn Mei Huang
(74) *Attorney, Agent, or Firm*—Foley & Lardner LLP

(57) ABSTRACT

The present invention relates to chemical compounds, pharmaceutical compositions comprising said compounds, uses of said compounds and compositions, methods of treatment employing said compounds and compositions, and processes for preparing said compounds. Specifically, this invention relates to novel compounds which are antagonists of MCP-1 function and are useful in the prevention or treatment of chronic or acute inflammatory or autoimmune diseases, especially those associated with aberrant lymphocyte or monocyte accumulation such as arthritis, asthma, atherosclerosis, diabetic nephropathy, inflammatory bowel disease, Crohn's disease, multiple sclerosis, nephritis, pancreatitis, pulmonary fibrosis, psoriasis, restenosis, and transplant rejection. More specifically, the invention is related to pharmaceutical compositions comprising these compounds and the use of these compounds and compositions in the prevention or treatment of such diseases.

26 Claims, No Drawings

OTHER PUBLICATIONS

Baggiolini, Chemokines and Leukocyte Traffic, Nature vol.: 392:9 pp 565-568, (1998).

Boring et al., "Decreased lesion formation in CCR2$^{-/-}$ mice reveals a role for chemokines in the initiation of atherosclerosis", *Nature*, 394:894-897 (1998).

Bright et al., "Identification of a Non Peptidic Rantes Antagonist", *Bioorg Med Chem Lett*, 8:771-774 (1998).

Campbell et al., "Monocyte Chemoattractant Protein-1 Mediates Cockroach Allergen-Induced Bronchial Hyperreactivity in Normal but Not CCR2$^{-/-}$ Mice: The Role of Mast Cells", *J Immunol*, 163:2160-2167 (1999).

Chemical Abstracts, 103(17), Abst. No. 141873u (1985); Abstract of Kuxzinski, L. et al.: "Synthesis of new 4 and 5 disubstituted isothizoles " Pol J Pharmacol Pahrm, 36(5): 485-491 (1984).

Chemical Abstracts, 100(21), Abst. No. 174751u (1984): Abstract of Ormek, G. et al., "Ring-opening reactions of potentially biologically active benzothienooxazines" Arc Pharm, 317(2):117-120 (1984).

Folkman and Shing, "Control of Angiogensis by Heparin and Other Sulfated Polysaccharides", *Adv Exp Med Biol.*, 313:355-364 (1992).

Forbes et al., "CCR2B Receptor Antagonists: Conversion of a Week HTS Hit to a Potent Lead Compound";*Bioorg Med Chem. Lett*, 10:1803-1806 (2000).

Gosling et al., "MCP-1 deficiency reduces susceptibility to atherosclerosis in mice that over express human apo37lipoprotein B", *J Clin Invest*, 103:773-778 (1999).

Gu et al., "Absence of Monocyte Chemoattractant Protein-1 Reduces Atherosclerosis in Low Density Lipoprotein Receptor-Deficient Mice", *Mol Cell*, 2:275-281 (1998).

Hesselgesser, "Identification and Characterization of Small Molecule Functional Antagonists of the CCR1 Chemokine Receptor", *J. Biol Chem*, 273:15687-15692 (1998).

Hoogewerf et al., "Glycosaminoglycans Mediate Cell Surface Oligomerization of Chemokines", Biochemistry 36: 13570-13578, (1997).

Hosaka et al., "Expression of the Chemokine Superfamily in Rheumatoid Arthritis", *Clin Exp Immunol*, 97:451-457. (1994).

Hsieh et al., "Immunotherapy Suppresses the Production of monocyte chemotatic and activating factor and augments the production of IL-8 in Children with Asthma", *J Allery Clin Immunol*, 98:580-587 (1996).

Kitano M. et al., "Synthesis and Biological Activity of N-(Aminoiminomethly)-1H-Idoleca Rboxamide Inhibitors", Chem and Pharm Bulletin, Pharmaceutical Society of Japan, vol. 47, No. 11, Nov. 1999, pp 1538.

Koch et al., "Enhanced Production of Monocyte Chemoattractant Protein-1 in Rheumatoid Arthritis", *J Clin Invest*, 90:772-779, (1992).

Kunkel et al., "The Role of Chemokines in Inflammatory Joint Disease", *J Leukocyte Biol*, 59:6-12 (1996).

Kurashima et al., "Increase of Chemokine Levels in Sputum Precedes Exacerbation of Acute Asthma Attacks", *J Leukocyte Biol*, 59:313-316, (1996).

Kuschert et al., "Glycosamineoglycans interact selectively with chemokines and moldulate receptor binding and cellular responses", *Biochemistry* 38:12959-12968, (1999).

Liang et al., "Identification and characterization of a potent, selective and orally active antagonist of the cc chemokine receptor-1", *The Journal of Biological Chemistry*, vol. 25: 19000-19008, Jun. 23, 2000.

Luster, "Chemokines_Chemotactic Cytokines That Mediate Inflammation", *The New England Journal of Medicine*, pp. 436-445, Feb. 12, 1998.

McFadden and Kelvin, "New Strategies for Chemokine Inhibition and Modulation", *Biochem Pharmacol*, 54:1271-1280 (1997).

Mirzadegan et al., "Identification of the binding site for a novel class of CCR2bcemokine receptor antagonists . . . ", The American Society for Biochemistry and Molecular Biology, Inc., manuscript M000692200, (2000).

Moore et al., "Tumor angiogenesis is regulated by CXC chemokines", *J Lab Clin Med*, 132:97-103 (1998).

Moore et al., "CXC Chemokine Modulation of angiogenesis . . . ", J Investigative Medicine, vol. 46:113-120 (1998).

Murphy, : The Molecular Biology of Leukocyte Chemoattractant Receptors, *Annu Rev Immun*, 12:593-633, (1994).

Nelken et al., "Monocyte Chemoattractant Protein-1 in Human Atheromatous Plaques"; *J. Clin Invest*, 88:1121-1127 (1991).

Okada et al., "Synthesis and Antitumor Activities of Water-Soluble Benzoylphenylureas", *Chem Pharm Bull*, 47:430-433, (1999).

Okada et al., "Synthesis and Antitumor Activities of Prodrugs of Benzoylphenylureas", *Chem Pharm Bull* 42:57-61, (1994).

Okada et al., "Synthesis and Antitumor Activities of Novel Benzoylphenylurea Derivatives", *Chem Pharm Bull*, 39: 2308-2315 (1991).

Proost et al., "The Role of Chemokines in Inflammation", *Int J Clin Lab Res*, 26:211-223, (1996).

Robinson et al., "Chemokine expression in Rheumatoid Arthritis . . . ", *Clin Exp Innumol* 101:398-407 (1995).

Rollins, "Chemokines", *Blood*, vol. 90 No. 3, pp. 909-928, Aug. 1, 1997.

Rousseau, Jean-Francois et al., Chemical Abstract, "Regioselective ortho-directed metalation and electrophilic substitution of indoleand indoling -5-(N-phenyl) carboxamides" retrieved from STN database accession No. 136:355126 XP002206081 abstract & Heterocycles 92001), 55(12), 2289-2304.

Rovin et al., "Chemotatic Factors and Renal Inflammation", *American Journal of Kidney Diseases*, 31:1065-1084, Jun. 1998.

Rovin, "Chemokines as Therapeutic Targets in Renal Inflammation", American Journal of Kidney Diseases, 34: 761-767, Oct. 1999.

Rovin, "Chemokine blokade as a therapy for renal disease", *Current Opinion in Nephrology and Hypertension*, 13:225-232, (2000).

Rovin et al., "A Novel Polymorphism in the MCP-1 Gene Regulatory Region That Influences MCP-1 Expression", *Biochemical and Biophysical Research Communications*, 259, pp. 344-348, (1999).

Saunders and Tarby, "Opportunities for novel therapeutic agents acting at chemokine receptors", Drug Discovery Today, vol. 4 No. 2 (1999).

Schall, "Biology of the RANTES/SIS Cytokine Family", *Cytokine*, 3:165-183, (1991).

Sendo et al., "Regulation of leukocyte adherence and migration by glycosylphosphatidyl-inositol-anchored proteins", *Journal of Leukocyte Biology*, vol. 66, pp. 369-374, Sep. 1999.

Servant et al., "Polarization of Chemoattract Receptor Signaling During Neutrophil Chemotaxis", *Science*, vol. 287: 1037-1040, Feb. 11, 2000.

Strieter et al., "The Immunopathology of Chemotactic Cytokines: The Role of Interleukin-8 and Monocyte Chemoattractant Protein-1", *J Lab Clin Med*, 123:183-197 (1994).

Sugiyama et al., "Chemokines in Brochoalveolar Lavage Fluid in Summer-type Hypersensitivity Pneumonitis", *Eur Respir J*, 8:1084-1090 (1995).

Szekanecz et al., "Cytokines in Rheumatoid Arthritis", *Drugs and Aging*, 12:377-390, May 12, 1998.

Taub, D.D. "Chemokine-Leukocyte Interactions", *Cytokine Growth Factor Rev*, 7:355-376, (1996).

Takeya et al., "Detection of Monocyte Chemoattractant Protein-1 in Human Atherosclerotic Lesions by an Anti-monocyte Chemoattractant Protein-1 Monoclonal Antibody", *Human Pathol*, 24:534-539 (1993).

Tanaka et al., "T-cell adhesion induced by proteoglycan-immobilzed cytokine MIP-1β", *Nature*, 361:79-82 (1993).

Trivedi et al., "Chemokines: Targets for novel therapeutics", *Annual Reports in Medicinal Chemistry*, 35:191-200, (2000).

Vaddi and Newton, "Comparison of biological responses of human monocytes and THP-1 cells to chemokines of the intercrine-β family", *Journal of Leukocyte Biology*, vol. 55: 756-761, Jun. 1994.

Villiger et al., "Production of Monocyte Chemoattractant Protein-1 By Inflamed Synovial Tissue and Cultered Synoviocytes", *J Immunol*, vol. 149, pp. 722-727, (1992).

Vlodavsky et al., "Involvement of heparan sulfate and related molecules in sequestration and growth promoting activity of fibroblast growth factor", *Cancer and Mtastasis Reviews* 15: 177-186, (1996).

Waltenberger et al., "Suramin is a Potent Inhibitor of Vascular Endothelial Growth Factor. A Contribution to the Molecular Basis of its Antiangiogenic Action", *J Mol Cell Cardiol*, 28:1523-1529, (1996).

Wang et al, "Chemokines and their role in tumor growth and metastasis", *Journal of Immunological Methods*, 220: 1-17, (1998).

Wellstein and Czubayko, "Inhibition of fibroblast growth factors", *Breast Cancer Res Treat*, 38:109-119 (1996).

White, "Identification of a Potent, Selective Non-peptide CXCR2 Antagonist That Inhibits Interleukin-8-induced Neutrophil Migration", *J. Bio Chem*, 273:10095-10098 (1998).

Wrenshall et al., "Modulation of macrophage and B cell funtion by glycosaminoglycans", Journal of Leukocyte Biology, vol. 66:391-400, Sep. 1999.

Yang et al., "Fully human anti-interleukin-8 monoclonal antibodies: potential therapeutics for the treatment of inflammatory disease states", Journal of Leukocyte Biology, vol. 66: 401-410, Sep. 1999.

Yla-Herttuala et al., "Expression of Monocyte Chemoattractant Protein 1 in Macrophage-Rich Areas of Human and Rabbit Atheroslerotic Lesions", *Proc Natl Acad Sci USA*, 88:5252-5256 (1991).

Zetzsche et al., Crossfire Beilstein 'Online' Beilstein Institut Aur Forerderung Der Wissenschaten, Frankfurt, DE; Abstract, Chemische Berichte, vol. 72, 1939, p. 1599.

* cited by examiner

ANTAGONISTS OF MCP-1 FUNCTION AND METHODS OF USE THEREOF

CROSS-REFERENCE TO RELATED APPLICATIONS

This application is a divisional of U.S. application Ser. No. 10/060,967, filed 29 Jan. 2002 now U.S. Pat. No. 6,670,364, which claims the benefit under 35 USC 119(e) of U.S. Provisional Application No. 60/265,841, filed 31 Jan. 2001. The entire contents of those applications are incorporated by reference.

FIELD OF THE INVENTION

This invention relates to chemical compounds that are antagonists of MCP-1 function and are useful in the prevention or treatment of chronic or acute inflammatory or autoimmune diseases, especially those associated with aberrant lymphocyte or monocyte accumulation such as arthritis, asthma, atherosclerosis, diabetic nephropathy, inflammatory bowel disease, Crohn's disease, multiple sclerosis, nephritis, pancreatitis, pulmonary fibrosis, psoriasis, restenosis, and transplant rejection, to pharmaceutical compositions comprising these compounds, to uses of these compounds and compositions especially in the prevention or treatment of such diseases, to methods of treatment employing these compounds and compositions, and to processes for preparing these compounds.

BACKGROUND OF THE INVENTION

Chemokines: Structure and Function

The migration of leukocytes from blood vessels into diseased tissues is an important process in the initiation of normal inflammatory responses to certain stimuli or insults to the immune system. However, this process is also involved in the onset and progression of life-threatening inflammatory and autoimmune diseases; blocking leukocyte recruitment in these disease states, therefore, can be an effective therapeutic strategy.

The mechanism by which leukocytes leave the bloodstream and accumulate at inflammatory sites involves three distinct steps: (1) rolling, (2) arrest and firm adhesion, and (3) transendothelial migration [Springer, Nature 346:425–433 (1990); Lawrence and Springer, Cell 65:859–873 (1991); Butcher, Cell 67:1033–1036 (1991)]. The second step is mediated at the molecular level by chemoattractant receptors on the surface of leukocytes which bind chemoattractant cytokines secreted by proinflammatory cells at the site of damage or infection. Receptor binding activates leukocytes, increases their adhesiveness to the endothelium, and promotes their transmigration into the affected tissue, where they can secrete inflammatory and chemoattractant cytokines and degradative proteases that act on the subendothelial matrix, facilitating the migration of additional leukocytes to the site of injury.

The chemoattractant cytokines, collectively known as "chemokines," are a large family of low molecular weight (8 to 10 kD) proteins that share the ability to stimulate directed cell migration ("chemotaxis") [Schall, Cytokine 3:165–183 (1991); Murphy, Rev Immun 12:593–633 (1994)].

Chemokines are characterized by the presence of four conserved cysteine residues and are grouped into two main subfamilies based on whether the two amino-terminal cysteines are separated by one amino acid (CXC subfamily, also known as α-chemokines) or immediately adjacent to each other (CC subfamily, also referred to as β-chemokines) [Baggiolini et al., Adv Immunol 55:97–179 (1994); Baggiolini et al., Annu Rev Immunol 15:675–705 (1997); Deng et al., Nature 381:661–666 (1996); Luster, New Engl J Med 338:436445 (1998); Saunders and Tarby, Drug Discovery Today 4:80–92 (1999)].

The chemokines of the CXC subfamily, represented by IL-8, are produced by a wide range of cells and act predominantly on neutrophils as mediators of acute inflammation. The CC chemokines, which include MCP-1, RANTES, MIP-1α, and MIP-1β, are also produced by a variety of cells, but these molecules act mainly on monocytes and lymphocytes in chronic inflammation.

Like many cytokines and growth factors, chemokines utilize both high and low affinity interactions to elicit full biological activity. Studies performed with labeled ligands have identified chemokine binding sites ("receptors") on the surface of neutrophils, monocytes, T cells, and eosinophils with affinities in the 500 pM to 10 nM range [Kelvin et al., J Leukoc Biol 54:604–612 (1993); Murphy, Annu Rev Immunol 12:593–633 (1994); Raport et al., J Leukoc Biol 59:18–23 (1996); Premack and Schall, Nature Med 2:1174–1178 (1996)]. The cloning of these receptors has revealed that cell surface high-affinity chemokine receptors belong to the seven transmembrane ("serpentine") G-protein-coupled receptor (GPCR) superfamily.

Chemokine receptors are expressed on different cell types, including non-leukocyte cells. Some receptors are restricted to certain cells (e.g., the CXCR1 receptor is predominantly restricted to neutrophils), whereas others are more widely expressed (e.g., the CCR2 receptor is expressed on monocytes, T cells, natural killer cells, dendritic cells, and basophils).

Given that at least twice as many chemokines have been reported to date as there are receptors, there is a high degree of redundancy in the ligands and, not surprisingly, most chemokine receptors are rather promiscuous with regard to their binding partners. For example, both MIP-1α and RANTES bind to the CCR1 and CCR4 receptors, while MCP-1 binds to the CCR2 and CCR4 receptors. Although most chemokines receptors bind more than one chemokine, CC receptors bind only CC chemokines, and CXC receptors bind only CXC chemokines. This ligand-receptor restriction may be related to the structural differences between CC and CXC chemokines, which have similar primary, secondary, and tertiary structures, but different quaternary structures [Lodi et al., Science 263:1762–1767 (1994)].

The binding of chemokines to their serpentine receptors is transduced into a variety of biochemical and physiological changes, including inhibition of cAMP synthesis, stimulation of cytosolic calcium influx, upregulation or activation of adhesion proteins, receptor desensitization and internalization, and cytoskeletal rearrangements leading to chemotaxis [Vaddi et al., J Immunol 153:4721–4732 (1994); Szabo et al., Eur J Immunol 27:1061–1068 (1997); Campbell et al., Science 279:381–384 (1998); Aragay et al., Proc Natl Acad Sci USA 95:2985–2990 (1998); Franci et al., J Immunol 157:5606–5612 (1996); Aramori et al., EMBO J 16:4606–4616 (1997); Haribabu et al., J Biol Chem 272: 28726–28731 (1997); Newton et al., Methods Enzymol 287:174–186 (1997)]. In the case of macrophages and neutrophils, chemokine binding also triggers cellular activation, resulting in lysozomal enzyme release and generation of toxic products from the respiratory burst [Newton et al., Methods Enzymol 287:174–186 (1997); Zachariae et al., J Exp Med 171:2177–2182 (1990); Vaddi et al., J Leukocyte Biol 55:756–762 (1994)]. The molecular details of the chemokine-receptor interactions responsible for inducing signal transduction, as well as the specific pathways that link binding to the above-mentioned physiological changes, are still being elucidated. Notwithstanding the complexity of these events, it has been shown that in the case of the MCP-1/CCR2 interaction, specific molecular features of MCP-1 can induce different conformations in CCR2 that are coupled to separate post-receptor pathways [Jarnagin et al., *Biochemistry* 38:16167–16177 (1999)]. Thus, it should be possible to identify ligands that inhibit chemotaxis without affecting other signaling events.

In addition to their high-affinity seven transmembrane GPCRs, chemokines of both subfamilies bind to various extracellular matrix proteins such as the glycosaminoglycans (GAGs) heparin, chondroitin sulfate, heparan sulfate, and dermatan sulfate with affinities in the middle nanomolar to millimolar range. These low-affinity chemokine-GAG interactions are believed to be critical not only for conformational activation of the ligands and presentation to their high-affinity serpentine receptors, but also for the induction of stable chemokine gradients that may function to stimulate haptotaxis (i.e., the migration of specific cell subtypes in response to a ligand gradient that is affixed upon the surface of endothelial cells or embedded within the extracellular matrix) [Witt and Lander, *Curr Biol* 4:394–400 (1994); Rot, *Eur J Immunol* 23:303–306 (1993); Webb et al., *Proc Natl Acad Sci USA* 90:7158–7162 (1993); Tanaka et al, *Nature* 361:79–82 (1993); Gilat et al., *J Immunol* 153:4899–4906 (1994)]. Similar ligand-GAG interactions have been described for a variety of cytokines and growth factors, including the various members of the FGF family, hepatocyte growth factor, IL-3 and IL-7, GM-CSF, and VEGF [Roberts et al., *Nature* 332:376–378 (1988); Gilat et al., *Immunol Today* 17:16–20 (1996); Clarke et al., *Cytokine* 7:325–330 (1995); Miao et al., *J Biol Chem* 271:4879–4886 (1996); Vlodavsky et al., *Cancer Metastasis Rev* 15:177–186 (1996)].

MCP-1 and Diseases

Chemokines have been implicated as important mediators of allergic, inflammatory and autoimmune disorders and diseases, such as asthma, atherosclerosis, glomerulonephritis, pancreatitis, restenosis, rheumatoid arthritis, diabetic nephropathy, pulmonary fibrosis, and transplant rejection. Accordingly, it has been postulated that the use of antagonists of chemokine function may help reverse or halt the progression of these disorders and diseases.

In particular, elevated expression of MCP-1 has been observed in a number of chronic inflammatory diseases [Proost et al., *Int J Clin Lab Res* 26:211–223 (1996); Taub, D. D. *Cytokine Growth Factor Rev* 7:355–376 (1996)] including rheumatoid arthritis [Robinson et al., *Clin Exp Immunol* 101:398–407 (1995); Hosaka et al., ibid. 97:451–457 (1994); Koch et al., *J Clin Invest* 90:772–779 (1992); Villiger et al., *J Immunol* 149:722–727 (1992)], asthma [Hsieh et al., *J Allergy Clin Immunol* 98:580–587 (1996); Alam et al., *Am J Respir Crit Care Med* 153: 1398–1404 (1996); Kurashima et al., *J Leukocyte Biol* 59:313–316 (1996); Sugiyama et al., *Eur Respir J* 8:1084–1090 (1995)], and atherosclerosis [Yla-Herttuala et al., *Proc Natl Acad Sci USA* 88:5252–5256 (1991); Nelken et al., *J Clin Invest* 88:1121–1127 (1991)].

MCP-1 appears to play a significant role during the early stages of allergic responses because of its ability to induce mast cell activation and LTC4 release into the airway, which directly induces AHR (airways hyper-responsiveness) [Campbell et al., *J Immunol* 163:2160–2167 (1999)].

MCP-1 has been found in the lungs of patients with idiopathic pulmonary fibrosis and is thought to be responsible for the influx of mononuclear phagocytes and the production of growth factors that stimulate mesenchymal cells and subsequent fibrosis [Antoniades et al., *Proc Natl Acad Sci USA* 89:5371–5375 (1992)]. In addition, MCP-1 is also involved in the accumulation of monocytes in pleural effusions which is associated with both *Mycobacterium tuberculosis* infection and malignancy [Strieter et al., *J Lab Clin Med* 123:183–197 (1994)].

MCP-1 has also been shown to be constitutively expressed by synovial fibroblasts from rheumatoid arthritis patients, and its levels are higher in rheumatoid arthritis joints compared to normal joints or those from other arthritic diseases [Koch et al., *J Clin Invest* 90:772–779 (1992)]. These elevated levels of MCP-1 are probably responsible for the monocyte infiltration into the synovial tissue. Increased levels of synovial MIP-1α and RANTES have also been detected in patients with rheumatoid arthritis [Kundel et al., *J Leukocyte Biol* 59:6–12 (1996)].

MCP-1 also plays a critical role in the initiation and development of atherosclerotic lesions. MCP-1 is responsible for the recruitment of monocytes into atherosclerotic areas, as shown by immunohistochemistry of macrophage-rich arterial wall [Yla-Herttuala et al., *Proc Natl Acad Sci USA* 88:5252–5256 (1991); Nelken et al., *J Clin Invest* 88:1121–1127 (1991)] and anti-MCP-1 antibody detection [Takeya et al., *Human Pathol* 24:534–539 (1993)]. LDL-receptor/MCP-1-deficient and apoB-transgenic/MCP-1-deficient mice show significantly less lipid deposition and macrophage accumulation throughout their aortas compared with wild-type MCP-1 strains [Alcami et al., *J Immunol* 160:624–633 (1998); Gosling et al., *J Clin Invest* 103: 773–778 (1999); Gu et al., *Mol. Cell.* 2:275–281 (1998); Boring et al., *Nature* 394:894–897 (1998).

Other inflammatory diseases marked by specific site elevations of MCP-1 include multiple sclerosis (MS), glomerulonephritis, and stroke.

These findings suggest that the discovery of compounds that block MCP-1 activity would be beneficial in treating inflammatory diseases.

Antagonists of Chemokine Function

Most chemokine antagonists reported to date are either neutralizing antibodies to specific chemokines or receptor-ligand antagonists, that is, agents that compete with specific chemokines for binding to their cognate serpentine receptors but, unlike the chemokines themselves, do not activate these receptors towards eliciting a functional response [Howard et al., *Trend Biotechnol* 14:46–51 (1996)].

The use of specific anti-chemokine antibodies has been shown to curtail inflammation in a number of animal models (e.g., anti-MIP-1α in bleomycin-induced pulmonary fibrosis [Smith et al., *Leukocyte Biol* 57:782–787 (1994)]; anti-IL-8 in reperfusion injury [Sekido et al., *Nature* 365:654–657 (1995)], and anti-MCP-1 in a rat model of glomerulonephritis [Wada et al., *FASEB J* 10:1418–1425 (1996)]. In the MRL-lpr mouse arthritis model, administration of an MCP-1 antagonist significantly reduced the overall histopathological score after the early onset of the disease [Gong et al., *J Exp Med* 186:131–137 (1997)].

A major problem associated with using antibodies to antagonize chemokine function is that they must be humanized before use in chronic human diseases. Furthermore, the ability of multiple chemokines to bind and activate a single receptor forces the development of a multiple antibody strategy or the use of cross-reactive antibodies in order to completely block or prevent pathological conditions.

Several small molecule antagonists of chemokine receptor function have been reported in the scientific and patent literature [White, *J. Biol Chem* 273:10095–10098 (1998); Hesselgesser, *J. Biol Chem* 273:15687–15692 (1998); Bright et al., *Bioorg Med Chem Lett* 8:771–774 (1998); Lapierre, *26th Natl Med Chem Symposium*, June 14–18, Richmond (Va.), USA (1998); Forbes et al., *Bioorg Med Chem Lett* 10:1803–18064 (2000); Kato et al., WO Patent 97/24325; Shiota et al., WO Patent 97/44329; Naya et al., WO Patent 98/04554; Takeda Industries, JP Patent 0955572 (1998); Schwender et al., WO Patent 98/02151; Hagmann et al., WO Patent 98/27815; Connor et al., WO Patent 98/06703; Wellington et al., U.S. Pat No. 6,288,103 B1 (2001)].

The specificity of the chemokine receptor antagonists, however, suggests that inflammatory disorders characterized by multiple or redundant chemokine expression profiles will be relatively more refractory to treatment by these agents. A different approach to target chemokine function would involve the use of compounds that disrupt the chemokine-GAG interaction. One class of such agents with potential therapeutic application would consist of small organic molecules that bind to the chemokine low affinity GAG-binding domain.

Compounds of this class might not inhibit binding of the chemokine to its high-affinity receptor per se, but would disrupt chemokine localization within the extracellular matrix and provide an effective block for directed leukocyte-taxis within tissues. An advantage of this strategy is the fact that most CC and CXC chemokines possess similar C-terminal protein folding domains that define the GAG-binding site, and, hence, such compounds would be more useful for the treatment of inflammatory disorders induced by multiple, functionally redundant chemokines [McFadden and Kelvin, *Biochem Pharmacol* 54:1271–1280 (1997)].

The use of small molecule drugs to bind cytokine ligands and disrupt interactions with extracellular GAGs has been reported with FGF-dependent angiogenesis [Folkman and Shing, *Adv Exp Med Biol* 313:355–364 (1992)]. For example, the heparinoids suramin and pentosan polysulphate both inhibit angiogenesis under conditions where heparin is either ineffective or even stimulatory [Wellstein and Czubayko, *Breast Cancer Res Treat* 38:109–119 (1996)]. In the case of suramin, the anti-angiogenic capacity of the drug has also been shown to be targeted against VEGF [Waltenberger et al., *J Mol Cell Cardiol* 28:1523–1529 (1996)] which, like FGF, possesses heparin-binding domains similar to those of the chemokines. Heparin or heparin sulphate has also been shown to directly compete for GAG interactions critical for T-cell adhesion mediated by MIP-1β in vitro [Tanaka et al., *Nature* 361:79–82 (1993)].

The entire disclosure of all documents cited throughout this application are incorporated hrein by reference.

SUMMARY OF THE INVENTION

The present invention relates to compounds that inhibit MCP-1-induced chemotaxis of human monocytic cells both in vitro and in vivo. These novel MCP-1 antagonists are useful for the treatment of inflammatory diseases, especially those associated with lymphocyte and/or monocyte accumulation, such as atherosclerosis, diabetic nephropathy, inflammatory bowel disease, Crohn's disease, multiple sclerosis, nephritis, pancreatitis, pulmonary fibrosis, psoriasis, restenosis, rheumatoid arthritis, and other chronic or acute autoimmune disorders. In addition, these compounds can be used in the treatment of allergic hypersensitivity disorders, such as asthma and allergic rhinitis, characterized by basophil activation and eosinophil recruitment.

A first embodiment of the present invention provides compounds of Formula (I) and Formula (II):

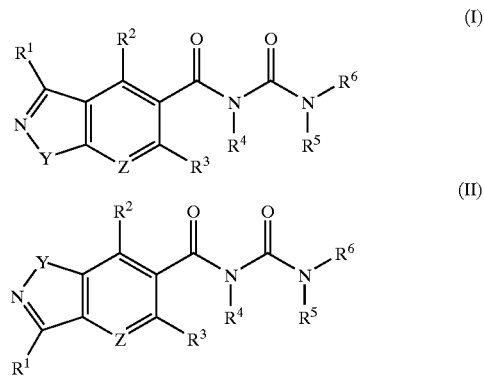

where:
Y is O, S or N—$R^7$,
Z is N or C—$R^8$,
$R^1$, $R^2$, $R^3$, and $R^8$ are independently, hydrogen, or optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), halo(lower alkyl), —$CF_3$, halogen, nitro, —CN, —$OR^9$, —$SR^9$, —$NR^9R^{10}$, —$NR^9$(carboxy(lower alkyl)), —C(=O)$R^9$, —C(=O)$OR^9$, —C(=O)$NR^9R^{10}$, —OC(=O)$R^9$, —$SO_2R^9$, —$OSO_2R^9$, —$SO_2NR^9R^{10}$, —$NR^9SO_2R^{10}$ or —$NR^9C$(=O)$R^{10}$, where $R^9$ and $R^{10}$ are independently, hydrogen, optionally substituted lower alkyl, lower alkyl-N($C_{1-2}$ alkyl)$_2$, lower alkyl(optionally substituted heterocycloalkyl), alkenyl, alkynyl, optionally substituted cycloalkyl, cycloalkyl(lower alkyl), optionally substituted heterocycloalkyl(lower alkyl), aryl(lower alkyl), optionally substituted aryl, optionally substituted aryloxy, heteroaryl, heteroaryl(lower alkyl), or $R^9$ and $R^{10}$ together are —($CH_2$)$_{4-6}$— optionally interrupted by one O, S, N, NH, N-(alkyl) N-(aryl(lower aryl)), N-(carboxy(lower alkyl)) or N-(optionally substituted $C_{1-2}$ alkyl) group, $R^7$ is hydrogen, optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), —C(=O)$R^9$, —C(=O)$OR^9$, —C(=O)$NR^9R^{10}$, —$SO_2R^9$, or —$SO_2NR^9R^{10}$, where $R^9$ and $R^{10}$ are independently, hydrogen, optionally substituted lower alkyl, lower alkyl-N($C_{1-2}$ alkyl)$_2$, lower alkyl(optionally substituted heterocycloalkyl), alkenyl, alkyl, optionally substituted cycloalkyl, cycloalkyl(lower alkyl), optionally substituted heterocycloalkyl(lower alkyl), aryl(lower alkyl), optionally substituted aryl, optionally substituted aryloxy, heteroaryl, heteroaryl(lower alkyl), or $R^9$ and $R^{10}$ together are —($CH_2$)$_{4-6}$— optionally interrupted by one O, S, NH, N-(aryl), N-(aryl(lower alkyl)), N-(carboxy(lower alkyl)) or N-(optionally substituted $C_{1-2}$ alkyl) group, $R^4$ and $R^5$ are independently, hydrogen, lower alkyl optionally substituted lower alkyl, optionally substituted aryl, or optionally substituted aryl(lower alkyl), or, together, are —$(CH_2)_{2-4}$—, $R^6$ is hydrogen, optionally substituted lower alkyl, alkenyl, alkynyl, cycloalkyl, cycloalkyl(lower alkyl), optionally substituted heterocycloalkyl, optionally substituted aryl, optionally substituted aryl(lower alkyl), optionally substituted heteroaryl, optionally substituted heteroaryl(lower alkyl), —C(=O)$R^{11}$, —C(=O)O$R^{11}$, —C(=O)N$R^{11}R^{12}$, —SO$_2R^{11}$, or —SO$_2NR^{11}R^{12}$, where $R^{11}$ and $R^{12}$ are independently, hydrogen, optionally substituted lower alkyl, alkenyl, alkynyl, cycloalkyl, cycloalkyl(lower alkyl), aryl, optionally substituted aryloxy, heteroaryl, heteroaryl (lower alkyl), or $R^{11}$ and $R^{12}$ together are —$(CH_2)_{4-6}$—, and the pharmaceutically acceptable salts thereof, optionally in the form of single stereoisomers or mixtures of stereoisomers thereof.

The compounds of this invention many possess one or more chiral centers, and can therefore be produced as individual stereoisomers or as mixtures of stereoisomers, depending on whether individual stereoisomers or mixtures of stereoisomers of the starting materials are used. In addition, some of the compounds of the invention are capable of further forming pharmaceutically acceptable salts and esters. The compounds of this invention may further exist in tautomeric forms and can therefore be produced as individual tautomeric forms or as mixtures of tautomeric forms. Unless indicated otherwise, the description or naming of a compound or groups of compounds is intended to include both the individual isomers or mixtures (racemic or otherwise) of stereoisomers and their tautomeric forms. Methods for the determination of stereochemistry and the separation of stereoisomers are well known to a person of ordinary skill in the art [see the discussion in Chapter 4 of March J.: *Advanced Organic Chemistry*, 4th ed. John Wiley and Sons, New York, N.Y., 1992]. All of these stereoisomers and pharmaceutical forms are intended to be included within the scope of the present invention.

A second embodiment of the present invention provides compounds of Formula (Ia) and Formula (IIa):

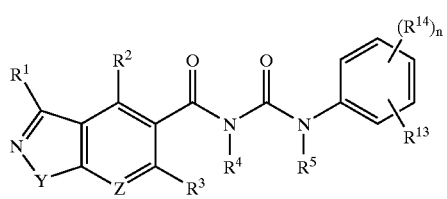

(Ia)

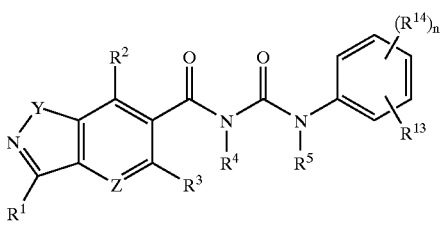

(IIa)

where:
Y is O, S or N—$R^7$,
Z is N or C—$R^8$,
$R^1$, $R^2$, $R^3$, $R^4$, $R^5$, $R^7$ and $R^8$ are as defined in the first embodiment, $R^{13}$ is hydrogen, optionally substituted lower alkyl, alkenyl, alkynyl, cycloalkyl, cycloalkyl(lower alkyl), heterocycloalkyl, optionally substituted aryl, optionally substituted aryl(lower alkyl), optionally substituted heteroaryl, optionally substituted heteroaryl(lower alkyl), halo(lower alkyl), —CF$_3$, halogen, nitro, —CN, —OR$^{15}$, —SR$^{15}$, —NR$^{15}R^{16}$, —C(=O)R$^{15}$, —C(=O)OR$^{15}$, —C(=O)NR$^{15}R^{16}$, —OC(=O)R$^{15}$, —SO$_2R^{15}$, —SO$_2NR^{15}R^{16}$, —NR$^{15}$SO$_2R^{16}$ or —NR$^{15}$C(=O)R$^{16}$, where are $R^{15}$ and $R^{16}$ independently, hydrogen, optionally substituted lower alkyl, alkenyl, alkynyl, —CF$_3$, cycloalkyl, optionally substituted heterocycloalkyl, cycloalkyl(lower alkyl), optionally substituted aryl, optionally substituted aryloxy, optionally substituted heteroaryl, optionally substituted heteroaryl)lower alkyl) or, together, are —(CH$_2$)$_{4-6}$— optionally interrupted by one O, S, NH or N—(C$_{1-2}$ alkyl group), each $R^{14}$ is independently selected from optionally substituted lower alkyl, optionally substituted aryl, optionally substituted heteroaryl, hydroxy, halogen, —CF$_3$, —OR$^{17}$, —NR$^{17}R^{18}$, —(=O)R$^{18}$, —C(=O)OR$^{18}$, —C(=O)NR$^{17}R^{18}$, where $R^{17}$ and $R^{18}$ are independently, hydrogen, lower alkyl, alkenyl, alkynyl, —CF$_3$, optionally substituted heterocycloalkyl, cycloalkyl, cycloalkyl(lower alkyl), optionally substituted aryl, optionally substituted aryloxy, heteroaryl, heteroaryl (lower alkyl), or, together, are —(CH$_2$)$_{4-6}$—, optionally interrupted by one O, S, NH or N—(C$_{1-2}$ alkyl) group, and n is an integer of 0 to 4, and the pharmaceutically acceptable salts thereof, optionally in the form of single stereoisomers or mixtures of stereoisomers thereof.

A third embodiment of the present invention provides pharmaceutical compositions comprising a pharmaceutically acceptable excipient and a therapeutically effective amount of at least one compound of this invention.

A fourth embodiment of the present invention provides methods for treating diseases treatable by administration of an MCP-1 inhibitor, for example, chronic or acute inflammatory or autoimmune diseases such as asthma, atherosclerosis, diabetic nephropathy, glomerulonephritis, inflammatory bowel disease, Crohn's disease, multiple sclerosis, pancreatitis, pulmonary fibrosis, psoriasis, restenosis, rheumatoid arthritis, or a transplant rejection in mammals in need thereof, comprising the administration to such mammal of a therapeutically effective amount of at least one compound of this invention or a pharmaceutically acceptable salt thereof or a pharmaceutical composition comprising the same.

A fifth embodiment of this invention provides processes for the preparation of the compounds of the invention and the pharmaceutically acceptable salts thereof.

DETAILED DESCRIPTION OF THE INVENTION

Definitions and General Parameters

The following definitions apply to the description of compounds of the present invention:

"Alkyl" is a linear or branched saturated hydrocarbon radical having from 1 to 20 carbon atoms. Examples of alkyl radicals are: methyl, ethyl, n-propyl, isopropyl, n-butyl, isobutyl, sec-butyl, tert-butyl, n-pentyl, n-hexyl, dodecyl, etc.

"Lower alkyl", as in "lower aryl," "lower alkoxy," "cycloalkyl(lower alkyl)," "aryl(lower alkyl)", or "heteroaryl(lower alkyl)", means a $C_{1-10}$ alkyl radical. Preferred lower alkyl radicals are those having from 1 to 6 carbon atoms.

"Alkenyl" is a linear or branched hydrocarbon radical having from 2 to 20 carbon atoms and at least one carbon-carbon double bond. Examples of alkenyl radicals are: vinyl, 1-propenyl, isobutenyl, etc.

"Alkynyl" is a linear or branched hydrocarbon radical having from 2 to 20 carbon atoms and at least one carbon-carbon triple bond. Examples of alkynyl radicals are: propargyl, 1-butynyl, etc.

"Cycloalkyl" is a monovalent cyclic hydrocarbon radical having from 3 to 12 carbon atoms. Examples of cycloalkyl radicals are: cyclopropyl, cyclobutyl, cyclopentyl, cyclohexyl, etc.

"Substituted cycloalkyl" is a monovalent cyclic hydrocarbon radical having from 3 to 12 carbon atoms, which is substituted with one, two, or three substituents each independently selected from aryl, substituted aryl, heteroaryl, halogen, —$CF_3$, nitro, —CN, —OR, —SR, —NRR', —C(=O)R, —OC(=O)R, —C(=O)OR, —$SO_2$OR, —$OSO_2$R, —$SO_2$NRR', —$NRSO_2$R', —C(=O)NRR', —NRC(=O)R' or —$PO_3$HR, where R and R' are, independently, hydrogen, lower alkyl, cycloalkyl, aryl, substituted aryl, aryl(lower alkyl), substituted aryl(lower alkyl), heteroaryl, or heteroaryl(lower alkyl), and having 3 to 12 ring atoms, 1 to 5 of which are heteroatoms chosen, independently, from N, O, or S, and includes monocyclic, condensed heterocyclic, and condensed carbocyclic and heterocyclic rings (e.g. piperidyl, 4-morpholyl, 4-piperazinyl, pyrrolidinyl, perhydropyrrolizinyl, 1,4-diazaperhydroepinyl [perhydro-1,4-diazepinyl], etc.).

"Cycloalkyl(lower alkyl)" is a lower alkyl radical which is substituted with a cycloalkyl, as previously defined. Examples of cycloalkyl(lower alkyl) radicals are cyclopropylmethyl, cyclobutylethyl, cyclopentylmethyl, cyclohexylmethyl, etc.

"Heterocycloalkyl" is a monovalent cyclic hydrocarbon radical having 3 to 12 carbon ring atoms, 1 to 5 of which are heteroatoms chosen, independently, from N, O, or S, and includes monocyclic, condensed heterocyclic, and condensed carbocyclic and heterocyclic rings (e.g. piperidyl, 4-morpholyl, 4-piperazinyl, pyrrolidinyl, perhydropyrrolizinyl, 1,4-diazaperhydroepinyl, etc.).

"Substituted heterocycloalkyl" is a monovalent cyclic hydrocarbon radical having from 3 to 12 carbon atoms, which is substituted with one, two, or three substituents each independently selected from alkyl, substituted aryl, heteroaryl, halogen, —$CF_3$ nitro, —CN, —OR, —SR, —NRR', —C(=O)R, —OC(=O)R, —C(=O)OR, —$SO_2$OR, —$OSO_2$R, —$SO_2$NRR', —$NRSO_2$R', —C(=O)NRR', —NRC(=O)R' or —$PO_3$HR, where R and R' are, independently, hydrogen, lower alkyl, cycloalkyl, aryl, substituted aryl, aryl(lower alkyl), substituted aryl(lower alkyl), heteroaryl, or heteroaryl(lower alkyl), and having 3 to 12 ring atoms, 1 to 5 of which are heteroatoms chosen, independently, from N, O, or S, and includes monocyclic, condensed heterocyclic, and condensed carbocyclic and heterocyclic rings (e.g. piperidyl, 4-morpholyl, 4-piperazinyl, pyrrolidinyl, perhydropyrrolizinyl, 1,4-diazaperhydroepinyl, etc.).

"Substituted heterocycloalkyl(lower alkyl)" is a lower alkyl radical which is substituted with a monovalent cyclic hydrocarbon radical having from 3 to 12 carbon atoms, which is substituted with one, two, or three substituents each independently selected from aryl, substituted aryl, heteroaryl, halogen, —$CF_3$ nitro, —CN, —OR, —SR, —NRR', —C(=O)R, —OC(=O)R, —C(=O)OR, —$SO_2$OR, —$OSO_2$R, —$SO_2$NRR', —$NRSO_2$R', —C(=O)NRR', —NRC(=O)R' or —$PO_3$HR, where R and R' are, independently, hydrogen, lower alkyl, cycloalkyl, aryl, substituted aryl, aryl(lower alkyl), substituted aryl(lower alkyl), heteroaryl, or heteroaryl(lower alkyl), and having 3 to 12 ring atoms, 1 to 5 of which are heteroatoms chosen, independently, from N, O, or S, and includes monocyclic, condensed heterocyclic, and condensed carbocyclic and heterocyclic rings (e.g. piperidyl, 4-morpholyl, 4-piperazinyl, pyrrolidinyl, perhydropyrrolizinyl, 1,4-diazaperhydroepinyl, etc.).

"Substituted alkyl" or "substituted lower alkyl," is an a or lower alkyl radical, respectively, which is substituted with one, two, or three substituents each independently selected from aryl, substituted aryl, heteroaryl, halogen, —$CF_3$ nitro, —CN, —OR, —SR, —NRR', —C(=O)R, —OC(=O)R, —C(=O)OR, —$SO_2$OR, —$OSO_2$R, —$SO_2$NRR', —$NRSO_2$R', —C(=O)NRR', —NRC(=O)R', or —$PO_3$HR, where R and R' are, independently, hydrogen, lower alkyl, cycloalkyl, aryl, substituted aryl, aryl(lower alkyl), substituted aryl(lower alkyl), heteroaryl, or heteroaryl(lower alkyl).

"Halo(lower alkyl)" is a radical derived from lower alkyl containing at least one halogen substituent. Non-limiting examples of halo(lower alkyl) radicals include: —$CF_3$, —$C_2F_5$, etc.

"Aryl", as in "aryl", "aryloxy", and "aryl(lower alkyl)", is a radical derived from an aromatic hydrocarbon containing 6 to 16 ring carbon atoms, having a single ring (e.g., phenyl, or two or more condensed rings, preferably 2 to 3 condensed rings (e.g., naphthyl), or two or more aromatic rings, preferably 2 to 3 aromatic rings, which are linked by a single bond (e.g., biphenyl). Preferred aryl radicals are those containing from 6 to 14 carbon atoms.

"Substituted aryl" is an aryl radical which is substituted with one, two, or three substituents each independently selected from alkyl, substituted alkyl, halo(lower alkyl), halogen, nitro, —CN, —OR, —SR, —NRR', —C(=O)R, —OC(=O)R, —C(=O)OR, —$SO_2$OR, —$OSO_2$R, —$SO_2$NRR', —$PO_3H_2$, —$NRSO_2$R', —C(=O)NRR' or —NRC(=O)R', where R and R' are, independently, hydrogen, lower alkyl, substituted lower alkyl, cycloalkyl, aryl, substituted aryl, optionally substituted aryl(lower alkyl), heteroaryl, or heteroaryl(lower alkyl). Preferred substituted aryl radicals are those substituted with one, two, or three substituents each independently selected from the group consisting of lower alkyl, halogen, —$CF_3$, nitro, —CN, —OR, —NRR', —C(=O)NRR', —$SO_2$OR, —$SO_2$NRR', —$PO_3H_2$, —$NRSO_2$R' or —NRC(=O)R'.

"Substituted aryloxy" is an —OR radical where R is a radical derived from an aromatic hydrocarbon containing 6 to 16 ring carbon atoms, having a single ring (e.g., phenyl), or two or more condensed rings, preferably 2 to 3 condensed rings (e.g., naphthyl, or two or more aromatic rings, preferably 2 to 3 aromatic rings, which are linked by a single bond (e.g., biphenyl, and which is substituted with one, two, or three substituents each independently selected from aryl, substituted aryl, heteroaryl, halogen, —$CF_3$, nitro, —CN, —OR, —SR, —NRR', —C(=O)R, —OC(=O)R, —C(=O)OR, $SO_2$OR, —$OSO_2$R, —$SO_2$NRR', —$NRSO_2$R', —C(=O)NRR', —NRC(=O)R' or —$PO_3$HR, where R and R' are, independently, hydrogen, lower alkyl, cycloalkyl, aryl, substituted aryl, aryl(lower alkyl), substituted aryl(lower alkyl), heteroaryl, or heteroaryl(lower alkyl). Preferred aryl radicals are those containing from 6 to 14 carbon atoms.

"Heteroaryl", as in "heteroaryl" and "heteroaryl(lower alkyl)", is a radical derived from an aromatic hydrocarbon containing 5 to 14 ring atoms, 1 to 5 of which are heteroatoms chosen, independently, from N, O, or S, and includes monocyclic, condensed heterocyclic, and condensed carbocyclic and heterocyclic aromatic rings (e.g., thienyl, furyl, pyrrolyl, pyrimidinyl, isoxazolyl, oxazolyl, indolyl, isobenzofuranyl, purinyl, isoquinolyl, pteridinyl, imidazolyl, pyridyl, pyrazolyl, pyrazinyl, quinolyl, etc.).

"Substituted heteroaryl" is a heteroaryl radical which is substituted with one, two, or three substituents each independently selected from alkyl, substituted alkyl, halogen, $CF_3$, nitro, —CN, —OR, —SR, —NRR', —C(=O)R, OC(=O)R, —C(=O)OR, —SO$_2$OR, —OSO$_2$R, —SO$_2$NRR', —NRSO$_2$R', —C(=O)NRR', or —NRC(=O)R', where R and R' are, independently, hydrogen, lower alkyl, substituted lower alkyl, cycloalkyl, aryl, substituted aryl, aryl(lower alkyl), substituted aryl(lower alkyl), heteroaryl, or heteroaryl(lower alkyl). Particularly preferred substituents on the substituted heteroaryl moiety include lower alkyl, substituted lower alkyl, halo(lower alkyl), halogen, nitro, —CN, —OR, —SR, and —NRR'.

"Aryl(lower alkyl)" is a lower alkyl radical which is substituted with an aryl, as previously defined.

"Substituted aryl(lower alkyl)" is an aryl(lower alkyl) radical having one to three substituents on either or both of the aryl and the alkyl portion of the radical.

"Heteroaryl(lower alkyl)," is a lower alkyl radical which is substituted with a heteroaryl, as previously defined.

"Substituted heteroaryl(lower alkyl)" is a heteroaryl (lower alkyl) radical having one to three substituents on the heteroaryl portion or the alkyl portion of the radical, or both.

"Lower alkoxy" is an —OR radical, where R is a lower alkyl or cycloalkyl.

"Halogen" means fluoro, chloro, bromo, or iodo.

"Stereoisomers" are compounds that have the same sequence of covalent bonds and differ in the relative disposition of their atoms in space.

"Inner salts" or "Zwitterions" can be formed by transferring a proton from the carboxyl group onto the lone pair of electrons of the nitrogen atom in the amino group.

"Tautomers" are isomeric compounds that differ from one another by interchanged positions of σ and π bonds. The compounds are in equilibrium with one another. They may also differ from one another in the position at which a hydrogen atom is attached.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salts and esters" means any salt and ester that is pharmaceutically acceptable and has the desired pharmacological properties. Such salts include salts that may be derived from an inorganic or organic acid, or an inorganic or organic base, including amino acids, which is not toxic or undesirable in anyway. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane and arene-sulfonic acids such as methanesulfonic acid and benzenesulfonic acid). Pharmaceutically acceptable esters; include esters formed from carboxy, sulfonyloxy, and phosphonoxy groups present in the compounds, e.g. $C_{1-6}$ alkyl esters. When there are two acidic groups present, a pharmaceutically acceptable salt or ester may be a mono-acid-mono-salt or ester or a di-salt or ester; and similarly, where there are more than two acidic groups present, some or all of such groups can be salified or esterified.

"Therapeutically effective amount" means that amount which, when administered to a mammal for treating a disease, is sufficient to effect such treatment for the disease.

"Treating" or "treatment" of a disease in a mammal includes:

Preventing the disease from occurring in a mammal which may be predisposed to the disease but does not yet experience or display symptoms of the disease;

Inhibiting the disease, i.e., arresting its development, or

Relieving the disease, i.e., causing regression of the disease.

"Disease" includes any unhealthy condition of an animal (which includes human and non-human mammals), including particularly various forms of inflammatory illnesses or diseases, such as asthma, atherosclerosis, diabetic nephropathy, glomerulonephritis, inflammatory bowel disease, Crohn's disease, multiple sclerosis, pancreatitis, pulmonary fibrosis, psoriasis, restenosis, rheumatoid arthritis, immune disorders, and transplant rejection.

The Compounds and Their Pharmaceutically Acceptable Salts

The first embodiment of the present invention provides compounds of Formula (I) and Formula (II):

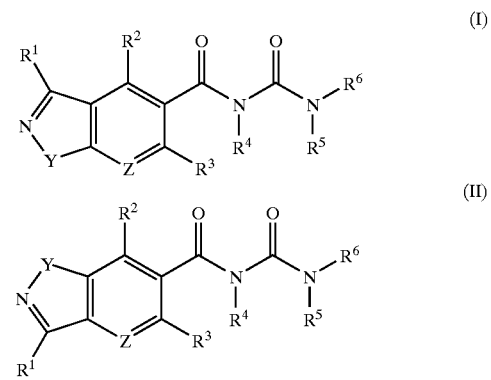

where Y, Z, and $R^1$ to $R^{12}$ are as defined above.

Where $R^9$ and $R^{10}$ together are —(CH$_2$)$_{4-6}$— optionally interrupted by one O, S, NH, N-(aryl), N-(aryl(lower alkyl)), N-(carboxy(lower alkyl) or N-(optionally substituted $C_{1-2}$ alkyl)) group, examples include piperidinyl, piperazinyl, 4-methylpiperazinyl, 4-(carboxymethyl)piperazinyl, 4-morpholyl, and hexahydropyrimidyl.

Preferably, Y is O or N—$R^7$.

Preferably, $R^1$ is hydrogen, optionally substituted lower alkyl, optionally substituted heterocycloalkyl, optionally substituted aryl, optionally substituted heteroaryl, optionally substituted aryl(lower alkyl), halogen, —OR$^9$, —NR$^9$R$^{10}$, —C(=O)OR$^9$, —C(=O)NR$^9$R$^{10}$, —SO$_2$NR$^9$R$^{10}$, or —NR$^9$—C(=O)R$^{10}$, where R$^9$ and R$^{10}$ are independently, hydrogen, optionally substituted lower alkyl, lower alkyl-N(C$_{1-2}$ alkyl)$_2$, lower alkyl(optionally substituted heterocycloalkyl), aryl(lower alkyl), optionally substituted aryl, heteroaryl, or heteroaryl(lower alkyl).

More preferably, R$^1$ is optionally substituted lower alkyl, optionally substituted heterocycloalkyl, optionally substituted aryl, optionally substituted heteroaryl, optionally substituted aryl(lower alkyl), halogen, —OR$^9$, —NR$^9$R$^{10}$, —C(=O)OR$^9$, —C(=O)NR$^9$R$^{10}$, —SO$_2$NR$^9$R$^{10}$, or —NR$^9$C(=O)R$^{10}$, where R$^9$ and R$^{10}$ are independently, hydrogen, optionally substituted lower alkyl, lower alkyl-N(C$_{1-2}$ alkyl)$_2$, lower alkyl(optionally substituted heterocycloalkyl), aryl(lower alkyl), optionally substituted aryl, heteroaryl, or heteroaryl(lower alkyl).

Preferably, R$^2$ is hydrogen, optionally substituted lower alkyl, cycloalkyl, optionally substituted heterocycloalkyl, optionally substituted aryl, optionally substituted heteroaryl, optionally substituted aryl(lower alkyl), halogen, —OR$^9$, —NR$^9$(carboxy(lower alkyl), —C(=O)OR$^9$, —C(=O)NR$^9$R$^{10}$, —SO$_2$NR$^9$R$^{10}$, or —NR$^9$C(=O)R$^{10}$, where R$^9$ and R$^{10}$ are independently, hydrogen, optionally substituted lower alkyl, lower alkyl-N(C$_{1-2}$ alkyl)$_2$, lower alkyl(optionally substituted heterocycloalkyl), optionally substituted cycloalkyl, cycloalkyl(lower alkyl), optionally substituted aryl, optionally substituted aryloxy, heteroaryl, heteroaryl (lower alkyl), or R$^9$ and R$^{10}$ together are —(CH$_2$)$_{4-6}$— optionally interrupted by one O, S, NH, N-(aryl), N-(aryl (lower alkyl)), N-(carboxy(lower alkyl)) or N-(optionally substituted C$_{1-2}$ alkyl) group.

More preferably, R$^2$ is optionally substituted lower alkyl, cycloalkyl, optionally substituted heterocycloalkyl, optionally substituted aryl, optionally substituted heteroaryl, optionally substituted aryl(lower alkyl), halogen, —OR$^9$, —NR$^9$(carboxy(lower alkyl)), —C(=O)OR$^9$, —C(=O)NR$^9$R$^{10}$, —SO$_2$NR$^9$R$^{10}$, or —NR$^9$C(=O)R$^{10}$, where R$^9$ and R$^{10}$ are independently, hydrogen, optionally substituted lower alkyl, lower alkyl-N(C$_{1-2}$ alkyl)$_2$, lower alkyl(optionally substituted heterocycloalkyl), optionally substituted cycloalkyl, cycloalkyl(lower alkyl), optionally substituted aryl, optionally substituted aryloxy, heteroaryl, heteroaryl (lower alkyl), or R$^9$ and R$^{10}$ together are —(CH$_2$)$_{4-6}$— optionally interrupted by one O, S, NH, N-(aryl), N-(aryl (lower alkyl)), N-(carboxy(lower alkyl)) or N-(optionally substituted C$_{1-2}$ alkyl) group.

Preferably, R$^3$ is hydrogen, optionally substituted lower alkyl, optionally substituted heterocycloalkyl, optionally substituted aryl, optionally substituted heteroaryl, optionally substituted aryl(lower alkyl), halo(lower alkyl), halogen, —OR$^9$, —NR$^9$R$^{10}$, —C(=O)OR$^9$, or —C(=O)NR$^9$R$^{10}$, where R$^9$ and R$^{10}$ are independently, hydrogen, optionally substituted lower alkyl, lower alkyl-N(C$_{1-2}$ alkyl)$_2$, lower alkyl(optionally substituted heterocycloalkyl, optionally substituted cycloalkyl, cycloalkyl(lower alkyl), optionally substituted aryl), optionally substituted aryloxy, heteroaryl, heteroaryl(lower alkyl), or R$^9$ and R$^{10}$ together are —(CH$_2$)$_{4-6}$— optionally interrupted by one O, S, NH, N-(aryl), N-(aryl(lower alkyl)), N-(carboxy(lower alkyl)) or N-(optionally substituted C$_{1-2}$ alkyl) group.

More preferably, R$^3$ is optionally substituted lower alkyl, optionally substituted heterocycloalkyl, optionally substituted aryl, optionally substituted heteroaryl, optionally substituted aryl(lower alkyl), halo(lower alkyl), halogen, —OR$^9$, —NR$^9$R$^{10}$, —C(=O)OR$^9$, or —C(=O)NR$^9$R$^{10}$, where R$^9$ and R$^{10}$ are independently, hydrogen, optionally substituted lower alkyl, lower alkyl-N(C$_{1-2}$ alkyl)$_2$, lower alkyl(optionally substituted heterocycloalkyl), optionally substituted cycloalkyl, cycloalkyl(lower alkyl), optionally substituted aryl, optionally substituted aryloxy, heteroaryl (lower alkyl), or R$^9$ and R$^{10}$ together are —(CH$_2$)$_{4-6}$— optionally interrupted by one O, S, NH, N-(aryl), N-(aryl (lower alkyl)), N-(carboxy(lower alkyl)) or N-(optionally substituted C$_{1-2}$ alkyl) group.

Preferably, R$^7$ is hydrogen, optionally substituted lower alkyl, optionally substituted heterocycloalkyl, optionally substituted aryl, optionally substituted heteroaryl, optionally substituted aryl(lower alkyl), —C(=O)R$^9$, —C(=O)OR$^9$, —C(=O)NR$^9$R$^{10}$, —SO$_2$R$^9$, or —SO$_2$NR$^9$R$^{10}$, where R$^9$ and R$^{10}$ are independently, hydrogen, optionally substituted lower alkyl, lower alkyl-N(C$_{1-2}$ alkyl)$_2$, alkenyl, alkynyl, optionally substituted cycloalkyl, cycloalkyl(lower alkyl), optionally substituted aryl, heteroaryl, or heteroaryl(lower alkyl).

Preferably, R$^8$ is hydrogen, optionally substituted lower alkyl, optionally substituted heterocycloalkyl, optionally substituted aryl, optionally substituted heteroaryl, optionally substituted aryl(lower alkyl), halo(lower alkyl), —CF$_3$, halogen, —OR$^9$, —NR$^9$R$^{10}$, —C(=O)R$^9$, —C(=O)OR$^9$, —C(=O)NR$^9$R$^{10}$, —OC(=O)R$^9$, —SO$_2$R$^9$, —SO$_2$NR$^9$R$^{10}$, —NR$^9$SO$_2$OR$^9$ or —NR$^9$C(=O)R$^{10}$, where R$^9$ and R$^{10}$ are independently, hydrogen, optionally substituted lower alkyl, lower alkyl-N(C$_{1-2}$ alkyl)$_2$, optionally substituted cycloalkyl, cycloalkyl(lower alkyl), optionally substituted aryl, heteroaryl, heteroaryl(lower alkyl), or R$^9$ and R$^{10}$ together are —(CH$_2$)$_{4-6}$— optionally interrupted by one O, S, NH, N-(alkyl), N-(aryl(lower alkyl)), N-(carboxy (lower alkyl)) or N-(optionally substituted C$_{1-2}$ alkyl) group.

Preferably, R$^4$ and R$^5$ are independently, hydrogen or lower alkyl, or together are —(CH$_2$)$_{2-4}$—. More preferably, R$^4$ and R$^5$ are independently, hydrogen or lower alkyl.

Preferably, R$^6$ is hydrogen, optionally substituted lower a , alkenyl, cycloalkyl, cycloalkyl(lower alkyl), optionally substituted heterocycloalkyl, optionally substituted aryl, optionally substituted aryl(lower alkyl), optionally substituted heteroaryl, optionally substituted heteroaryl(lower alkyl), —C(=O)R$^{11}$, —C(=O)OR$^{11}$, —C(=O)NR$^{11}$R$^{12}$, —SO$_2$R$^{11}$, or —SO$_2$NR$^{11}$R$^{12}$, where R$^{11}$ and R$^{12}$ are independently, hydrogen, optionally substituted lower alkyl, cycloalkyl, cycloalkyl(lower alkyl), aryl, heteroaryl, heteroaryl(lower alkyl), or R$^{11}$ and R$^{12}$ together are —(CH$_2$)$_{4-6}$—.

A particularly preferred "substituted aryl" is a phenyl group substituted with R$^{13}$ and optionally substituted with up to four R$^{14}$s, where R$^{13}$ and R$^{14}$ are defined with respect to formulae Ia and IIa.

The above-listed preferences equally apply for the compounds of Formulae Ia and IIa, below.

In a more preferred version of the first embodiment of the invention,

Y is N—R$^7$ and Z is N,
R$^1$ is lower alkyl,
R$^4$ and R$^5$ are hydrogen, and
R$^6$ is hydrogen, optionally substituted lower alkyl, alkenyl, alkynyl, cycloalkyl, cycloalkyl(lower alkyl), optionally substituted heterocycloalkyl, optionally substituted aryl, aryl(lower alkyl), optionally substituted heteroaryl, optionally substituted heteroaryl(lower alkyl), halo(lower alkyl), —C(=O)R$^{11}$, —C(=O) OR$^{11}$, —C(=O)NR$^{11}$R$^{12}$, —SO$_2$R$^{11}$, or —SO$_2$NR$^{11}$R$^{12}$, where R$^{11}$ and R$^{12}$ are independently, hydrogen, optionally substituted lower alkyl, alkenyl, alkynyl, cycloalkyl, cycloalkyl(lower alkyl), aryl, optionally substituted aryloxy, heteroaryl, heteroaryl (lower alkyl), or $R^{11}$ and $R^{12}$ together are —$(CH_2)_{4-6}$—, or a pharmaceutically acceptable salt thereof, optionally in the form of a single stereoisomer or mixture of stereoisomers thereof.

More preferably still, $R^2$ is —$NR^9R^{10}$, where $R^9$ and $R^{10}$ are independently, hydrogen, optionally substituted lower alkyl, lower alkyl-$N(C_{1-2}$ alkyl)$_2$, lower aryl(optionally substituted heterocycloalkyl), alkenyl, alkynyl, optionally substituted cycloalkyl, cycloalkyl(lower alkyl), benzyl, optionally substituted aryl, optionally substituted aryloxy, heteroaryl, heteroaryl(lower alkyl), or $R^9$ and $R^{10}$ together are —$(CH_2)_{4-6}$— optionally interrupted by one O, S, NH, N-(aryl), N-(aryl(lower alkyl)), N-(carboxy(lower alkyl)) or N-(optionally substituted $C_{1-2}$ alkyl) group.

In another more preferred version of the first embodiment of the invention,

Y is N—$R^7$ and Z are N,
$R^1$ and $R^8$ are lower alkyl,
$R^2$ is —$NR^9R^{10}$,
$R^4$ and $R^5$ are hydrogen, and
$R^6$ is hydrogen, optionally substituted lower alkyl, alkenyl, alkynyl, cycloalkyl, cycloalkyl(lower alkyl), optionally substituted heterocycloalkyl, optionally substituted aryl, aryl(lower alkyl), optionally substituted heteroaryl, optionally substituted heteroaryl(lower alkyl), halo(lower alkyl), —$C(=O)R^{11}$, —$C(=O)OR^{11}$, —$C(=O)NR^{11}R^{12}$, —$SO_2R^{11}$, or —$SO_2NR^{11}R^{12}$, where $R^{11}$ and $R^{12}$ are independently, hydrogen, optionally substituted lower alkyl, alkenyl, alkynyl, cycloalkyl, cycloalkyl(lower alkyl), aryl, optionally substituted aryloxy, heteroaryl, heteroaryl (lower alkyl), or $R^{11}$ and $R^{12}$ together are —$(CH_2)_{4-6}$—, or a pharmaceutically acceptable salt thereof, optionally in the form of a single stereoisomer or mixture of stereoisomers thereof.

The second embodiment of the present invention provides compounds of Formula (Ia) or Formula (IIa):

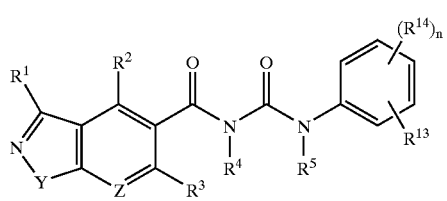
(Ia)

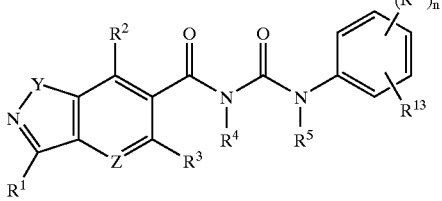
(IIa)

where:
Y is O, S or N—$R^7$,
Z is N or C—$R^8$, $R^1$, $R^2$, $R^3$, $R^4$, $R^5$, $R^7$ and $R^8$ are as defined in the first embodiment, $R^{13}$ is hydrogen, optionally substituted lower alkyl, alkenyl, alkynyl, cycloalkyl, cycloalkyl(lower alkyl), heterocycloalkyl, optionally substituted aryl, optionally substituted aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, $NR^{15}R^{16}$, —$C(=O)R^{15}$, —$C(=O)OR^{15}$, —$C(=O)NR^{15}R^{16}$, —$OC(=O)R^{15}$, —$SO_2R^{15}$, —$SO_2NR^{15}R^{16}$, —$NR^{15}SO_2R^{16}$ or —$NR^{15}C(=O)R^{16}$, where $R^{15}$ and $R^{16}$ are independently, hydrogen, optionally substituted lower alkyl, alkenyl, alkynyl, —$CF_3$, cycloalkyl, optionally substituted heterocycloalkyl, cycloalkyl(lower alkyl), optionally substituted aryl, optionally substituted aryloxy, optionally substituted heteroaryl, optionally substituted heteroaryl (lower alkyl), or, together, are —$(CH_2)_{4-6}$— optionally interrupted by one O, S, NH or N—$(C_{1-2}$ alkyl) group, each $R^{14}$ is independently selected from optionally substituted lower alkyl, optionally substituted aryl, optionally substituted heteroaryl, hydroxy, halogen, —$CF_3$, —$OR^{17}$ —$NR^{17}R^{18}$, —$C(=O)R^{18}$, —$C(=O)OR^{18}$, —$C(=O)NR^{17}R^{18}$, where $R^{17}$ and $R^{18}$ are independently, hydrogen, lower alkyl, alkenyl, alkynyl, —$CF_3$, optionally substituted heterocycloalkyl, cycloalkyl, cycloalkyl(lower alkyl), optionally substituted aryl, optionally substituted aryloxy, heteroaryl, heteroaryl (lower alkyl), or, together, are —$(CH_2)_{4-6}$—, optionally interrupted by one O, S, NH or N—$(C_{1-2}$ alkyl) group, and n is an integer of 0 to 4, or a pharmaceutically acceptable salt thereof as a single stereoisomer or mixture of stereoisomers.

Where $R^{13}$ is —$OR^{15}$, and $R^{15}$ is optionally substituted lower alkyl, it may, for example, be optionally substituted with —$C(=O)OR^{19}$, where $R^{19}$ is hydrogen or lower alkyl.

Where $R^9$ and $R^{10}$ together are —$(CH_2)_{4-6}$— optionally interrupted by one O, S, NH or N—$(C_{1-2}$ alkyl) group, examples include piperidinyl, piperazinyl, 4-methylpiperazinyl, morpholyl, and hexahydropyrimidyl.

n is a stereocompatible integer of 0 to 4. The term "stereocompatible" limits the number of substituents permissible by available valences in accordance with space requirements of the substituents.

Preferably, $R^{13}$ is hydrogen, optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, —$NR^{15}R^{16}$, —$C(=O)R^{15}$, —$C(=O)OR^{15}$, —$C(=O)NR^{15}R^{16}$, —$OC(=O)R^{15}$, —$SO_2R^{15}$, —$SO_2NR^{15}R^{16}$, or —$NR^{15}C(=O)R^{16}$, where $R^{15}$ and $R^{16}$ are independently, hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl(lower alkyl) or, together, are —$(CH_2)_{4-6}$— optionally interrupted by one O, S, NH or N—$(C_{1-2}$ alkyl) group.

More preferably, $R^{13}$ is optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, —$NR^{15}R^{16}$, —$C(=O)R^{15}$, —$C(=O)$ $OR^{15}$, $-C(=O)NR^{15}R^{16}$, $-OC(=O)R^{15}$, $-SO_2NR^{15}$, $-SO_2NR^{15}R^{16}$, or $-NR^{15}C(=O)R^{16}$, where $R^{15}$ and $R^{16}$ are independently, hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl(lower alkyl) or, together, are $-(CH_2)_{4-6}-$ optionally interrupted by one O, S, NH or N—($C_{1-2}$ alkyl) group.

Preferably, $R^{14}$ is independently selected from optionally substituted lower alkyl, optionally substituted aryl, optionally substituted heteroaryl, hydroxy, halogen, $-CF_3$, $-OR^{17}$ $-NR^{17}R^{18}$, $-C(=O)R^{18}$, $-C(=O)OR^{18}$, $-C(=O)NR^{17}R^{18}$, where $R^{17}$ and $R^{18}$ are, independently, hydrogen, lower alkyl, alkenyl, or optionally substituted aryl.

Preferably, where $R^{13}$ is not hydrogen, n is an integer of 1 to 2. More preferably, where $R^{13}$ is not hydrogen, n is 1.

In another more preferred version of the second embodiment of the invention,

Y is N—$R^7$ and Z is N,
$R^1$ is lower alkyl,
$R^2$ is $-NR^9R^{10}$, where $R^9$ and $R^{10}$ are independently, hydrogen, optionally substituted lower alkyl, lower alkyl-N($C_{1-2}$ alkyl)$_2$, lower alkyl(optionally substituted heterocycloalkyl), alkenyl, alkynyl, optionally substituted cycloalkyl, cycloalkyl(lower alkyl), benzyl, optionally substituted aryl, optionally substituted aryloxy, heteroaryl, heteroaryl(lower alkyl), or $R^9$ and $R^{10}$ together are $-(CH_2)_{4-6}-$ optionally interrupted by one O, S, NH, N-(aryl), N-(aryl(lower alkyl)), N-(carboxy(lower alkyl)) or N-(optionally substituted $C_{1-2}$ group such as piperazinyl, 4-methylpiperazinyl, 4-morpholyl, hexahydropyrimidyl, and
$R^{13}$ is hydrogen, optionally substituted lower alkyl, alkenyl, alkynyl, cycloalkyl, cycloalkyl(lower alkyl), heterocycloalkyl, optionally substituted aryl, aryl(lower alkyl), optionally substituted heteroaryl, optionally substituted heteroaryl(lower alkyl), halo(lower alkyl), $-CF_3$, halogen, nitro, $-CN$, $-OR^{15}$, $-SR^{15}$, $-NR^{15}R^{16}$, $-C(=O)R^{15}$, $-C(=O)OR^{15}$, $-C(=O)NR^{15}R^{16}$, $-OC(=O)R^{15}$, $-SO_2R^{15}$, $-SO_2NR^{15}R^{16}$, $-NR^{15}SO_2R^{16}$ or $-NR^{15}C(=O)R^{16}$, where $R^{15}$ and $R^{16}$ are independently, hydrogen, lower alkyl, alkenyl, alkynyl, $-CF_3$, cycloalkyl, optionally substituted heterocycloalkyl, cycloalkyl(lower alkyl), optionally substituted aryl, optionally substituted aryloxy, optionally substituted heteroaryl, optionally substituted heteroaryl (lower alkyl) or $R^{15}$ and $R^{16}$ together are $-(CH_2)_{4-6}-$ optionally interrupted by one O, S, NH or N—($C_{1-2}$ alkyl) group.

More preferably still, $R^4$ and $R^5$ are hydrogen.
Most preferably, independently,
1. Y is O, and R is lower aryl.
2. Y is N—$R^7$, $R^7$ is hydrogen or lower alkyl, and $R^1$ is lower alkyl.
3. Y is N—$R^7$, and $R^7$ is methyl.
4. Z is N.
5. Z is C—$R^8$, and $R^8$ is hydrogen.
6. $R^2$ and $R^3$ are independently selected from hydrogen, lower alkyl, halogen, $OR^9$, $-NR^9R^{10}$, where $R^9$ and $R^{10}$ are independently lower alkyl, substituted lower alkyl, or substituted aryl, or $R^9$ and $R^{10}$ together are $-(CH_2)_{4-6}-$ optionally interrupted by one O, S, NH, N-(aryl), N-(aryl(lower alkyl)), N—COOH, N-(carboxy(lower alkyl)) or N-(optionally substituted $C_{1-2}$ alkyl) group.
7. $R^{13}$ is independently selected from halogen, optionally substituted aryl, $-CF_3$, $-CH_3$, $-CN$, $-OR^{15}$, $-C(=O)R^{15}$, $-C(=O)OR^{15}$, $-C(=O)NR^{15}R^{16}$, or $-CO_2H$.
8. $R^{14}$ is independently selected from halogen, optionally substituted lower alkyl, $-CF_3$, $-OR^{17}$, aryl, heteroaryl, $-NR^{17}R^{18}$, $-C(=O)R^{17}$, $-C(=O)OR^{17}$, $-C(=O)NR^{17}R^{18}$, or $-CO_2H$, where $R^{17}$ and $R^{18}$ are, independently, lower alkyl, substituted lower alkyl, or substituted aryl, or, together, are $-(CH_2)_{4-6}-$ optionally interrupted by one O, S, NH or N—($C_{1-2}$ alkyl) group.
9. Z is N, $R^2$ is 4-methylpiperazinyl, $R^{13}$ is 3-$CF_3$, and $R^{14}$ is 4-F.

The preferred compounds of the invention are listed in Tables 1–4 below.

The compounds of this invention may possess one or more chiral centers, and can therefore exist as individual stereoisomers or as mixtures of stereoisomers. In such cases, all stereoisomers also fall within the scope of this invention. The compounds of this invention may also exist in various tautomeric forms, and in such cases, all tautomers also fall within the scope of this invention. The invention compounds include the individually isolated stereoisomers and tautomers as well as mixtures of such stereoisomers and their tautomers.

Some of the compounds of Formula (I) and Formula (II) are capable of further forming pharmaceutically acceptable salts and esters. All of these forms are included within the scope of the present invention.

Pharmaceutically acceptable base addition salts of the compounds of Formula (I) and Formula (II) include salts which may be formed when acidic protons present in the parent compound are capable of reacting with inorganic or organic bases. Typically, the parent compound is treated with an excess of an alkaline reagent, such as hydroxide, carbonate, or alkoxide, containing an appropriate cation. Cations such as Na$^+$, K$^+$, $-Ca^{2+}$, and NH$_4^+$ are examples of cations present in pharmaceutically acceptable salts. The Na$^+$ salts are especially useful. Acceptable inorganic bases, therefore, include aluminum hydroxide, calcium hydroxide, potassium hydroxide, sodium carbonate and sodium hydroxide. Salts may also be prepared using organic bases, such as choline, dicyclohexylamine, ethylenediamine, ethanolamine, diethanolamine, triethanolamine, procaine, N-methylglucamine, and the like [for a nonexclusive list see, for example, Berge et al., "Pharmaceutical Salts," *J. Pharma. Sci.* 66:1 (1977)]. The free acid form may be regenerated by contacting the base addition salt with an acid and isolating the free acid in the conventional manner. The free acid forms can differ from their respective salt forms somewhat in certain physical properties such as solubility in polar solvents.

Pharmaceutically acceptable acid addition salts of the compounds of Formula (I) and Formula (II) include salts which may be formed when the parent compound contains a basic group. Acid addition salts of the compounds are prepared in a suitable solvent from the parent compound and an excess of a non-toxic inorganic acid, such as hydrochloric acid, hydrobromic acid, sulfuric acid (giving the sulfate and bisulfate salts), nitric acid, phosphoric acid and the like, or a non-toxic organic acid such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, hexanoic acid, heptanoic acid, cyclopentanepropionic acid, lactic acid, o-(4-hydroxy-benzoyl) benzoic acid, 1,2-ethanedisulfonic acid, 2-hydroxyethanesulfonic acid, benzenesulfonic acid, p-chlorobenzenesulfonic acid, 2-naphthalenesulfonic acid, camphorsulfonic acid, 4-methyl-bicyclo[2.2.2.]oct-2-ene-1-carboxylic acid, glucoheptonic acid, gluconic acid, 4,4'-methylenebis(3-hydroxy-2-naphthoic)acid, 3-phenylpropionic acid, trimethylacetic acid, tert-butylacetic acid, laurylsulfuric acid, glucuronic acid, glutamic acid, 3-hydroxy-2-naphthoic acid, stearic acid, muconic acid, and the like. The free base form may be regenerated by contacting the acid addition salt with a base and isolating the free base in the conventional manner. The free base forms can differ from their respective salt forms somewhat in certain physical properties such as solubility in polar solvents.

Also included in the embodiment of the present invention are salts of amino acids such as arginate and the like, gluconate, and galacturonate [see Berge, supra (1977)].

Some of the compounds of the invention may form inner salts or Zwitterions.

Certain of the compounds of the present invention can exist in unsolvated forms as well as solvated forms, including hydrated forms, and are intended to be encompassed within the scope of the present invention.

Certain of the compounds of the present invention may also exist in one or more solid or crystalline phases or polymorphs, the variable biological activities of such polymorphs or mixtures of such polymorphs are also included in the scope of this invention.

Pharmaceutical Compositions

A third embodiment of the present invention provides pharmaceutical compositions comprising pharmaceutically acceptable excipients and a therapeutically effective amount of at least one compound of this invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. It may be desirable to add excipients such as polyvinylpyrrolidinone, gelatin, hydroxycellulose, acacia, polyethylene glycol, mannitol, sodium chloride, or sodium citrate.

Alternatively, these compounds maybe encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols, or water. Solid carriers include starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The amount of solid carrier varies but, preferably, will be between about 20 mg to about 1 g per dosage unit.

The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation may be administered directly p.o. or filled into a soft gelatin capsule.

Some specific examples of suitable pharmaceutical compositions are described in Examples 27–29.

Typically, a pharmaceutical composition of the present invention is packaged in a container with a label indicating the use of the pharmaceutical composition in the treatment of a disease such as asthma, atherosclerosis, diabetic nephropathy, glomerulonephritis, inflammatory bowel disease, Crohn's disease, multiple sclerosis, pancreatitis, pulmonary fibrosis, psoriasis, restenosis, rheumatoid arthritis, and transplant rejection, or a chronic or acute immune disorder, or a combination of any of these disease conditions.

Methods of Use

A fourth embodiment of the present invention provides a method for treating a disease treatable by administration of an MCP-1 inhibitor, for example, chronic or acute inflammatory disease such as asthma, atherosclerosis, diabetic nephropathy, glomerulonephritis, inflammatory bowel disease, Crohn's disease, multiple sclerosis, pancreatitis, pulmonary fibrosis, psoriasis, restenosis, rheumatoid arthritis, or a chronic or acute immune disorder, or a transplant rejection in mammals in need thereof, comprising the administration to such mammal of a therapeutically effective amount of at least one compound of Formula (I), Formula (Ia), Formula (II), Formula (IIa), or a pharmaceutically acceptable salt or ester thereof.

The compounds of the present invention inhibit chemotaxis of a human monocytic cell line (THP-1 cells) induced by human MCP-1 in vitro. This inhibitory effect has also been observed in vivo. The compounds have been shown to reduce monocyte infiltration in a thioglycollate-induced inflammation model in mice.

The compounds of the present invention have been found to prevent the onset or ameliorate symptoms in several animal models of inflammation. For example, the compounds inhibited recruitment of monocytes into the glomeruli in an anti-Thy-1 antibody-induced model of nephritis; reduced paw swelling in a rat model of adjuvant arthritis; inhibited neointimal hyperplasia after balloon injury in a rat model of restenosis, and reduced the amount of lesion of the aortic sinus in an apoE-deficient mouse model of atherosclerosis.

The ability of the compounds of this invention to block the migration of monocytes and prevent or ameliorate inflammation, which is demonstrated in the specific examples, indicates their usefulness in the treatment and management of disease states associated with aberrant leukocyte recruitment.

The use of the compounds of the invention for treating inflammatory and autoimmune disease by combination therapy may also comprise the administration of the compound of the invention to a mammal in combination with common anti-inflammatory drugs, cytokines, or immunomodulators.

The compounds of this invention are thus used to inhibit leukocyte migration in patients which require such treatment. The method of treatment comprises the administration, orally or parenterally, of an effective quantity of the chosen compound of the invention, preferably dispersed in a pharmaceutical carrier. Dosage units of the active ingredient are generally selected from the range of 0.01 to 1000 mg/kg, preferably 0.01 to 100 mg/kg, and more preferably 0.1 to 50 mg/kg, but the range will be readily determined by one skilled in the art depending on the route of administration, age, and condition of the patient. These dosage units may be administered one to ten times daily for acute or chronic disease. No unacceptable toxicological effects are expected when compounds of the invention are used in accordance with the present invention.

The invention compounds maybe administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like, or may be administered orally. Formulations may optionally be liposomal formulations, emulsions, formulations designed to administer the drug across mucosal membranes or transdermal formulations. Suitable formulations for each of these methods of administration maybe found in, for example, "Remington: The Science and Practice of Pharmacy", A. Gennaro, ed., 20th edition, Lippincott, Williams & Wilkins, Philadelphia, Pa.

EXAMPLES

The following Examples serve to illustrate the preparation, properties, and therapeutic applications of the compounds of this invention. These Examples are not intended to limit the scope of this invention, but rather to show how to prepare and use the compounds of this invention.

Preparation of the Compounds of the Invention: General Procedures:

The following general procedures may be employed for the preparation of the compounds of the present invention.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as Fieser and Fieser's *Reagents for Organic Synthesis*, vols. 1–17, John Wiley and Sons, New York N.Y., 1991; *Rodd's Chemistry of Carbon Compounds*, vols. 1–5 and supps., Elsevier Science Publishers, 1989; Organic Reactions, vols. 1–40, John Wiley and Sons, New York, N.Y., March 1991; J.: *Advanced Organic Chemistry*, 4th ed., John Wiley and Sons, New York N.Y.; and Larock: *Comprehensive Organic Transformations*, VCH Publishers, New York, 1989.

In some cases, protective groups maybe introduced and finally removed. For example, suitable protective groups for amino, hydroxy, and carboxy groups are described in Greene et al., *Protective Groups Organic Sythesis*, Second Edition, John Wiley and Sons, New York, 1991. Activation of carboxylic acids can be achieved by using a number of different reagents as described in Larock: *Comprehensive Organic Transformations*, VCH Publishers, New York, 1989.

The starting materials, intermediates, and compounds of this invention may be isolated and purified using conventional techniques, including precipitation, filtration, distillation, crystallization, chromatography, and the like. The compounds may be characterized using conventional methods, including physical constants and spectroscopic methods.

Generally, a compound of formula I or formula II:

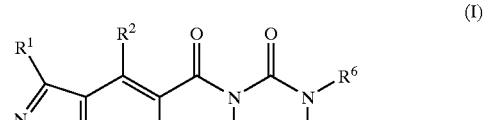

(I)

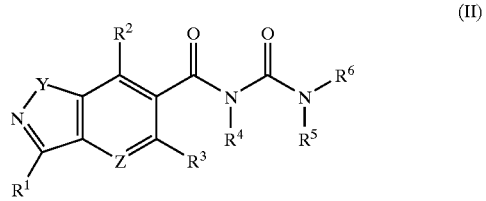

(II)

where Y, Z, and $R^1$–$R^6$ are as defined in the first embodiment, may be prepared by a process comprising:

contacting a compound of formula Ib or IIb

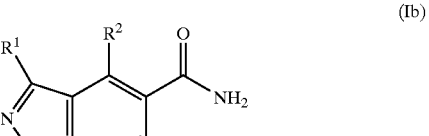

(Ib)

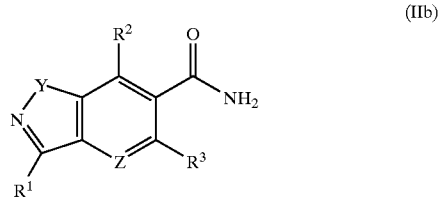

(IIb)

with a compound of the formula $R^6$—N=C=O under conditions sufficient to produce a compounds of formula I or formula II, where $R^4$ and $R^5$ are both H; or contacting a compound of formula Ic or formula IIc

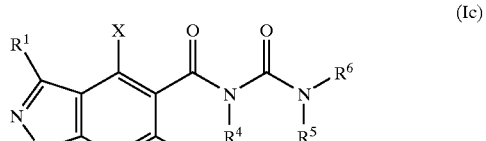

(Ic)

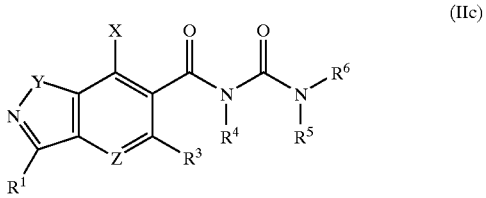

(IIc)

where X is halogen, nitro, —CN, or —$OR^9$, with a compound of the formula $R^2$—H under conditions sufficient to produce a compound of formula I or formula II; or contacting a compound of formula Ib or formula IIb

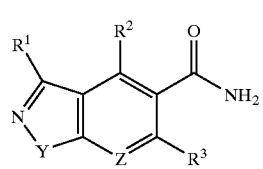
(Ib)

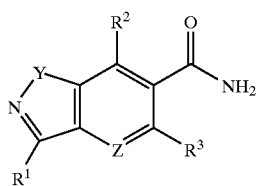
(IIb)

with a haloformylation reagent and a compound of the formula $R^5R^6NH$ under conditions sufficient to produce a compound of formula I or formula II, where $R^4$ is H; or elaborating substituents of a compound of formula I or formula II in a manner known per se; or reacting the free base of a compound of formula I or formula II with an acid to give a pharmaceutically acceptable addition salt; or reacting an acid addition salt of a compound of formula I or formula II with a base to form the corresponding free base; or converting a salt of a compound of formula I or formula II to another pharmaceutically acceptable salt of a compound of Formula I or II; or resolving a racemic mixture of any proportions of a compound of formula I or formula II to yield a stereoisomer thereof.

Step (a), above, maybe be carried out in the presence of an organic solvent or a mixture of solvents at elevated temperatures. Said organic solvent may be toluene, and the reaction may be carried out under refluxing conditions.

Step (b), above, maybe be carried out using the salt of the compound of the formula $R^2$—H in an inorganic solvent. Said salt may be the lithium, sodium, or potassium salt.

Step (c), above, maybe be carried out in an organic solvent or a mixture of solvents at elevated temperatures. The haloformylation reagent maybe a compound of the formula A-(CO)—B where A and B are, independently, suitable leaving groups such as halogens, —COCl, —COBr and the like. The haloformylation agent and organic solvent employed in step (c) may be oxalyl chloride and THF, respectively, and the ensuing reaction may be heated to above 50° C.

The compounds of the invention can further be synthesized as shown in the following examples. These examples are merely illustrative of some methods by which the compounds of this invention can be synthesized, and various modifications to these examples can be made and will be suggested to a person of ordinary skill in the art having regard to this disclosure.

Procedure A:

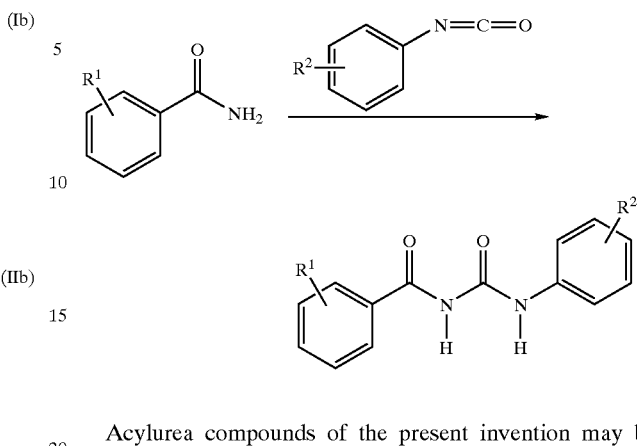

Acylurea compounds of the present invention may be prepared starting with an aryl carboxamide and an isocyanate. Carboxamide and isocyanate starting materials may be purchased from various different commercial sources, such as, for example the Aldrich Chemical Company, supra, or they may be prepared from standard procedures known in the art for preparing these compounds, such as the procedures described in the above-cited references. The isocyanates may also be prepared according to the procedures described in the example below. Typically, an aryl carboxamide is treated with an aryl isocyanate in an organic solvent or mixtures of suitable organic solvents. Preferably, the organic solvent is toluene. The carboxamide and the isocyanate may be combined as solutions or suspensions, depending on the solubilities of the compounds in the selected solvent. The carboxamide and the isocyanate may be added in a stoichiometric ratio (1:1), or a slight excess of the isocyanate maybe used, for example between 1.01 fold and 2 fold excess, but typically about 1.01 to about 1.2 fold excess. Typically, the isocyanate is added to a suspension of the carboxamide in toluene, and the resulting mixture is heated until the reaction is determined to be complete. The reaction mixture may be heated at about 10° C. to about 150° C., preferably at about 40° C. to about 120° C. under an inert atmosphere such as nitrogen, or the reaction mixture may be maintained at the refluxing temperature of the mixture. The reaction may be allowed to proceed to completion in about 10 minutes to 24 hours. Preferably, the reaction is heated to reflux until the reaction is complete, over about 6 to 24 hours.

Upon cooling of the reaction mixture, the resulting precipitated acylureas maybe isolated by conventional techniques. Typically, the product is isolated by filtration. The precipitated solid maybe filtered, washed with a solvent or a series of solvents, and isolated without further purification. Preferably, the precipitated acylureas may be washed with a combination of toluene, methanol and then with ether, and the product may be dried under vacuum. If desired, the acylureas may be further purified using conventional techniques, such as by crystallization using conventional methods known in the art. Optionally, acylureas prepared according to this procedure may be converted to the corresponding salts prior to isolation and/or purification, or after crystallization.

Procedure B:

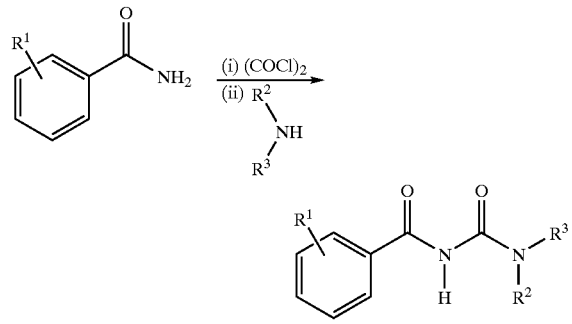

Acylureas may also be prepared from the condensation of an aryl carboxamide with an amine. The carboxamide may be prepared from the corresponding carboxylic acid or may be obtained from commercial sources. Depending on the desired substitution of the amine, optionally, the amine may be substituted where one substituted group is an amine protecting group such that the protecting group may be removed in a subsequent step if desired. In the first step of the process, a carboxamide mixture in a suitable aprotic solvent is treated with a haloformylation reagent to form the corresponding carboxamide carbonylchloride derivative. Typically, the aprotic solvent is dichloromethane, toluene, 2-methyltetrahydrofuran or THF, and the haloformylation reagent is oxalyl chloride. Preferably, the aprotic solvent is THF. Oxalyl chloride is preferably present in an excess, for example between 1.1 to 3.0 equivalents, typically about 1.5 equivalent over the carboxamide. The reaction is generally performed under an inert atmosphere where the mixture is heated to 50° C. to 175° C. for 15 minutes to 24 hours until the reaction is deemed complete. Typically, the reaction is heated to reflux over 2 to 16 hours under nitrogen, and then cooled to room temperature. The solvent is removed in vacuo by rotoevaporation or distillation, and the resulting carboxamide carbonylchloride is then condensed with a primary or secondary amine. Condensation with the amine may be performed by the addition of a solution of the amine in an aprotic solvent, such as THF, under an inert atmosphere, at a temperature between 0° C. and 20° C., preferably between 0° C. and 5° C. If the chloroformylation and the subsequent condensation reaction is performed in the same solvent, the solvent removal step may be eliminated. Preferably, the reaction is performed at 0° C. to 5° C. for 1 to 24 hours, until the reaction is complete. The solvent is removed by concentration under reduced pressure, and the acylurea can be isolated by conventional techniques such as filtration and washing of the crude product with a solvent, followed by drying under vacuum.

Procedure C:

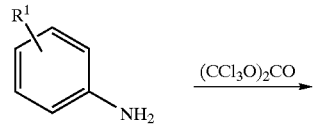

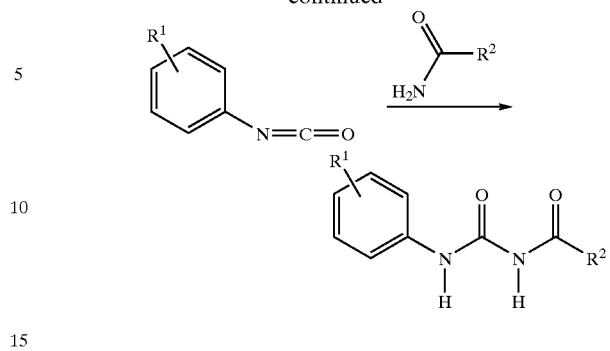

The preparation of the acylureas may also be performed starting with an amine or aniline derivative through a condensation reaction with a phosgene equivalent, followed by a condensation reaction with the carboxamide. Typically, a solution of an aniline or aniline derivative and triphosgene in tetrachloroethane or other suitable organic solvent is combined and stirred at 25° C. to 80° C. under an inert atmosphere for 2 to 12 hours until the reaction is complete. The solvent is removed under reduced pressure and the residue is dissolved in an aprotic solvent, such as toluene, and the resulting mixture is treated with a carboxamide. The mixture is heated to about 50° C. to 150° C., preferably from about 75° C. to 115° C. Preferably, the reaction m is heated to reflux for 2 to 24 hours until the reaction is complete, and allowed to cool to room temperature. The precipitated solid is isolated by conventional techniques such as filtration. The filtered solid is then washed with a suitable solvent or mixtures of solvents. Typically, the solid is washed with toluene, methanol and then ether, and the washed product is dried in vacuo to give the corresponding acylurea.

Procedure D:

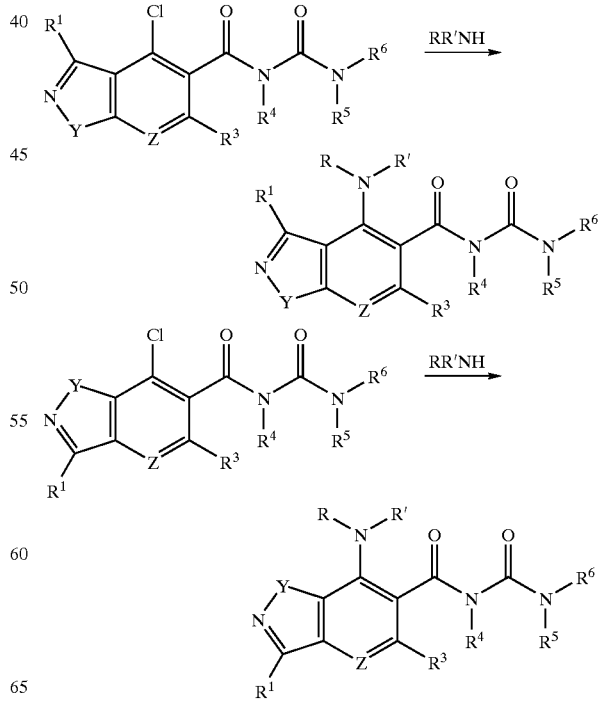

Amine substituted aryl acyl ureas of the present invention may be prepared starting from the corresponding aryl halide acyl ureas by the reaction of the aryl halide with an amine. Preferably, the aryl halide is an aryl chloride, which can be prepared from one or more of the above described procedures or from standard procedures known in the art for preparing these compounds. Typically, the acyl urea is dissolved in an organic solvent or a mixture of suitable organic solvents. Preferably, the organic solvent is tetrahydrofuran. The acyl urea and the amine may be combined as solutions or suspensions, depending on the solubilities of the compounds in the selected solvent or solvent mixtures. The acyl urea and the amine may be added in a stoichiometric ratio (1:1), or a slight excess of the amine maybe used, for example, between 1.01 fold and 20 fold excess, but typically about 1.01 to about 10 fold excess. Typically, the amine is added to the acyl urea in tetrahydrofuran and the resulting mixture is stirred at about 0° C. to refluxing temperatures of the solvent, preferably at about 10° C. to about 50° C., most preferably at about room temperatures under an inert atmosphere such as nitrogen. The reaction mixture is maintained at the reaction temperatures until the reaction proceeds to completion. The reaction may be allowed to proceed to completion in about 10 minutes to 48 hours. Preferably, the reaction is stirred at room temperature for about 5 hours. When the reaction is deemed complete, the resulting product maybe isolated by conventional techniques. Typically, the solvent and excess amine may be removed by evaporation under reduced pressure, and the residue is suspended in a solvent. Preferably, the solvent is water. The suspension or solid may be filtered and washed with water or a suitable solvent, and then isolated and dried using conventional methods.

Procedure E:

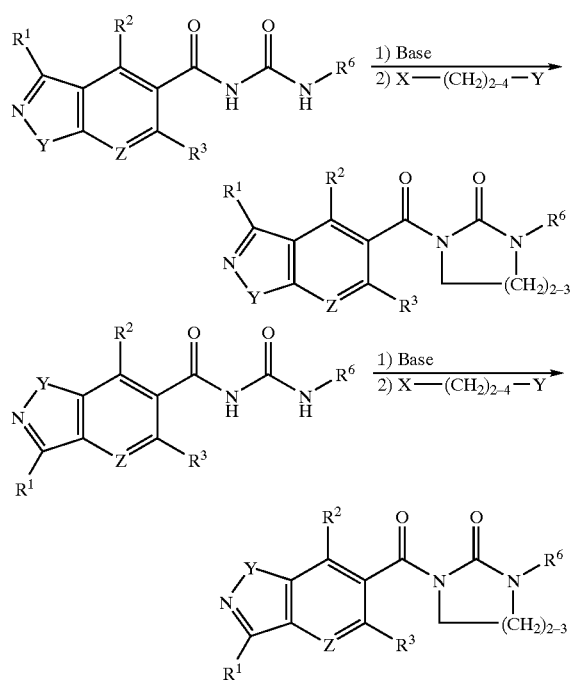

Cyclic acyl ureas of the present invention maybe prepared according to methods known in the art. One method comprises the alkylation of the acyl urea nitrogens with an alkylating agent generically represented above as X—(CH$_2$)$_{2-4}$—Y, where X and Y are leaving groups, and maybe the same or different. Leaving groups known in the art include halides, methanesulfonates, trifluoromethanesulfonates, p-toluenesulfonates, p-bromotoluenesulfonate, p-nitrobenzenesulfonates and the like. Representative alkylating agents include 1,2-dibromoethane, 1,3-dibromoethane, 1,3-dibromopropane, and the corresponding sulfonates and mixed halosulfonates. Typically, the acyl urea is treated with a base in an organic solvent or mixtures of solvents. Preferably, the base is an inorganic base such as sodium hydride, or an organic base such as dimethyl sulfoxide and sodium hydride. Preferably, the solvent is a polar, aprotic solvent such as tetrahydrofuran, dimethylformamide, dimethyl sulfoxide, glycols, or mixtures of such solvents. Typically, a solution or suspension of the acyl urea is slowly added to the base in an organic solvent at about 0° C. to about 25° C., and the resulting mixture is stirred for about 10 minutes to about 5 hours, preferably about 30 minutes. The alkylating agent is added and the mixture is stirred until the reaction is deemed complete. Alkylation of both urea nitrogens may be accomplished in a single step, or may be accomplished sequentially in a two step procedure be exposing the partially alkylated product with the same or different base. The reaction is then quenched with a solvent, preferably water, and the mixture is extracted multiple times with an organic solvent. Preferably, the extracting solvent is dichloromethane. The combined organic extracts are washed with water, dried over anhydrous magnesium sulfate and concentrated under reduced pressure to afford the product, which may be purified using standard conditions known in the art. Purification may be performed by silica gel chromatography in a mixture of organic solvents, such as ethyl acetate and petroleum ether.

Example 1

N-(4-Chloro-1,3-dimethylpyrazolo[5,4-b]pyridin-5-yl)-N-{[(4-chlorophenyl)amino]-carbonyl}carboxamide (39)

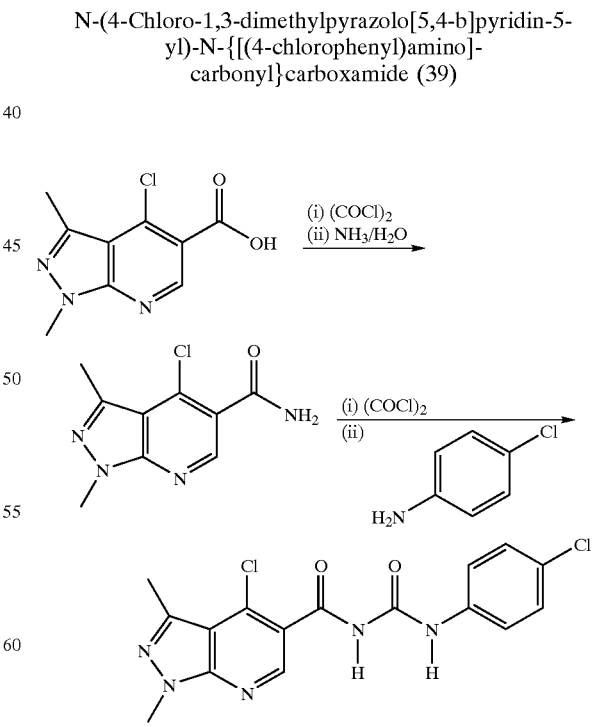

Oxalyl chloride (4.5 mL of a 2M solution in dichloromethane) was added dropwise to a stirred suspension of 4-chloro-1,3-dimethylpyrazolo[5,4-b]pyridine-5-carboxylic acid (0.98 g) in anhydrous dichloromethane (14 mL), followed by 4 drops of N,N-dimethylformamide (DMF). After the evolution of gas subsided, 4 more drops of DMF were added, and this operation was repeated three more times. The mixture was stirred at room temperature for 45 min, filtered to remove trace amounts of insoluble material, and the solvent evaporated under reduced pressure. The residue was dried under high vacuum for 1 h, cooled in an ice-bath, and treated with ammonium hydroxide (28% $NH_3$ in water, 20 mL) in an exothermic reaction. The mixture was stirred at 0° C. for 30 min, and at room temperature for an additional 1 h. The solid was collected by filtration, washed with water, and dried under vacuum to give the carboxamide as a white powder.

Oxalyl chloride (1.4 mL of a 2M solution in dichloromethane) was added dropwise to a suspension of 4-chloro-1,3-dimethylpyrazolo[5,4-b]pyridine-5-carboxamide (0.41 g) in anhydrous dichloromethane (5 mL). The mixture was heated at reflux for 15 h, and cooled to room temperature. The solvent was evaporated under reduced pressure and the residue was dissolved in anhydrous THF (6 mL). An aliquot of this solution (1.5 mL) was added dropwise to an ice-cooled solution of 4-chloroaniline (57 mg) in anhydrous THF (2 mL). The ice-bath was removed and the mixture was stirred at room temperature for 1.5 h. The precipitated solid was collected by filtration, washed with dichloromethane and methanol, and dried under high vacuum to afford N-(4-chloro-1,3-dimethyl-pyrazolo[5,4-b]pyridin-5-yl)-N-{[(4-chlorophenyl)amino]carbonyl}carboxamide as a white powder.

$^1$H NMR (300 MHz, (DMSO-$d_6$) δ 2.68 (s, 3H), 4.02 (s, 3H), 7.42 (d, 2H), J=8.7 Hz), 7.64 (d, 2H), J=8.7 Hz), 8.69 (s, 1H), 10.47 (s, 1H), 11.37 (s, 1H). MS (API-CI) m/z 340, 342, 344.

Example 2

N-{[(3,4-Dichlorophenyl)amino]carbonyl}(1,3-dimethylpyrazolo[5,4-b]pyridin-5-yl) carboxamide (2)

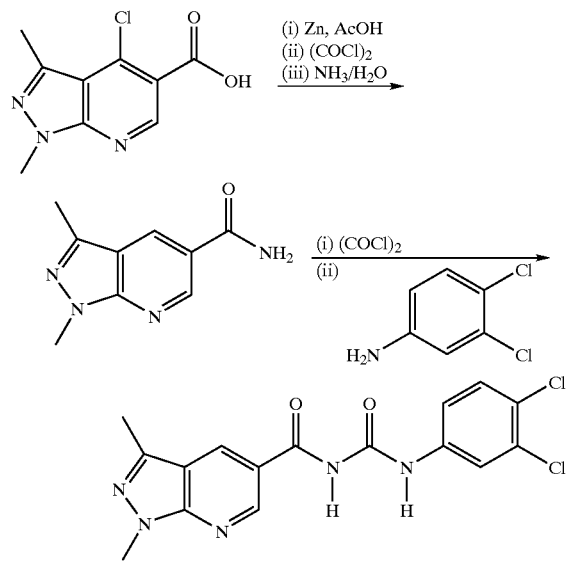

A suspension of 4-chloro-1,3-dimethylpyrazolo[5,4-b]pyridine-5-carboxylic acid (2.00 g) and zinc dust (1.74 g) in acetic acid (40 mL) was heated at 80° C. for 1.5 h. The mixture was cooled to room temperature, slowly poured into an ice-cooled solution of 5N sodium hydroxide (160 mL) and filtered. The filtrate was cooled in an ice-bath and acidified to pH 4 with concentrated hydrochloric acid. The precipitate was filtered, washed with water, and dried under high vacuum. The solid was re-suspended in anhydrous dichloromethane (20 mL) and treated with a 2M solution of oxalyl chloride in dichloromethane (3.6 mL), followed by anhydrous DMF (0.1 mL). The mixture was stirred at room temperature for 1 h, filtered, and the filtrate concentrated under reduced pressure. The residue was cooled in an ice-bath and slowly treated with 28% ammonium hydroxide solution. The suspension was removed from the ice-bath, stirred at room temperature for 1 h, and filtered. The solid was washed with water and dried under high vacuum to produce 1,3-dimethylpyrazolo[5,4-b]pyridine-5-carboxamide as an off-white solid. A suspension of this carboxamide (0.13 g) in anhydrous dichloromethane (5 mL) was treated with a 2M solution of oxalyl chloride also in dichloromethane (0.5 mL) and the mixture heated at gentle reflux for 15 h. The solvent was removed under reduced pressure and the residue dissolved in anhydrous THF (1.2 mL). An aliquot of this solution (0.4 mL) was added to an ice-cooled solution of 3,4-dichloroaniline (36 mg) in anhydrous THF (0.7 mL). The ice-bath was removed and the mixture stirred at room temperature for 1 h. The precipitated solid was collected by filtration, washed with dichloromethane and MeOH, and dried under high vacuum to give the title compound as a white solid.

$^1$H NMR (DMSO-$d_6$) δ 2.56 (s, 3H), 4.02 (s, 3H), 7.56–7.63 (m, 2H), 8.03 (d, J=2.2 Hz, 1H), 8.99 (d, J=2.0 Hz, 1H), 9.08 (d, J=2.0 Hz, 1H), 10.92 (s, 1H), 11.28 (s, 1H). MS (ESI) m/z 376, 378, 380.

Example 3

Ethyl 2-[4-({[(1,3-dimethypyrazolo[5,4-b]pyridin-5-yl)carbonylamino]carbonyl}-amino)-2-(triflouromethyl)phenoxy]acetate (34)

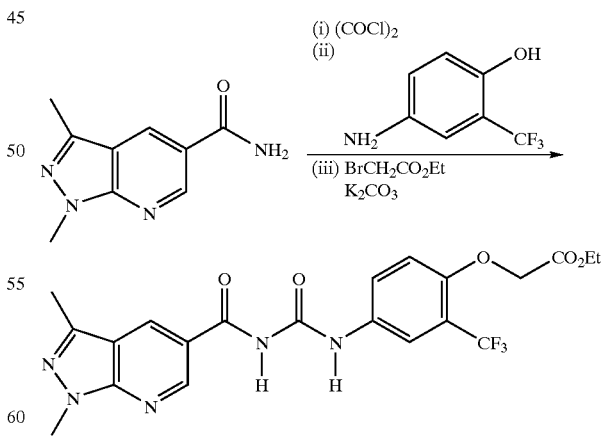

1,3-Dimethylpyrazolo[5,4-b]pyridine-5-carboxamide (0.35 g) was suspended in anhydrous dichloromethane (10 mL) and treated with a 2M solution of oxalyl chloride in dichloromethane (1.8 mL). The suspension was heated at gentle reflux for 15 h, cooled to room temperature, and the solvent removed under reduced pressure. The residue was dissolved in anhydrous THF (7 mL). An aliquot of this solution (2 mL) was added to an ice-cooled solution of 4-amino-2-(trifluoromethyl)phenol (93 mg) in THF (0.5 mL). The ice-bath was removed and the reaction mixture stirred at 25° C., for 1 h. The precipitated solid was collected by filtration, washed with dichloromethane and dried under high vacuum. The solid was re-suspended in acetone-DMF (8 mL:0.8 mL) and treated with potassium carbonate (0.18 g) and ethyl bromoacetate (0.15 mL). The suspension was heated at reflux for 2 h, cooled to room temperature, and concentrated under reduced pressure. The residue was treated with water (3 mL), and the resulting solids were filtered, washed with water and acetone, and dried under high vacuum to give the title compound as a white solid.

$^1$H NMR (DMSO-$d_6$) δ 1.19–1.24 (t, J=7.1 Hz, 3H), 2.58 (s, 3H), 3.99 (s, 3H), 4.14–4.21 (q, J=7.1 Hz, 2H), 4.86 (s, 2H), 7.03 (d, J=9.7 Hz, 1H), 7.52–7.60 (dd, J=2.4, 8.8 Hz, 1H), 8.09 (d, J=2.4 Hz, 1H), 8.75 (d, J=1.6 Hz, 1H), 9.22 (d, J=1.6 Hz, 1H), 12.12 (s, 1H). MS (ESI) m/z 480.

Example 4

Sodium 2-[4-({[(1,3-Dimethypyrazolo[5,4-b]pyridin-5-yl)carbonylamino]carbonyl}-amino-2-(trifluoromethyl)phenoxy]acetate (35)

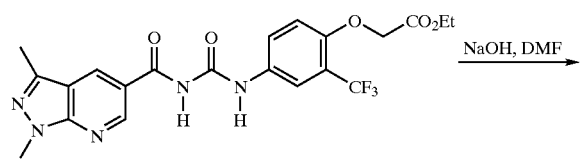

NaOH, DMF

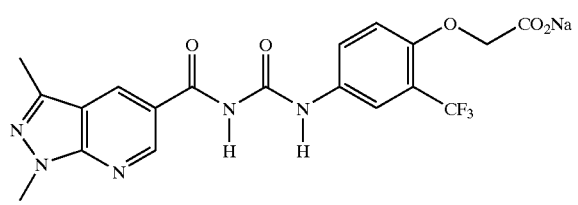

A solution of ethyl 2-[4-({[(1,3-dimethypyrazolo[5,4-b]pyridin-5-yl)carbonylamino]carbonyl}-amino)-2-(trifluoromethyl)phenoxy]acetate (0.11 g) in DMF (3 mL) was treated with 5N sodium hydroxide solution (1.6 mL). The mixture was stirred at room temperature for 1.25 h, and then concentrated under reduced pressure. The residue was taken up in water (4 mL), filtered, and the filtrate was cooled in an ice-bath and acidified to pH 4 with concentrated hydrochloric acid. The precipitated solid was collected by filtration, washed with water, and dried under high vacuum. A portion of this material was suspended in water (5 mL) and treated with 5N sodium hydroxide solution (27 μL). The mixture was sonicated, filtered, and the filtrate lyophilized to yield the title compound.

$^1$H NMR (DMSO-$d_6$) δ 2.53 (s, 3H), 3.99 (s, 3H), 4.17 (s, 2H), 6.85 (d, J=8.8 Hz, 1H), 7.44–7.47 (br d, J=8.8 Hz, 1H), 8.03 (d, J=2.1 Hz, 1H), 8.52 (s, 1H), 8.79 (d, J=1.6 Hz, 1H), 9.23 (d, J=1.6 Hz, 1H), 11.50 (br s, 1H). MS (ESI) m/z 450.

Example 5

N-({[4-fluoro-3-(trifluoromethyl)phenyl]amino}carbonyl)(4-hydroxy-1,3-dimethylpyrazolo[5,4-b]pyridin-5-yl)carboxamide (43)

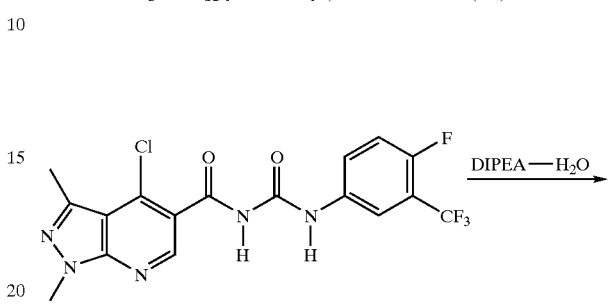

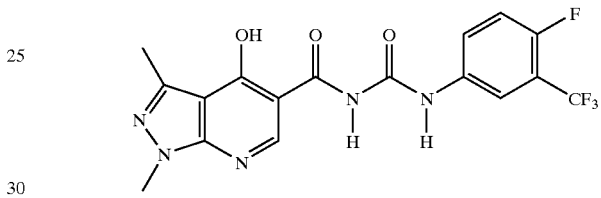

A suspension of (4-chloro-1,3-dimethylpyrazolo[5,4-b]pyridin-5-yl)-N-({[4-fluoro-3-(trifluoromethyl)phenyl]amino}carbonyl)carboxamide (0.050 g) in THF (5 mL) was dissolved in a 1:3 mixture of N,N-diisopropylethylamine (DIPEA) and water (4 mL). The solution was stirred at room temperature for 24 h, concentrated, and the residue purified by column chromatography on silica-gel eluting with 3:1 EtOAc-MeOH to give the title compound as a white powder.

$^1$H NMR (DMSO-$d_6$) δ 2.46 (s, 3H, 3.75 (s, 3H), 7.45 (dd, J=9.9, 9.9 Hz, 1H), 7.81 (m, 1H), 8.11 (dd, J=6.6, 2.6 Hz, 1H), 8.58 (s, 1H), 11.51 (br s, 1H). MS (ESI) m/z 410.

Example 6

(1,3-Dimethyl-4-morpholin-4-ylpyrazolo[5,4-b]pyridin-5-yl)-N-({[4-fluoro-3-(trifluoromethyl)phenyl]amino}carbonyl)carboxamide (65)

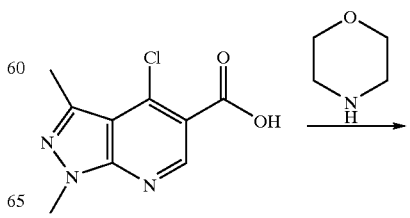

-continued

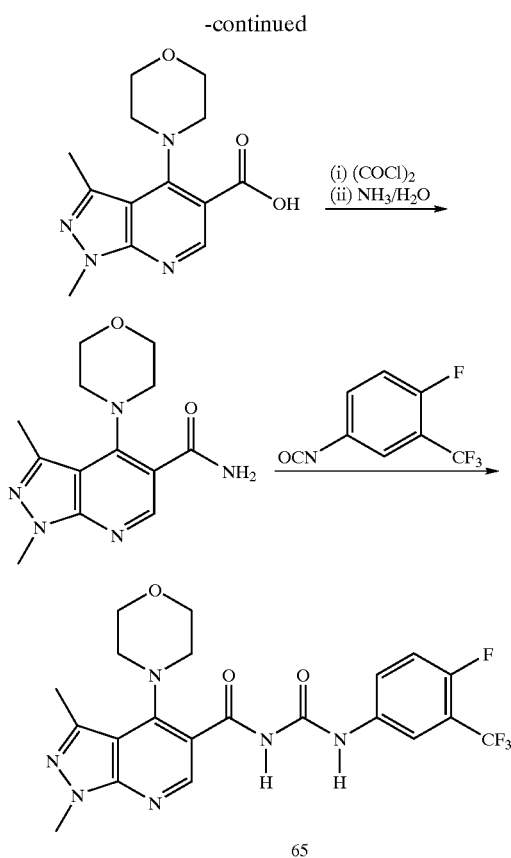

A solution of 4-chloro-1,3-dimethylpyrazolo[5,4-b]pyridine-5-carboxylic acid (450 mg) and morpholine (870 mg) in DMF (15 mL) was stirred at room temperature for 5 h, and then concentrated under reduced pressure. The residue was treated with water (10 mL), and the resulting solid was filtered, washed with water, and dried under high vacuum. The solid was suspended in anhydrous dichloromethane (20 mL) and treated with oxalyl chloride (1.0 mL) and anhydrous DMF (0.1 mL). The mixture was stirred at room temperature for 1 h, filtered, and the filtrate was concentrated under reduced pressure. The residue was cooled in an ice-bath and slowly treated with a saturated solution of ammonia in THF (20 mL). The suspension was removed from the ice-bath, stirred at room temperature for 1 h, and filtered. The solid was washed with water and dried under high vacuum to give 1,3-dimethyl-4-morpholin-4-ylpyrazolo[5,4-b]pyridine-5-carboxamide as a white powder. A portion of this material (0.33 g) was dissolved in hot toluene (30 mL) and azeotropic for 1 h. The solution was cooled to room temperature and treated with 4-fluoro-3-(trifluoromethyl)phenylisocyanate (0.27 g). The mixture was refluxed for 16 h and then cooled to room temperature. The precipitated solid was filtered, washed with toluene, and dried under high vacuum to give the title compound as a white powder.

$^1$H NMR (DMSO-d$_6$) δ 2.62 (s, 3H), 3.27 (m, 4H), 3.80 (m, 4H), 3.93 (s, 3H), 7.50 (dd, J=9.9, 9.9 Hz, 1H), 7.92 (m, 1H), 8.13 (dd, J=6.6, 2.6 Hz, 1H), 8.38 (s, 1H), 10.72 (s, 1H), 11.34 (s, 1H). MS (ESI) m/z 479.

Example 7

(4-{[2-(Dimethylamino)ethyl]amino}-1,3-dimethylpyrazolo[5,4-b]pyridin-5-yl)-N-({[4-fluoro-3-(trifluoromethyl)phenyl]amino}carbonyl)carboxamide (45)

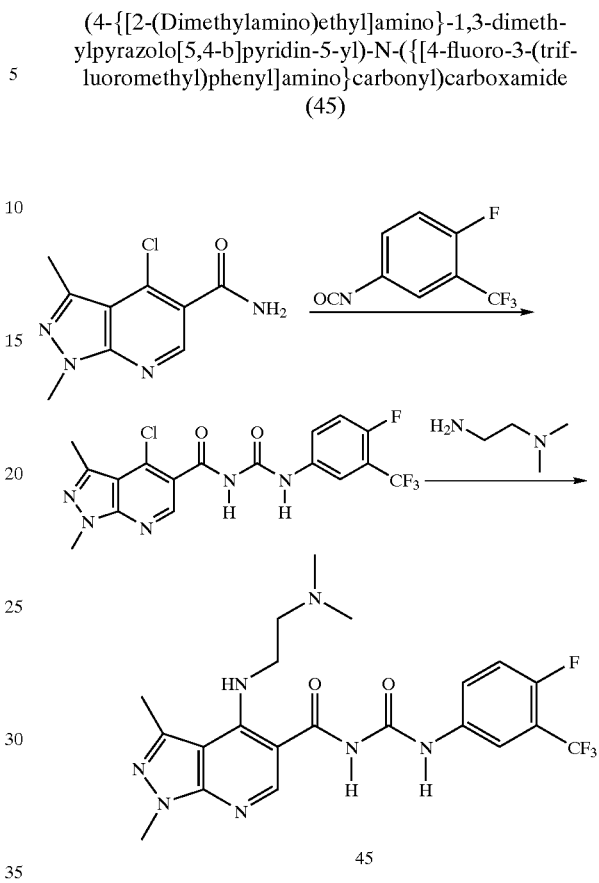

4-Chloro1,3-dimethylpyrazolo[5,4-b]pyridine-5-carboxamide (0.10 g) was dissolved in hot toluene (30 mL) and azeotroped for 1 h. The solution was cooled to room temperature and reacted with 4-fluoro-3-(trifluoromethyl)phenylisocyanate (0.10 g). The mixture was refluxed for 16 h and then cooled to room temperature. The precipitated solid was filtered, washed with methanol, and dried under high vacuum to give (4-chloro-1,3-dimethylpyrazolo[5,4-b]pyridin-5-yl)-N-({[4-fluoro-3-(trifluoromethyl)phenyl]amino}carbonyl)carboxamide as a white powder. A portion of this material (0.050 g) was dissolved in THF (10 mL) and reacted with (2-aminoethyl)dimethylamine (0.10 g). The mixture was stirred at room temperature for 5 h, and then concentrated under reduced pressure. The residue was treated with water (10 mL), and the resulting solid was filtered, washed with water, and dried under high vacuum. A portion of this material was suspended in water (5 mL) and treated with 1N hydrochloric acid solution (100 μL). The mixture was sonicated, filtered, and the filtrate lyophilized to give (4-{[2-(dimethylamino)ethyl]amino}-1,3-dimethylpyrazolo[5,4-b]pyridin-5-yl)-N-({[4-fluoro-3-(trifluoromethyl)phenyl]amino}carbonyl)carboxamide hydrochloride as a white powder.

$^1$H NMR (DMSO-d$_6$) δ 2.22 (s, 6H), 2.53 (t, J=5.8 Hz, 2H), 2.61 (s, 3H), 3.62 (t, J=5.8 Hz, 2H), 3.86 (s, 3H), 7.50 (dd, J=10.3, 9.5 Hz, 1H), 7.76 (br s, 1H), 7.86 (m, 1H), 8.09 (dd, J=6.6, 2.6 Hz, 1H), 8.40 (s, 1H), 10.74 (s, 1H), 10.97 (br s, 1H). MS (ESI) m/z 480.

The following additional compounds were prepared by the foregoing procedures:

[4-(Dimethylamino)-1,3-dimethylpyrazolo[5,4-b]pyridin-5-yl]-({[4-fluoro-3-(trifluoromethyl)phenyl]amino}carbonyl)carboxamide (44).

$^1$H NMR (DMSO-$d_6$) δ 2.59 (s, 3H), 3.04 (s, 6H), 3.90 (s, 3H), 7.50 (dd, J=9.9, 9.9 Hz, 1H), 7.90 (m, 1H) 8.11 (dd, J=3.6, 2.6 Hz, 1H), 8.29 (s, 1H), 10.79 (s, 1H), 11.18 (s, 1H). MS (ESI) m/z 437.

(4-{[2-(Dimethylamino)ethyl]amino}-1,3-dimethylpyrazolo[5,4-b]pyridin-5-yl)-N-({[4-fluoro-3-(trifluoromethyl)phenyl]amino}carbonyl)carboxamide hydrochloride (46).

$^1$H NMR (DMSO-$d_6$) δ 2.69 (s, 3H), 2.79 (d, J=4.4 Hz, 6H), 3.40 (m, 2H), 3.83 (m, 2H), 3.89 (s, 3H), 7.52 (dd, J=9.9, 9.9 Hz, 1H), 7.65 (br s, 1H), 7.88 (m, 1H), 8.08 (dd, J=6.6, 2.6 Hz 1H), 8.47 (s, 1H), 10.67 (s, 1H), 10.73 (s, 1H), 11.13 (s, 1H).

(4-{[2-(Dimethylamino)ethyl]methylamino}-1,3-dimethylpyrazolo[5,4-b]pyridin-5-yl)-N-({[4-fluoro-3-(trifluoromethyl)phenyl]amino}carbonyl)carboxamide (47).

$^1$H NMR (DMSO-$d_6$) δ 2.01 (s, 6H), 2.53 (t, J=5.8 Hz, 2H), 2.59 (s, 3H), 3.04 (s, 3H), 3.63 (t, J=5.8 Hz, 2H), 3.92 (s, 3H), 7.50 (dd, J=9.9, 9.5 Hz, 1H), 7.90 (m, 1H), 8.14 (dd, J=3.6, 2.6 Hz, 1H), 8.38 (s, 1H), 10.99 (s, 1H), 11.99 (s, 1H). MS (ESI) m/z 494.

(4-{[3-(Dimethylamino)propyl]amino}-1,3-dimethylpyrazolo[5,4-b]pyridin-5-yl)-N-({[4-fluoro-3-(trifluoromethyl)phenyl]amino}carbonyl)carboxamide (49).

$^1$H NMR (DMSO-$d_6$) δ 1.77 (m, 2H), 2.14 (s, 6H), 2.36 (t, J=6.6 Hz, 2H), 2.59 (s, 3H), 3.45 (t, J=6.6 Hz, 2H), 3.86 (s, 3H), 7.50 (dd, J=9.9, 9.5 Hz, 1H), 7.85 (m, 1H), 8.08 (m, 1H), 8.41 (s, 1H), 10.78 (br s, 1H). MS (ESI) m/z 494.

{4-[Bis(2-hydroxyethyl)amino]-1,3-dimethylpyrazolo[5,4-b]pyridin-5-yl}-N-({[4-fluoro-3-(trifluoromethyl)phenyl]amino}carbonyl)carboxamide (51).

$^1$H NMR (DMSO-$d_6$) δ 2.59 (s, 3H), 3.52 (m, 4H), 3.62 (m, 4H), 3.92 (s, 3H), 5.12 (br s, 2H), 7.53 (dd, J=9.9, 8.9 Hz, 1H), 7.90 (m, 1H), 8.20 (dd, J=6.6, 2.6 Hz, 1H), 8.36 (s, 1H), 10.86 (s, 1H), 11.31 (br s, 1H). MS (ESI) m/z 497.

{1,3-Dimethyl-4-[methyl(1-methylpyrrolidin-3-yl)amino]pyrazolo[5,4-b]pyridin-5-yl}-N-({[4-fluoro-3-(trifluoromethyl)phenyl]amino}carbonyl)carboxamide (53).

$^1$H NMR (DMSO-$d_6$) δ 1.97 (m, 2H), 2.22 (s, 3H), 2.28 (m, 1H), 2.54 (m, 1H), 2.58 (s, 3H), 2.60–2.80 (m, 2H), 2.90 (s, 3H), 3.93 (s, 3H), 4.24 (m, 1H), 7.50 (dd, J=10.3, 9.5 Hz, 1H), 7.90 (m, 1H), 8.12 (dd, J=6.6, 2.6 Hz, 1H), 8.41 (s, 1H), 10.7 (br s, 1H), 11.4 (br s, 1H). MS (ESI) m/z 506.

{4-[(4-Aminocyclohexyl)amino]-1,3-dimethylpyrazolo[5,4-b]pyridin-5-yl}-N-({[4-fluoro-3-(trifluoromethyl)phenyl]amino}carbonyl)carboxamide (55).

$^1$H NMR (DMSO-$d_6$) δ 1.64–1.83 (m, 8H), 2.63 (s, 3H), 3.18 (m, 1H), 3.88 (s, 3H), 4.08 (m, 1H), 7.52 (m, 1H), 7.88 (m, 1H), 8.10 (m, 1H), 8.57 (s, 1H), 10.6 (br s, 1H), 10.9 (br s, 1H). MS (ESI) m/s 506.

{1,3-Dimethyl-4-[(perhydropyrrolizin-7a-ylmethyl)amino]pyrazolo[5,4-b]pyridin-5-yl}-N-({[4-fluoro-3-(trifluoromethyl)phenyl]amino}carbonyl)carboxamide (57).

$^1$H NMR (DMSO-$d_6$) δ 1.59–1.81 (m, 8H), 2.59 (s, 3H), 2.85–3.03 (m, 2H), 2.93 (d, J=6.2 Hz, 2H), 3.85 (s, 3H), 7.48 (dd, J=9.9, 9.5 Hz, 1H), 7.59 (br s, 1H), 7.82 (m, 1H), 8.10 (dd, J=6.2, 2.6 Hz, 1H), 8.50 (s, 1H), 10.9 (br s, 1H). MS (ESI) m/z 532.

{1,3-Dimethyl-4-[(2-perhydropyrrolizin-7a-ylethyl)amino]pyrazolo[5,4-b]pyridin-5-yl}-N-{[4-fluoro-3-(trifluoromethyl)phenyl]amino}carbonyl)carboxamide (59).

$^1$H NMR (DMSO-$d_6$) δ 1.57–1.78 (m, 10H), 2.57 (m, 2H), 2.60 (s, 3H), 2.90 (m, 2H), 3.33 (t, J=6.2 Hz, 2H), 3.84 (s, 3H), 7.50 (dd, J=9.9, 9.5 Hz, 1H), 7.87 (m, 1H), 8.12 (dd, J=6.2, 2.6 Hz, 1H), 8.28 (s, 1H), 10.82 (br s, 1H), 11.52 (s, 1H). MS (ESI) m/z 546.

{1,3-Dimethyl-4-[(2-perhydropyrrolizin-7a-ylethyl)amino]pyrazolo[5,4-b]pyridin-5-yl}-N-({[4-fluoro-3-(trifluoromethyl)phenyl]amino}carbonyl)carboxamide hydrochloride (60).

$^1$H NMR (DMSO-$d_6$) δ 1.89–2.18 (m, 10H), 2.65 (s, 3H), 3.08 (m, 2H), 3.59 (m, 2H), 3.90 (s, 3H), 7.51 (dd, J=9.9, 9.5 Hz, 1H), 7.87 (m, 1H), 8.01 (br s, 1H), 8.07 (dd, J=6.6, 2.6 Hz, 1H), 8.50 (s, 1H), 10.58 (br s, 1H), 11.71 (s, 1H), 11.11 (s, 1H).

(1,3-Dimethyl-4-piperidylpyrazolo[5,4-b]pyridin-5-yl)-N-({[4-fluoro-3-(trifluoromethyl)phenyl]amino}carbonyl)carboxamide (64).

$^1$H NMR (DMSO-$d_6$) δ 1.62 (m, 2H), 1.71 (m, 4H), 2.62 (s, 3H), 3.24 (m, 4H), 3.92 (s, 3H), 7.50 (dd, J=9.9, 9.5 Hz, 1H), 7.92 (m, 1H), 8.12 (dd, J=6.2, 2.6 Hz, 1H), 8.35 (s, 1H), 10.71 s, 1H), 11.31 (s, 1H). MS (ESI) m/z 477.

(1,3-Dimethyl-4-piperazinylpyrazololo[5,4-b]pyridin-5-yl)-N-({[4-fluoro-3-(trifluoromethyl)phenyl]amino}carbonyl)carboxamide (66).

$^1$H NMR (DMSO-$d_6$) δ 2.62 (s, 3H), 2.93 (m, 4H), 3.23 (m, 4H), 3.92 (s, 3H), 7.51 (dd, J=9.5, 9.5 Hz, 1H), 7.90 (m, 1H), 8.12 (dd, J=6.2, 2.6 Hz, 1H), 8.36 (s, 1H), 10.7 (br s, 1H), 11.3 (br s, 1H). MS (ESI) m/z 478.

[1,3-Dimethyl-4-(4-methylpiperazinyl)pyrazolo[5,4-b]pyridin-5-yl]-N-({[4-fluoro-3-(trifluoromethyl)phenyl]amino}carbonyl)carboxamide (84).

$^1$H NMR (DMSO-$d_6$) δ 2.32 (s, 3H), 2.55 (m, 4H), 2.62 (s, 3H), 3.29 (m, 4H), 3.93 (s, 3H), 7.51 (dd, J=9.9, 9.9 Hz, 1H), 7.91 (m, 1H), 8.12 (dd, J=6.2, 2.6 Hz, 1H), 8.37 (s, 1H), 11.32 (s, 1H). MS (ESI) m/z 492.

[1,3-Dimethyl-4-(4-methylpiperazinyl)pyrazolo[5,4-b]pyridin-5-yl]-N-({[4-fluoro-3-(trifluoromethyl)phenyl]amino}carbonyl)carboxamide hydrochloride (85).

$^1$H NMR (DMSO-$d_6$) δ 2.65 (s, 3H), 2.86 (d, J=4.4 Hz, 3H), 3.31 (m, 2H), 3.51 (m, 6H), 3.95 (s, 3H), 7.52 (dd, J=9.9, 9.9 Hz, 1H), 7.88 (m, 1H), 8.11 (m, 1H), 8.44 (s, 1H), 10.48 (br, s 1H), 10.74 (s, 1H), 11.38 (s, 1H).

[4-(4-Ethylpiperazinyl)-1,3-dimethylpyrazolo[5,4-b]pyridin-5-yl]-N-({[4-fluoro-3-(trifluoromethyl)phenyl]amino}carbonyl)carboxamide (99).

$^1$H NMR (DMSO-$d_6$) δ 1.03 (t, J=6.9 Hz, 3H), 2.41 (q, J=6.9 Hz, 2H), 2.57 (m, 4H), 2.62 (s, 3H), 3.31 (m, 4H), 3.93 (s, 3H), 7.50 (dd, J=9.9, 9.9 Hz, 1H), 7.91 (m, 1H), 8.13 (dd, J=6.2, 2.6 Hz, 1H), 8.35 (s, 1H), 10.72 (s, 1H), 11.31 (s, 1H). MS (ESI) m/z 506.

[4-(4-Ethylpiperazinyl)-1,3-dimethylpyrazolo[5,4-b]pyridin-5-yl]-N-({[4-fluoro-3-(trifluoromethyl)phenyl]amino}carbonyl)carboxamide hydrochloride (100).

$^1$H NMR (DMSO-$d_6$) δ 1.28 (d, J=7.3 Hz, 3H), 2.65 (s, 3H), 3.17–3.35 (m, 4H), 3.45–3.61 (m, 6H), 3.95 (s, 3H), 7.52 (dd, J=9.9, 9.5 Hz, 1H), 7.89 (m, 1H), 8.11 (dd, J=6.2, 2.6 Hz, 1H), 8.44 (s, 1H), 10.29 (br s, 1H), 10.74 (s, 1H), 11.39 (s, 1H).

N-({[4-Fluoro-3-(trifluoromethyl)phenyl]amino}carbonyl){4-[4-(2-hydroxyethyl)piperazinyl]-1,3-dimethylpyrazolo[5,4-b]pyridin-5-yl}carboxamide (101).

$^1$H NMR (DMSO-$d_6$) δ 2.47 (t, J=5.9 Hz, 2H), 2.62 (s, 3H), 2.63 (m, 4H), 3.28 (m, 4H), 3.53 (m, 2H), 3.92 (s, 3H), 4.38 (br s, 1H), 7.51 (dd, J=9.9, 9.5 Hz, 1H), 8.13 (dd, J=6.2, 2.6 Hz, 1H), 8.35 (s, 1H), 10.7 (br s, 1H), 11.3 (br s, 1H). MS (ESI) m/z 522.

[1,3-Dimethyl-4-(4-phenylpiperazinyl)pyrazolo[5,4-b]pyridin-5-yl]-N-({[4-fluoro-3-(trifluoromethyl)phenyl]amino}carbonyl)carboxamide (103).

¹H NMR (DMSO-d₆) δ 2.66 (s, 3H), 3.36 (m, 4H), 3.43 (m, 4H), 3.94 (s, 3H), 6.81 (t, J=7.3 Hz, 1H), 7.01 (d, J=8.1 Hz, 1H), 7.23 (dd, J=8.1, 7.3 Hz, 1H), 7.49 (dd, J=9.9, 9.5 Hz, 1H), 7.91 (m, 1H), 8.12 (dd, J=6.3, 2.6 Hz, 1H), 8.40 (s, 1H), 10.72 (s, 1H), 11.38 (br s, 1H). MS (ESI) m/z 554.

{1,3-Dimethyl-4-[4-benzylpiperazinyl]pyrazolo[5,4-b]pyridin-5-yl}-N-({[4-fluoro-3-(trifluoromethyl)phenyl]amino}carbonyl)carboxamide (104).

¹H NMR (DMSO-d₆) δ 2.59 (m, 3H), 2.61 (s, 4H), 3.29 (m, 4H), 3.55 (s, 2H), 3.92 (s, 3H), 7.24–7.33 (m, 5H), 7.50 (dd, J=9.9, 9.5 Hz, 1H), 7.92 (m, 1H), 8.13 (dd, J=6.2, 2.6 Hz, 1H), 8.35 (s, 1H), 10.69 (s, 1H), 11.29 (s, 1H). MS (ESI) m/z 568.

4-Amino-1-{5-[N-({[4-fluoro-3-(trifluoromethyl)phenyl]amino}carbonyl)carbamoyl]-1,3-dimethylpyrazolo[5,4-b]pyridin-4-yl}pyridinium chloride (106).

¹H NMR (DMSO-d₆) δ 2.17 (s, 3H), 4.10 (s, 3H), 7.04 (d, J=7.3 Hz, 2H), 7.48 (dd, J=9.9,9.5 Hz, 1H), 7.82 (m, 1H), 8.01 (dd, J=6.6, 2.6 Hz, 1H), 8.36 (d, J=7.3 Hz, 2H), 8.80 (br s, 2H), 9.06 (s, 1H), 10.4 (br s, 1H), 11.4 (br s, 1H). MS (ESI) m/z 486.

[1,3-Dimethyl-4-(4-methyl(1,4-diazaperhydroepinyl))pyrazolo[5,4-b]pyridin-5-yl]-N-({[4-fluoro-3-(trifluoromethyl)phenyl]amino}carbonyl)carboxamide (107).

¹H NMR (DMSO-d₆) δ 1.92 (m, 2H), 2.30 (s, 3H), 2.63 (s, 3H), 2.70 (m, 4H), 3.54 (m, 4H), 3.91 (s, 3H), 7.50 (dd, J=9.9, 9.5 Hz, 1H), 7.91 (m, 1H), 8.12 (m, 1H), 8.36 (s, 1H), 10.75 (s, 1H), 11.22 (s, 1H). MS (ESI) m/z 506.

[1,3-Dimethyl-4-(4-methyl(1,4-diazaperhydroepinyl))pyrazolo[5,4-b]pyridin-5-yl]-N-({[4-fluoro-3-(trifluoromethyl)phenyl]amino}carbonyl)carboxamide hydrochloride (108).

¹H NMR (DMSO-d₆) δ 2.15–2.32 (m, 2H), 2.65 (s, 3H), 2.83 (d, J=4.8 Hz, 3H), 3.22–3.30(m, 1H), 3.52–3.69 (m, 3H), 3.91–3.97 (m, 1H), 3.94 (s, 3H), 7.52 (dd, J=9.9, 9.5 Hz, 1H), 7.92 (m, 1H), 8.13 (dd, J=6.2, 2.6 Hz, 1H), 8.45 (s, 1H), 10.74 (br s, 1H), 10.76 (s, 1H), 11.30 (s, 1H).

Example 8

(6-{[2-(Dimethylamino)ethyl]methylamino}-1,3-dimethylpyrazolo[5,4-b]pyridin-5-yl)-({[4-fluoro-3-(trifluoromethyl)phenyl]amino}carbonyl)carboxamide hydrochloride (116)

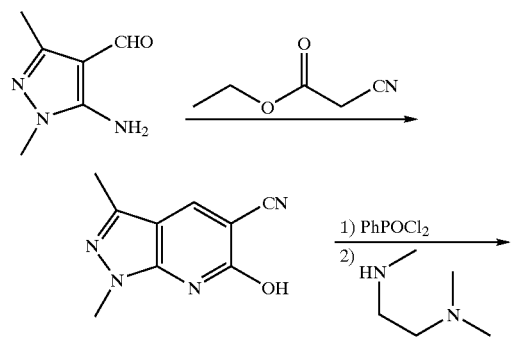

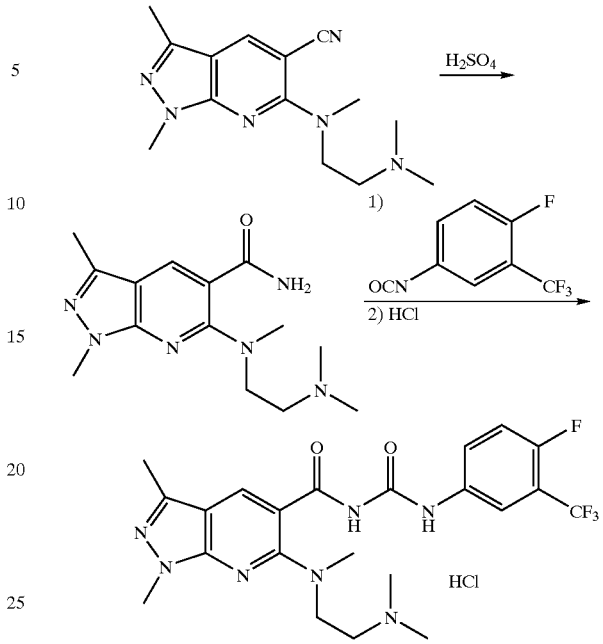

A solution of 5-amino-1,3-dimethylpyrazole-4-carbaldehyde (6.15 g) in ethyl cyanoacetate (10 mL) was stirred at 185° C. for 3 hrs. The reaction mixture was allowed to cool to room temperature. The precipitated solid was filtered, washed with ethyl acetate, and dried under high vacuum to give 6-hydroxy-1,3-dimethylpyrazolo[5,4-b]pyridin-5-carbonitrile as a white powder.

A portion of this material (2.18 g) was dissolved in phenylphosphonic dichloride (10 mL) and stirred at 150° C. for 17 hrs. The solution was cooled to room temperature and poured into water, extracted with ethyl acetate, washed with saturated NaHCO₃ solution, and dried over Na₂SO₄. Evaporation of the solvent under reduced pressure produced a white solid. This material (2.16 g) was dissolved in tetrahydrofuran (50 mL), dimethylaminoethylmethylamine (10.6 mL) was added at room temperature, and the m was heated at reflux for 20 hrs. The reaction mixture was cooled to room temperature, extracted with ethyl acetate. The extract was dried over Na₂SO₄, and evaporated under reduced pressure to give 6-{[2-(dimethylamino)ethyl]methylamino}-1,3-dimethyl-pyrazolo[5,4-]pyridine[5,4-]pyridine-5-carbonitrile as a brown oil. This material (2.96 g) was dissolved in concentrated H₂SO₄ (10 mL). The mixture was stirred at 60° C. for 15 hrs. The reaction mixture was neutralized with saturated NaHCO₃ solution and extracted with dichloromethane. The extract was washed with NaCl solution, dried over Na₂SO₄, and evaporated under reduced pressure. The residue was purified by the recrystalization from the mixture of ethyl acetate and hexane to give 6-{[2-(dimethylamino)ethyl]methylamino}-1,3-dimethylpyrazolo[5,4-b]pyridine-5-carboxamide as a white solid. A portion of this material (0.150 g) was dissolved in hot toluene (20 mL) and azeotroped for 2 hrs. The solution was cooled to room temperature and reacted with 4-fluoro- 3-(trifluoromethyl)phenylisocyanate (0.180 g). The mixture was refluxed for 2 days and then cooled to room temperature. The solvent was evaporated under reduced pressure. The residue was purified with the column chromatography(ethyl acetate) to give the acylurea as a white solid. A portion of this material (52 mg)

was dissolved in tetrahydrofuran (1.0 mL) and treated with 1N hydrochloric acid solution (1.0 mL). This mixture was lyophilized to give (6-{[2-(dimethylamino)ethyl]methylamino}-1,3-dimethylpyrazolo[5,4-b]pyridin-5-yl)-N-({[4-fluoro-3-(trifluoromethyl)phenyl]amino}carbonyl)-carboxamide hydrochloride as a white solid.

$^1$H NMR (DMSO-d$_6$) δ 2.17 (s, 6H), 2.41 (s, 3H), 2.53 (t, J=6.4 Hz, 2H), 2.98 (s, 3H), 3.64 (t, J=6.4 Hz, 2H), 3.82 (s, 3H), 7.49 (m, 1H), 7.87 (m, 1H), 8.10 (m, 1H), 8.26 (s, 1H), 10.82 (br s, 1H).

Example 9

{6-[2-(Diethylamino)ethoxy]-1,3-dimethylpyrazolo[5,4-b]pyridin-5-yl}-N-({[4-fluoro-3-(trifluoromethyl)phenyl]amino}carbonyl)carboxamide hydrochloride (120)

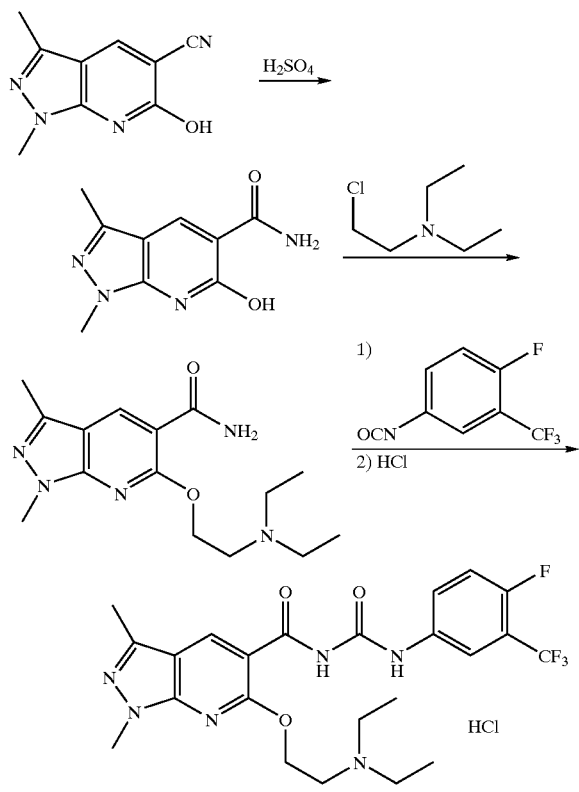

6-Hydroxy-1,3-dimethylpyrazolo[5,4-b]pyridine-5-carbonitrile (0.911 g) was dissolved in concentrated H$_2$SO$_4$ (3.0 mL) and stirred at 40° C. for 24 hrs. The solution was poured into ice-water and the precipitated solid was filtered, washed with water, and dried under high vacuum to give 6-hydroxy-1,3-dimethylpyrazolo[5,4-b]pyridin-5-carboxamide as a white solid. A portion of this material (0.122 g) was dissolved in DMF (2.0 mL). 2-Chlorotriethylamine hydrochloride (0.192 g) and potassium carbonate (0.304 g) were added to the solution. The reaction mixture was stirred at 60° C. for 18 h. The reaction mixture was poured into water, extracted with ethyl acetate. The extract was washed with saturated NaHCO$_3$ solution and the brine, and dried over Na$_2$SO$_4$. The extract was evaporated under reduced pressure to give 6-[2-(diethylamino)ethoxy]-1,3-dimethyl-pyrazolo[5,4-b]pyridine-5-carboxamide as a white solid. A portion of this material (0.059 g) was dissolved in hot toluene (10 mL) and azeotroped for 2 hrs. The solution was cooled to room temperature. 4-Fluoro-3-(trifluoromethyl) phenylisocyanate (0.098 g) was added to the solution. The mixture was heated at reflux for 23 hrs, and then, cooled to room temperature. The solvent was evaporated under reduced pressure, and the residue was purified with the column chromatography (ethyl acetate). A portion of this material (20 mg) was dissolved in tetrahydrofuran (1.0 mL) and treated with 1N hydrochloric acid solution (1.0 mL). The mixture was lyophilized to give {6-[2-(diethylamino)ethoxy]-1,3-dimethylpyrazolo[5,4-b]pyridin-5-yl}-N-({[4-fluoro-3-(trifluoromethyl)phenyl]amino}carbonyl)carboxamide hydrochloride as a white solid.

$^1$H NMR (DMSO-d$_6$) δ 1.25 (m, 8H), 2.49 (s, 3H), 3.61 (m, 2H), 3.93 (s, 3H), 4.85 (m, 2H), 7.51 (m, 1H), 7.86 (m, 1H), 8.08 (m, 1H), 8.52 (s, 1H), 10.24 (br s, 1H), 10.80 (d, J=4.0 Hz, 2H), MS (ESI) m/z 511 (M+H), 509 (M−H).

N-({[4-Fluoro3-(trifluoromethyl)phenyl]amino}carbonyl)(6-hydroxy-1,3-dimethylpyrazolo[pyrazolo[5,4-b]pyridin-5-yl)carboxamide (109).

$^1$H NMR (DMSO-d$_6$) δ 2.33 (s, 3H), 3.69 (s, 3H), 7.69 (t, J=10.0 Hz, 1H), 7.81 (m, 1H), 8.10 (m, 1H), 8.50 (s, 1H), 11.27 (s, 1H) 14.60 (br s, 1H). MS (ESI) m/z 412 (M+H), 4.10 (M−H).

[1,3-Dimethyl-6-(1-methylethoxy)pyrazolo[5,4-b]pyridin-5-yl]-N-({[4-fluoro-3-(trifluoromethyl)phenyl]amino}carbonyl)carboxamide (110).

$^1$H NMR (DMSO-d$_6$) δ 1.45 (d, J=6.0 Hz, 6H), 2.48 (s, 3H), 3.90 (s, 3H), 5.53 (m, 1H), 7.50 (t, J=9.6 Hz, 1H), 7.87 (m, 1H), 8.11 (m, 1H), 8.62 (s, 1H), 10.48 (br s, 1H), 10.75 (br s, 1H). MS (ESI) m/z 454 (M+H), 452 (M−H).

1,3-Dimethyl-6-(phenylmethoxy)pyrazolo[5,4-b]pyridin-5-yl]-N-({[4-fluoro-3-(trifluoromethyl)phenyl]amino}carbonyl)carboxamide (111).

$^1$H (DMSO-d$_6$) δ 2.48 (s, 3H), 3.93 (s, 3H), 5.60 (s, 2H), 7.31–7.41 (m, 3H), 7.49 (t, J=9.6 Hz, 1H), 7.58 (d, J=6.8 Hz, 2H), 7.85 (m, 1H), 8.07 (m, 1H), 8.58 (s, 1H), 10.63 (br s, 1H), 10.71 (br s, 1H). MS (ESI) m/z 502 (M+H), 500 (M−H).

N-({[4-Fluoro-3-(trifluoromethyl)phenyl]amino}carbonyl)(6-methoxy-1,3-dimethyl-pyrazolo[5,4-b]pyridin-5-yl)carboxamide (112).

$^1$H NMR (DMSO-d$_6$) δ 2.48 (s, 3H), 3.91 (s, 3H), 4.10(s, 3H), 7.50 (t, J=9.6 Hz, 1H), 7.88 (m, 1H), 8.09 (m, 1H), 8.55 (s, 1H), 10.62 (br s, 1H), 10.75 (br s, 1H). MS (ESI) m/z 426 (M+H), 424 (M−H).

(1,3-Dimethyl-6-morpholin-4-ylpyrazolo[5,4-b]pyridin-5-yl)-N-({[4-fluoro-3-(trifluoromethyl)phenyl]amino}carbonyl)carboxamide (113).

$^1$H NMR (DMSO-d$_6$) δ 2.45 (s, 3H), 3.34 (m, 4H), 3.75 (m, 4H), 3.87 (s, 3H), 7.50 (t, J=9.6 Hz, 1H), 7.87 (m, 1H), 8.10 (m, 1H), 8.39 (s, 1H), 10.69 (br s, 1H), 11.14 (br s, 1H). MS (ESI) m/z 481 (M+H), 479 (M−H).

[6-(Dimethylamino)-1,3-dimethylpyrazolo[5,4-b]pyridin-5-yl]-N-({[4-fluoro-3-(trifluoromethyl)phenyl]amino}carbonyl)carboxamide (114).

$^1$H NMR (DMSO-d$_6$) δ 2.40 (s, 3H), 3.03 (s, 6H), 3.82 (m, 4H), 2.98 (s, 3H), 3.64 (t, J=6.4 Hz, 2H), 3.82 (s, 3H), 7.49 (t, J=9.6 Hz, 1H), 7.87 (m, 1H), 8.10 (m, 1H), 8.22 (s, 1H), 10.76 (br s, 1H), 11.05 (br s, 1H). MS (ESI) m/z 439 (M+H), 437 (M−H).

[1,3-Dimethyl-6-(4-methylpiperazinyl)pyrazolo[5,4-b]pyridin-5-yl]-N-({[4-fluoro-3-(trifluoromethyl)phenyl]amino}carbonyl)carboxamide hydrochloride (115).

$^1$H NMR (DMSO-d$_6$) δ 2.45 (s, 3H), 2.80 (m, 3H), 3.12 (m, 2H), 3.48 (t, J=11.2 Hz, 1H), 3.89 (s, 3H), 7.51 (t, J=9.6 Hz, 1H), 7.87 (m, 1H), 8.09 (m, 1H), 8.41 (s, 1H), 10.74 (br s, 1H), 11.00 (br s, 1H).

{6-[2-(Dimethylamino)ethoxy]-1,3-dimethylpyrazolo[5,4-b]pyridin-5-yl}-N-({[4-fluoro-3-(trifluoromethyl)phenyl]amino}carbonyl)carboxamide hydrochloride (117).

$^1$H NMR (DMSO-d$_6$) δ 2.49 (s, 3H), 2.88 (s, 6H), 3.60 (m, 2H), 3.93 (s, 3H), 4.86 (m, 2H), 7.51 (t, J=9.6 Hz, 1H), 7.87 (m, 1H), 8.10 (m, 1H), 8.55 (s, 1H), 10.42 (br s, 1H), 10.70 (br s, 1H), 10.78 (br s, 1H). MS (ESI) m/z 483 (M+H), 481 (M−H).

{6-[2-(Dimethylamino)-isopropoxy]-1,3-dimethylpyrazolo[5,4-b]pyridin-5-yl}-N-({[4-fluoro-3-(trifluoromethyl)phenyl]amino}carbonyl)carboxamide hydrochloride (118).

$^1$H NMR (DMSO-d$_6$) δ 1.44 (d, J=6.4 Hz, 3H), 2.49 (s, 3H), 2.90 (s, 6H), 3.48–3.59 (m, 2H), 3.93 (s, 3H), 5.84 (m, 2H), 7.51 (t, J=9.6 Hz, 1H), 7.86 (m, 1H), 8.10 (m, 1H), 8.55 (s, 1H), 10.02 (br s, 1H), 10.65 (s, 1H), 10.73 (s, 1H). MS (ESI) m/z 497 (M+H), 495 (M−H).

{6-[3-(Dimethylamino)propoxy]-1,3-dimethylpyrazolo[5,4-b]pyridin-5-yl}-N-({[4-fluoro-3-(trifluoromethyl)phenyl]amino}carbonyl)carboxamide hydrochloride (119).

$^1$H NMR (DMSO-d$_6$) δ 2.24 (m, 2H), 2.49 (s, 3H), 2.73 (s, 1H), 2.78 (s, 5H), 3.48–3.59 (m, 2H), 3.92 (s, 3H), 4.58 (t, J=5.0 Hz, 21H), 7.51 (t, J=9.6 Hz, 1H), 7.89 (m, 1H), 8.10 (m, 1H), 8.55 (s, 1H), 10.11 (br s, 1H), 10.62 (s, 1H), 10.79 (s, 1H). MS (ESI) m/z 497 (M+H), 495 (M−H).

[1,3-Dimethyl-6-(2-pyrolidinylethoxy)pyrazolo[5,4-b]pyridin-5-yl]-N-({[4-fluoro-3-(trifluoromethyl)phenyl]amino}carbonyl)carboxamide hydrochloride (121).

$^1$H NMR (DMSO-d$_6$) δ 1.88–2.05 (m, 4H), 2.49 (s, 3H), 3.12–3.18 (m, 2H), 3.68 (m, 4H), 3.93 (s, 3H), 4.85 (t, J=4.8 Hz, 2H), 7.51 (t, J=9.6 Hz, 1H), 7.86 (m, 1H), 8.09 (m, 1H), 8.53 (s, 1H), 10.63 (br s, 1H), 10.62 (d, J=3.6 Hz, 2H). MS (ESI) m/z 509 (M+H), 507 (M−H).

[1,3-Dimethyl-6-(2-piperidylethoxoy)pyrazolo[5,4-b]pyridin-5-yl]-N-({[4-fluoro-3-(trifluoromethyl)phenyl]amino}carbonyl)carboxamide hydrochloride (122).

$^1$H NMR (DMSO-d$_6$) δ 1.38 (br s, 1H), 1.67–1.78 (m, 5H), 2.49 (s, 3H), 3.04 (br s, 2H), 3.57 (br s, 4H), 3.93 (s, 3H), 4.87 (br s, 2H), 7.53 (t, J=9.6 Hz, 1H), 7.88 (m, 1H), 8.09 (m, 1H), 8.54 (s, 1H), 10.17 (br s, 1H), 10.78 (s, 1H), 10.82 (s, 1H). MS (ESI) m/z 523 (M+H), 521 (M−H).

Example 10

N-({[4-Fluoro-3-(trifluoromethyl)phenyl]amino}carbonyl)(1-methyl-3-phenyl-pyrazolo[5,4-b]pyridin-5-yl)carboxamide (123)

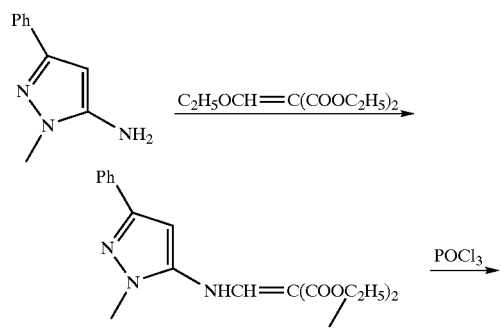

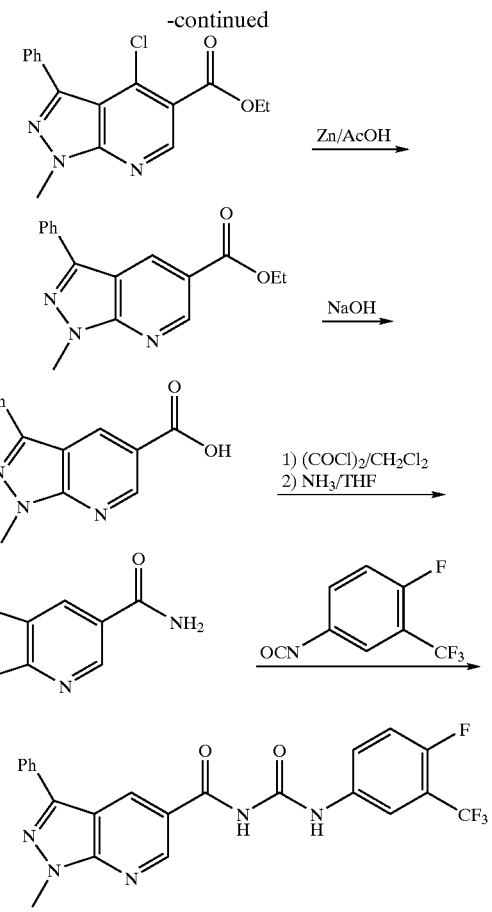

A mixture of 1-methyl-3-phenylpyrazol-5-ylamine (3.46 g) and diethyl 2-(ethoxymethylene)propane-1,3-dioate (4.33 g) was heated at 120° C. for 3 hrs with stirring, and then ethanol formed in the reaction was evaporated under reduced pressure. The residue was treated with hexane (50 mL), and the precipitated solid was filtered, washed with hexane, and dried under high vacuum. The solid was dissolved in phosphorus oxychloride (20 mL), heated at reflux for 14 hrs, and the reaction mixture was concentrated under reduced pressure. The residue was treated with water (50 mL), and the resulting solid was filtered, washed with water, and dried under high vacuum to give ethyl 1-methyl-3-phenyl-4-chloro-pyrazolo[5,4-b]pyridine-5-carboxylate.

The solid was dissolved in acetic acid (20 mL), and reacted with zinc (2.00 g) at 80° C. for 60 min. Zinc was removed by the filtration, and the filtrate was concentrated under reduced pressure. The residue was dissolved in ethanol (30 mL), and treated with 5N sodium hydroxide solution (30 mL). The mixture was heated at reflux for 6 hrs, and then solvent was evaporated under reduced pressure. The residue was poured into water (40 mL), filtered, and the filtrate was cooled in an ice-bath and acidified to pH 4 with concentrated hydrochloric acid. The precipitated solid was collected by the filtration, washed with water, and dried under high vacuum to give 1-methyl-3-phenylpyrazolo[5,4-b]pyridine-5-carboxamide acid as a white powder. The acid was suspended in anhydrous dichloromethane (50 mL) under an argon atmosphere and added oxalyl chloride (5.0 mL), followed by anhydrous DMF (0.5 mL). The mixture was stirred at room temperature for 6 hrs, and then concentrated under reduced pressure. The residue was cooled to ice-bath temperature and a saturated solution of ammonia in tetrahydrofuran (50 mL) was slowly added to the residue. The ice-bath was removed, the reaction mixture was stirred at room temperature for 6 hrs, and the precipitated solid was filtered. The solid was washed with water and dried under high vacuum to give 1-methyl-3-phenylpyrazolo[5,4-b]pyridine-5-carboxamide as a white powder.

A portion of this material (50 mg) was dissolved in hot toluene (5.0 mL) and azeotroped for 6 hrs. The solution was cooled to room temperature, 4-fluoro-3-(trifluoromethyl-phenylisocyanate (45 mg) was added, and refluxed for 16 hrs. The reaction mixture was cooled to room temperature and the precipitated solid was collected by the filtration, washed with methanol, and dried under high vacuum to give N-({[4-fluoro-3-(trifluoromethyl)phenyl]amino}carbonyl)(1-methyl-3-phenylpyrazolo[5,4-b]pyridin-5-yl)carboxamide as a white powder (45 mg).

$^1$H NMR (DMSO-d$_6$) δ 4.17 (s, 3H), 7.49–7.62 (m, 4H), 7.93 (m, 1H), 8.12–8.15 (m, 3H), 9.15 (d, J=2.2 Hz, 1H), 9.27 (d, J=2.2 Hz, 1H), 10.98 (s, 1H), 11.49 (s, 1H). (ESI) m/z 456 (M−H), 458 (M+H).

N-({[4-Fluoro-3-(trifluoromethyl)phenyl]amino}carbonyl)(1-methylpyrazolo[5,4-b]pyridin-5-yl)carboxamide (124).

$^1$H NMR (DMSO-d$_6$) δ 4.11 (s, 3H), 7.51 (dd, J=9.9, 9.9 Hz, 1H), 7.91 (m, 1H), 8.12 (dd, J=6.6, 2.6 Hz, 1H), 8.37 (s, 1H), 8.93 (d, J=2.2 Hz, 1H), 9.12 (d, J=2.2 Hz, 1H), 10.90 (s, 1H), 11.30 (s, 1H). MS (ESI) m/z 380 (M−H), 382 (M+H).

N-({[4-Fluoro-3-(trifluoromethyl)phenyl]amino}carbonyl)(3-methyl-1-phenylpyrazolo[5,4-b]pyridin-5-yl)carboxamide (125).

$^1$H NMR (DMSO-d$_6$) δ2.68 (s, 3H), 7.37 (m, 1H), 7.50–7.60 (m, 3H), 7.92 (m, 1H), 8.13 (dd, J=6.6, 2.6 Hz, 1H), 8.25 (dd, J=8.8, 1.1 Hz, 2H), 9.11 (d, J=2.2 Hz, 1H), 9.19 (d, J=2.2 Hz, 1H), 10.91 (s, 1H), 11.32 (s, 1H). MS (ESI) m/z 456 (M−H), 458 (M+H).

Example 11

N-({[4-Fluoro-3-(trifluoromethyl)phenyl]amino}carbonyl)[4-(4-methyl-piperazinyl)-1,3-diphenylpyrazolo[5,4-b]pyridin-5-yl]carboxamide (126)

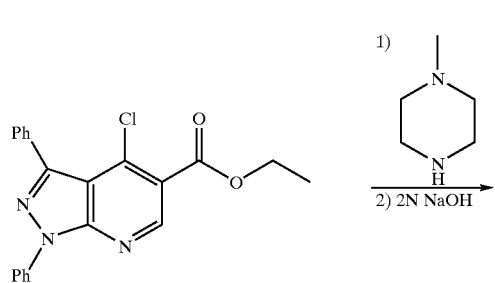

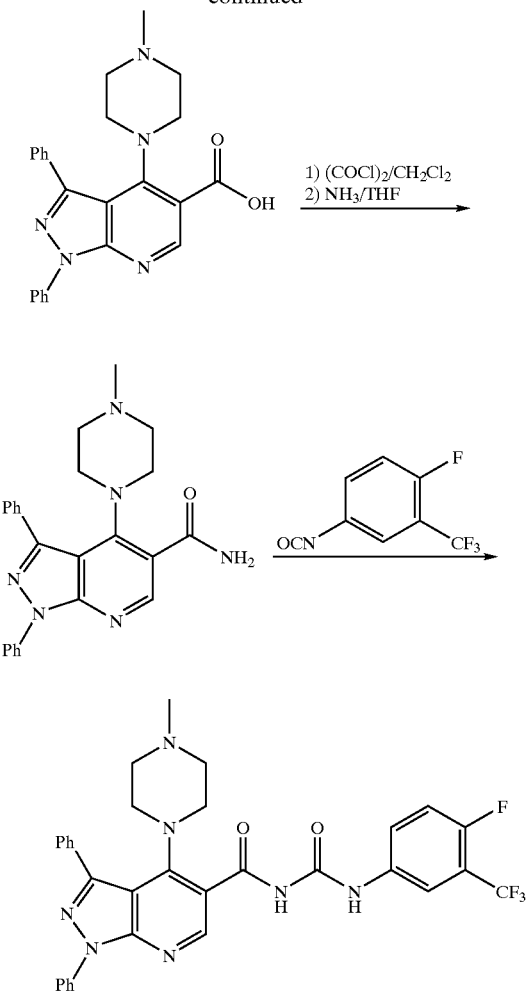

Ethyl 4-chloro-1,3-diphenylpyrazolo[5,4-b]pyridine-5-carboxylate (900 mg) and methylpiperazine (4.50 g) were dissolved in tetrahydrofuran (90 mL) and stirred at room temperature for 6 hrs. The reagents were removed under reduced pressure, the residue was dissolved in the mixture of ethanol (27 mL) and 5N sodium hydroxide solution (27 mL), and heated at reflux for 6 hrs. The solvent was evaporated under reduced pressure, the residue was dissolved in water (36 mL), insoluble solids were removed by the filtration. The filtrate was cooled in an ice-bath and acidified to pH 4 with concentrated hydrochloric acid. The precipitated solid was collected by the filtration, washed with water, and dried under high vacuum.

The solid was suspended in anhydrous dichloromethane (50 mL) under an argon atmosphere. Oxalyl chloride (5.0 mL) and anhydrous DMF (0.5 mL) was added to the suspension, and the reaction mixture was stirred at room temperature for 6 hrs. The oxalyl chloride was evaporated under reduced pressure, the residue was cooled in an ice bath, and a saturated solution of ammonia in tetrahydrofuran (50 mL) was slowly added. The ice bath was removed, the suspension was stirred at room temperature for 6 hrs. The precipitated solid was collected by the filtration, washed with water, and dried under high vacuum to give 1,3-diphenylpyrazolo[5,4-b]pyridine-5-carboxamide as a white powder.

A portion of this material (82 mg) was dissolved in hot toluene (8.0 mL) and azeotroped for 6 hrs. The solution was cooled to room temperature, added 4-fluoro-3-(trifluoromethyl)phenylisocyanate (49 mg), and heated at reflux for 16 hrs. The reaction mixture was cooled to room temperature, the precipitated solid was filtered, washed with methanol, and dried under high vacuum to give N-({[4-fluoro-3-(trifluoromethyl)phenyl]amino}carbonyl)-[4-(4-methylpiperazinyl)-1,3-diphenylpyrazolo[5,4-b]pyridin-5-yl]carboxamide as a white powder.

$^1$H NMR (DMSO-$d_6$) δ 1.91 (m, 4H), 2.01 (s, 3H), 3.10 (m, 4H), 7.37 (m, 1H), 7.48–7.60 (m, 6H), 7.68 (m, 2H), 7.91 (m, 1H), 8.12 (m, 1H), 8.18 (dd, J=8.8, 1.1 Hz, 2H), 8.50 (s, 1H), 10.65 (s, 1H), 11.38 (s, 1H). MS (ESI) m/z 616 (M–H), 618 (M+H).

N-({[4-Fluoro-3-(trifluoromethyl)phenyl]amino}carbonyl)-[4-(4-methylpiperazinyl)-1,3-diphenylpyrazolo[5,4-b]pyridin-5-yl]carboxamide hydrochloride (127)

MS (ESI) m/z 616 (M–H), 618 (M+H).

N-({[4-Fluoro-3-(trifluoromethyl)phenyl]amino}carbonyl)-[1-methyl-4-(4-methylpiperazinyl)-1,3-diphenylpyrazolo[5,4-b]pyridin-5-yl]carboxamide (128)

$^1$H NMR (DMSO-$d_6$) δ 1.92 (m, 4H), 2.00 (s, 3H), 3.06 (m, 4H), 4.06 (s, 3H), 7.48–7.59 (m, 6H), 7.91 (m, 1H), 8.12 (m, 1H), 8.41 (s, 1H), 10.67 (s, 1H), 11.31 (s, 1H). MS (ESI) m/z 554 (M–H), 556 (M+H).

N-({[4-Fluoro-3-(trifluoromethyl)phenyl]amino}carbonyl)-[1-methyl-4-(4-methylpiperazinyl)-3-phenylpyrazolo[5,4-b]pyridin-5-yl]carboxamide hydrochloride (129)

MS (ESI) m/z 554 (M–H), 556 (M+H).

Example 12

N-({[4-Fluoro-3-(trifluoromethyl)phenyl]amino}carbonyl-(1,3,6-trimethyl-pyrazolo[5,4-b]pyridin-5-yl)carboxamide (130)

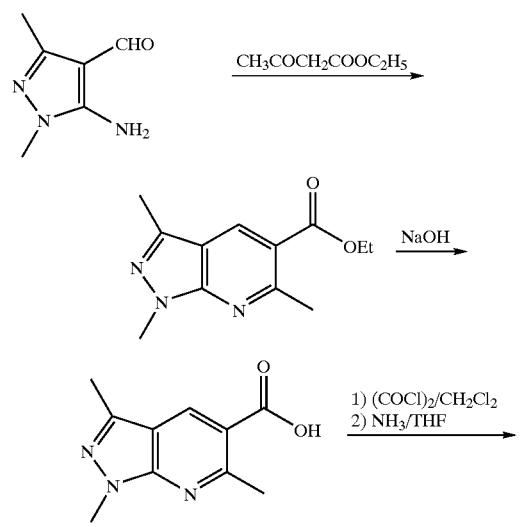

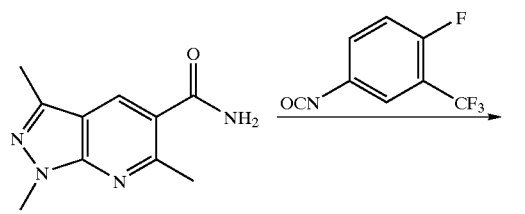

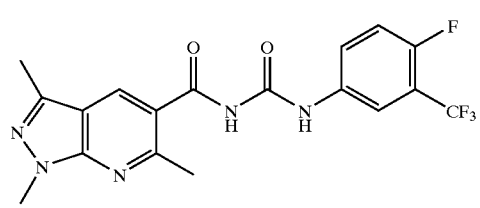

A solution of 5-amino-1,3-dimethylpyrazol-4-carbaldehyde (400 mg) and ethyl 3-oxobutanoate (600 mg) in piperidine (5 mL) was reflux for 3 hrs, the reagents were evaporated under reduced pressure, and the residue was washed with ether (5.0 mL) to give ethyl 1,3,6-trimethylpyrazolo[5,4-b]pyridin-5-yl)carboxamide as a white powder.

The solid was dissolved in the mixture of ethanol (5.0 mL) and 5N sodium hydroxide solution (5.0 mL), the solution was heated at reflux for 6 hrs, and then concentrated under reduced pressure. The residue was poured into water (4 mL), insoluble solid was removed by the filtration, the filtrate was cooled in an ice bath, and acidified to pH 4 with concentrated hydrochloric acid. The precipitated solid was collected by the filtration, washed with water, and dried under high vacuum.

The solid was suspended in anhydrous dichloromethane (5 mL) under an argon atmosphere. Oxalyl chloride (0.5 mL) and anhydrous DMF (0.05 mL) were added to the suspension, and the mixture was stirred at room temperature for 6 hrs. The reaction mixture was concentrated under reduced pressure, the residue was cooled in an ice bath, and a saturated solution of ammonia in tetrahydrofuran (5 mL) was slowly added into the residue. The ice-bath was removed and the suspension was stirred at room temperature for 1 hr. The precipitated solid was filtered, washed with water, and dried under high vacuum to give 1,3,6-trimethylpyrazolo[5,4-b]pyridin-5-carboxamide as a white powder. A portion of this material (50 mg) was dissolved in hot toluene (5.0 mL) and azeotroped for 6 hrs. The solution was cooled to room temperature, 4-fluoro-3-(trifluoromethyl)phenylisocyanate (55 mg) was added, and refluxed for 16 hrs. The reaction mixture was cooled to room temperature, the precipitated solid was filtered, washed with methanol, and dried under high vacuum to give N-({[4-fluoro-3-(trifluoromethyl)phenyl]amino}carbonyl)-(1,3,6-trimethylpyrazolo[5,4-b]pyridin-5-yl)carboxamide as a white powder.

$^1$H NMR (DMSO-$d_6$) δ 2.51 (s, 3H), 2.73 (s, 3H), 3.97 (s, 3H), 7.51 (dd, J=9.9, 9.9 Hz, 1H), 7.91 (m, 1H), 8.12 (dd, J=6.2, 2.6 Hz, 1H), 8.49 (s, 1H), 10.75 (s, 1H), 11.16 (s, 1H). MS (ESI) m/z 408 (M–H), 410 (M+H).

Example 13

Ethyl 1-{1,3-dimethyl-5-[N-({[3-(1-methylethoxy)phenyl]amino}carbonyl)carbamoyl]pyrazolo[5,4-b]pyridin-4-yl}piperidine-4-carboxamide (131)

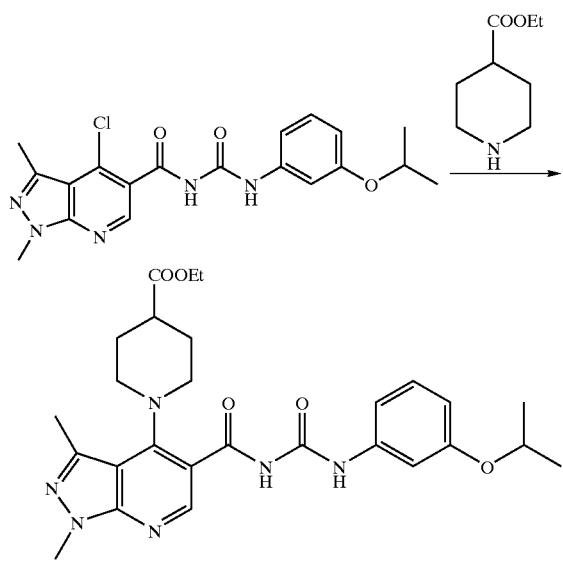

(4-Chloro-1,3-dimethylpyrazolo[5,4-b]pyridin-5-yl)-N-({[3-(1-methylethoxy)phenyl]amino}carbonyl)carboxamide (40 mg) was dissolved in tetrahydrofuran (5.0 mL), ethyl piperidine-4-carboxylate (160 mg) was added, and the mixture was stirred at room temperature for 5 hrs. The solvent was evaporated under reduced pressure, the residue was suspended in water (10 mL), the resulting solid was filtered, washed with water, and dried under high vacuum to give ethyl 1-{1,3-dimethyl-5-[N-({[3-(1-methylethoxy)phenyl]amino}carbonyl)carbamoyl]-pyrazolo[5,4-b]pyridin-4-yl}piperidine-4-carboxylate as a white powder.

$^1$H NMR (DMSO-$d_6$) δ 1.19 (t, J=7.3 Hz, 3H), 1.27 (d, J=5.9 Hz, 6H), 1.79 (m, 2H), 1.98 (m, 2H), 2.57 (m, 1H), 2.61 (s, 3H), 3.14 (m, 2H), 3.41 (m, 2H), 3.92 (s, 3H), 4.09 (q, J=7.3 Hz, 2H), 4.59 (m, 1H), 6.67 (dd, J=8.1, 1.1 Hz, 1H), 7.05 (dd, J=8.1, 2.6 Hz, 1H), 7.25 (m, 2H), 8.36 (s, 1H), 10.54 (s, 1H), 11.18 (s, 1H). MS (ESI) m/z 521 (M−H), 523 (M+H).

tert-Butyl 2-({1,3-dimethyl-5-[N-({[3-(1-methylethoxy)phenyl]amino}carbonyl)carbamoyl]pyrazolo[5,4-b]pyridin-4-yl}amino)acetate carboxamide (132).

$^1$H NMR (DMSO-$d_6$) δ 1.28 (d, J=6.2 Hz, 3H), 1.42 (s, 9H), 2.63 (s, 3H), 3.87 (s, 3H), 4.21 (d, J=5.9 Hz, 2H), 4.59 (m, 1H), 6.67 (dd, J=7.4, 1.8 Hz, 1H), 7.02 (dd, J=7.7, 2.6 Hz, 1H), 7,24 (m, 2H), 7.99 (br, 1H), 8.44 (s, 1H), 10.57 (s, 1H), 10.91 (s, 1H). MS (ESI) m/z 495 (M−H), 497 (M+H).

tert-Butyl 2-({1,3-dimethyl-5-[N-({[3-(1-methylethoxy)phenyl]amino}carbonyl)carbamoyl]pyrazolo[5,4-b]pyridin-4-yl}methylamino)acetate (133).

$^1$H NMR (DMSO-$d_6$) δ 1.27 (d, J=5.9 Hz, 3H), 1.42 (s, 9H), 2.64 (s, 3H), 3.06 (s, 3H), 3.88 (s, 2H), 3.93 (s, 3H), 4.60 (m, 1H), 6.67 (dd, J=8.0, 1.8 Hz, 1H), 7.06 (dd, J=8.1, 1.1 Hz, 1H), 7.25 (m, 2H), 8.41 (s, 1H), 10.57 (s, 1H), 11.02 (s, 1). MS (ESI) m/z 509 (M−H), 511 (M+H).

Example 14

3-methylisoxazolo[5,4-b]pyridine-5-carboxamide

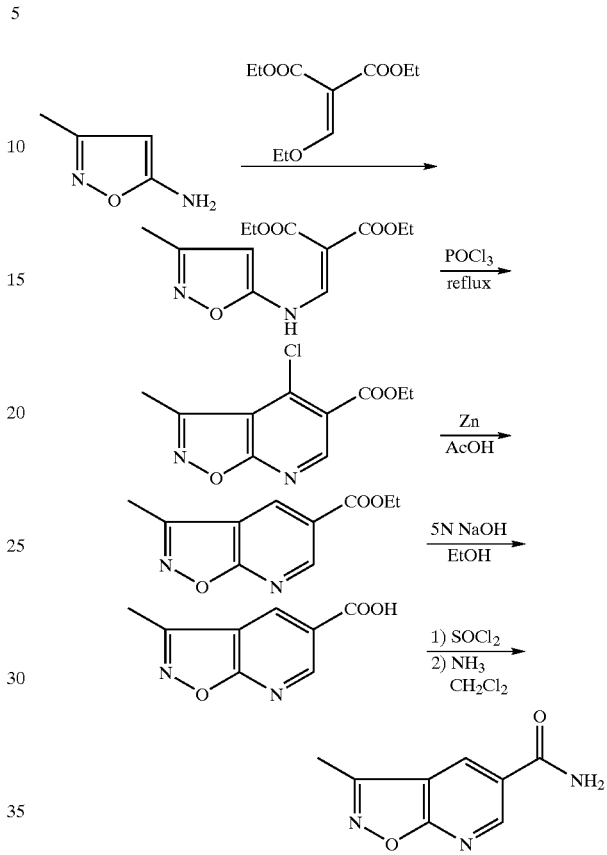

A mixture of 5-amino-3-methylisoxazole (5.26 g) and diethyl ethoxymethylenemalonate (10.9 ml) was heated at 120° C. for 3 hrs. The mixture was cooled to room temperature. The precipitated solid was collected, washed with n-hexane and dried under high vacuum. A portion of this solid (11.37 g) was dissolved in phosphoryl chloride (55 ml), heated at reflux for 11 hrs, and then cooled to room temperature. The mixture was concentrated under reduced pressure and the residue was purified with the column chromatography(ethyl acetate: n-hexane=1:9) to give ethyl 3-methylisoxazolo[5,4-b]pyridine-5-carboxylate as a white solid. Zinc powder (2.75 g) was added to a solution of a portion of the solid (2.43 g) in acetic acid (24 ml), the was stirred at 80° C. for 1.5 hrs, and then filtered. The filtrate was concentrated under reduced pressure. The residue was dissolved in a mixture of 5N NaOH (10 ml) and ethanol (10 ml), the solution was refluxed for 1.5 hrs, cooled to room temperature, and acidified with concentrated HCl. The precipitated solid was collected by the filtration, washed with water, and dried under high vacuum.

The solid was suspended in thionyl chloride (50 ml) and heated at 50° C. for 5 hrs. The thionyl chloride was evaporated under reduced pressure, the residue was dissolved with dichloromethane (5 ml), and reacted with ammonia gas at room temperature for 1 day. The reaction mixture was concentrated under reduced pressure, and the residue was treated with water. The precipitated solid was filtered, washed with water, and dried under high vacuum to give 3-methyl-isoxazolo[5,4-b]pyridine-5-carboxamide. Such a carboxamide may be reacted with an isocyanate or an amine to produce an acylurea compound of the invention according to Procedure A or B, respectively, above.

[1]NMR (DMSO-d$_6$) δ 2.62 (s, 3H), 7.72 (br.s, 1H), 8.27 (br.s, 1H), 8.87 (d, J=2.0 Hz, 1H), 9.11 (d, J=2.0 Hz, 1H). MS (ESI) m/z 176 (M−H).

Example 15

N-({[4-fluoro-3-(trifluoromethyl)phenyl]amino}carbonyl)[3-methyl-4-(4-methylpiperazinyl)isoxazolo[5,4-b]pyridin-5-yl]carboxamide (134)

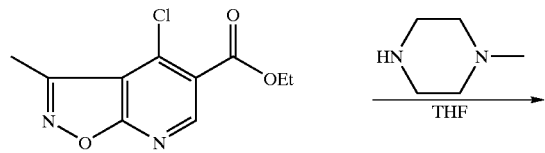

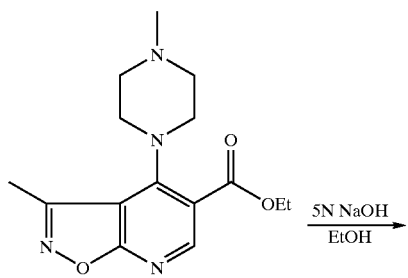

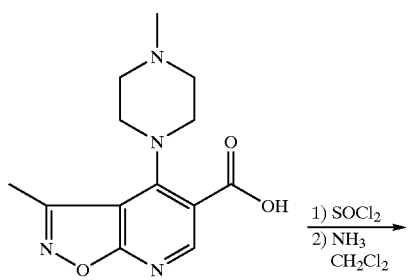

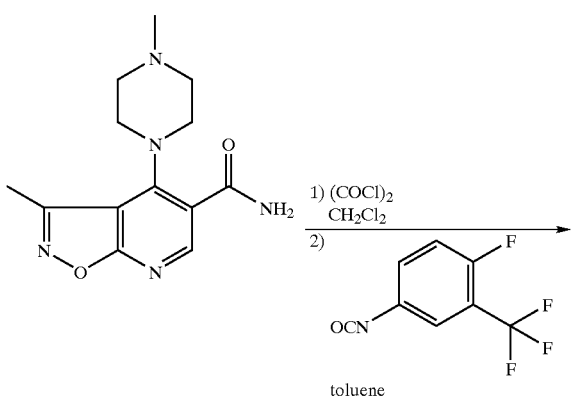

-continued

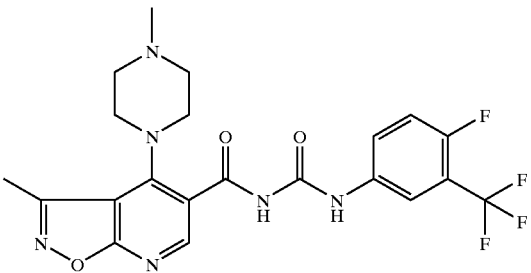

A solution of ethyl 4-chloro-3-methylisoxazolo[5,4-b]pyridin-5-carboxylate (1.02 g) and 1-methylpiperazine (1.12 ml) in tetrahydrofuran (10 ml) was stirred at room temperature for 1 hr and then concentrated under reduced pressure. The residue was treated with water, the precipitated solid was filtered, washed with water, and dried under high vacuum. This solid was suspended in ethanol (1 ml), added 5N NaOH (11 ml , and the mixture was stirred at 60° C. for 1 hr. The reaction mixture was treated with 5N HCl and purified by ODS column (VARIAN MEGABOND ELUT C18) to give 3-methyl-4-(4-methyl-piperazin-1-yl)isoxazolo[5,4-b]pyridine-5-carboxylic acid as an amorphous solid. A portion of this amorphous solid (417 mg) was dissolved in thionyl chloride (40 ml) and heated at 50° C. for 3.5 hrs. The mixture was concentrated under reduced pressure, the residue was dissolved in THF (20 ml), and reacted with ammonia gas at room temperature for 3 hrs. The reaction mixture was concentrated under reduced pressure, the residue was treated with water, the resulting solid was filtered, washed with water, and dried under high vacuum to give the 3-methyl-4-(4-methylpiperazin-1-yl)-isoxazolo[5,4-b]pyridin-5-carboxylic acid amide.

A portion of this material (50 mg) was dissolved in toluene (5 ml) and azeotroped for 3 hrs. The solution was cooled to room temperature and then reacted with 4-fluoro-3(trifluoromethyl)phenyl isocyanate (0.031 ml). The mixture was refluxed for 3 hrs and then cooled to room temperature. The reaction mixture was concentrated under reduced pressure and the residue was purified with p-TLC (methanol) to give N-({[4-fluoro-3-(trifluoromethyl)phenyl]amino}carbonyl)[3-methyl-4-(4-methylpiperazinyl)isoxazolo[5,4-b]pyridin-5-yl]carboxamide (134).

$^1$H NMR (DMSO-d$_6$) δ 2.23 (s, 3H), 2.64 (s, 3H), 3.16–3.51(m, 8H), 7.45 (t, J=9.7 Hz, 1H), 7.84 (m, 1H), 8.13 (m, 1H), 8.39 (s, 1H). MS (ESI) m/z 481 (M+H), 479 (M−H).

N-({[4-fluoro-3-(trifluoromethyl)phenyl]amino}carbonyl)[3-methyl-4-(4-methylpiperazinyl)isoxazolo[5,4-b]pyridin-5-yl]carboxamide hydrochloride (135).

$^1$H NMR (DMSO-d$_6$) δ 2.50 (m, 3H), 2.69 (s, 3H), 3.25–3.42 (m, 8H), 7.53 (t, J=9.8 Hz, 1H), 7.89 (m, 1H), 8.11 (m, 1H), 8.56 (br.s, 1H), 10.61 (br.s, 1H), 11.48 (br.s, 1H). MS (ESI) m/z 481 (M+H), 479 (M−H).

[4-(dimethylamino)-3-methylisoxazolo[5,4-b]pyridin-5-yl]-N-({[4-fluoro-3-(trifluoromethyl)phenyl]amino}carbonyl)carboxamide (136).

¹H NMR (DMSO-d₆) δ 2.64 (s, 3H), 3.10 (s, 6H), 7.53 (t, J=9.9 Hz, 1H), 7.91 (m, 1H), 8.11 (m, 1H), 8.36 (s, 1H), 10.68 (br.s, 1H), 11.32(br.s, 1H). MS (ESI) m/z 426 (M+H), 424 (M–H).

(4-{[2-(dimethylamino)ethyl]methylamino}-3-methyl-isoxazolo[5,4-b]pyridin-5-yl)-N-({[4-fluoro-3-(trifluoromethyl)phenyl]amino}carbonyl)carboxamide (137).

¹H NMR (DMSO-d₆) δ 2.50 (s, 6H), 2.65 (s, 3H), 3.08 (s, 3H), 3.35 (m, 2H), 3.58 (m, 2H), 7.52 (t, J=9.7 Hz, 1H), 7.91 (m, 1H), 8.14 (m, 1H), 8.46 (s, 1H),10.80 (br.s 1H). MS (ESI) m/z 483 (M+H), 481 (M–H).

(4-{[2-(dimethylamino)ethyl]methylamino}-3-methyl-isoxazolo[5,4-b]pyridin-5-yl)-N-({[4-fluoro-3-(trifluoromethyl)phenyl]amino}carbonyl)carboxamide hydrochloride (138).

¹H NMR (DMSO-d₆) δ 2.69 (s, 3H), 2.75 (br.d, J=4 Hz, 6H), 3.17 (br.s, 3H), 3.37 (m, 2H), 3.76 (m, 2H), 7.53 (t, J=9.5 Hz, 1H), 7.88 (m, 1H), 8.10 (m, 1H), 8.52 (s, 1H), 10.44 (br.s, 1H), 10.67 (br.s, 1H), 11.39 (br.s, 1H). MS (ESI) m/z 483 (M+H), 481 (M–H).

N-({[4-fluoro-3-(trifluoromethyl)phenyl]amino}carbonyl)(3-methyl-4-morpholin-4-yl-isoxazolo[5,4-b]pyridin-5-yl)carboxamide (139).

¹H NMR (DMSO-d₆) δ 2.66 (s, 3H), 3.79 (m, 4H), 7.52 (t, J=9.7 Hz, 1H), 7.91 (1Hrs), 8.12 (m, 1H), 8.50 (s, 1H), 10.63 (br.s, 1H), 11.48 (br.s, 1H). MS (ESI) m/z 468 (M+H), 466 (M–H).

Compounds of General Formulae III to VI:

The compounds shown in Tables 1 to 4 were prepared either by the procedures described above or by modifications of these procedures familiar to those skilled in the art.

TABLE 1

III

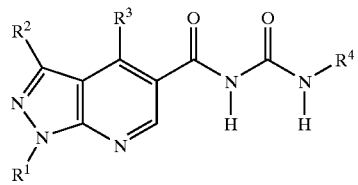

| Cmpd | R¹ | R² | R³ | R⁴ | MW | MS (m/z) |
|---|---|---|---|---|---|---|
| 1 | Me | Me | H | 4-fluorophenyl | 327.32 | 326 |
| 2 | Me | Me | H | 3,4-dichlorophenyl | 378.22 | 376, 378, 380 |
| 3 | Me | Me | H | 3-chlorophenyl | 343.77 | 342, 344 |
| 4 | Me | Me | H | 2,4-dichlorophenyl | 378.22 | 376, 378, 380 |
| 5 | Me | Me | H | 4-chlorophenyl | 343.77 | 342, 344 |
| 6 | Me | Me | H | 4-iodophenyl | 435.22 | 434 |
| 7 | Me | Me | H | 3-cyanophenyl | 334.34 | 333 |
| 8 | Me | Me | H | 3-bromophenyl | 388.23 | 388, 390 |
| 9 | Me | Me | H | 3-chloro-4-hydroxyphenyl | 359.77 | 358, 360 |
| 10 | Me | Me | H | 3,5-bis(trifluoromethyl)phenyl | 445.32 | 444 |
| 11 | Me | Me | H | 4-fluoro-3-(trifluoromethyl)phenyl | 395.32 | 394 |
| 12 | Me | Me | H | 3-fluoro-4-(trifluoromethyl)phenyl | 395.32 | 394 |
| 13 | Me | Me | H | 4-nitro-3-(trifluoromethyl)phenyl | 422.32 | 421 |
| 14 | Me | Me | H | 2,3-dichlorophenyl | 378.22 | 376, 378, 380 |
| 15 | Me | Me | H | 2,6-dichlorophenyl | 378.22 | 376, 378 380 |
| 16 | Me | Me | H | 2,5-dichlorophenyl | 378.22 | 376, 378, 380 |
| 17 | Me | Me | H | 3,5-dichlorophenyl | 378.22 | 376, 378, 380 |
| 18 | Me | Me | H | 2-chloro-5-(trifluoromethyl)phenyl | 411.77 | 410, 412 |
| 19 | Me | Me | H | 4-chloro-2-(trifluoromethyl)phenyl | 411.77 | 410, 412 |
| 20 | Me | Me | H | 2-chloro-4-(trifluoromethyl)phenyl | 411.77 | 410, 412 |
| 21 | Me | Me | H | 4-chloro-3-(trifluoromethyl)phenyl | 411.77 | 410, 412 |
| 22 | Me | Me | H | 2,5-bis(trifluoromethyl)phenyl | 445.32 | 444 |
| 23 | Me | Me | H | 3,4-bis(trifluoromethyl)phenyl | 445.32 | 444 |
| 24 | Me | Me | H | 3-iodophenyl | 435.22 | 434 |
| 25 | Me | Me | H | 3-chloro-4-(carboxymethyleneoxy)phenyl | 417.81 | 416 |
| 26 | Me | Me | H | 3-(trifluoromethyl)phenyl | 377.33 | 376 |
| 27 | Me | Me | H | 4-hydroxy-3-(trifluoromethyl)phenyl | 393.32 | 392 |
| 28 | Me | Me | H | 5-hydroxy-3-(trifluoromethyl)phenyl | 393.32 | 392 |
| 29 | Me | Me | H | 5-carboxy-3-(trifluoromethyl)phenyl | 421.33 | 420 |
| 30 | Me | Me | H | 3-isopropoxyphenyl | 367.41 | 366 |
| 31 | Me | Me | H | 3-phenoxyphenyl | 401.43 | 400 |
| 32 | Me | Me | H | 3-phenylphenyl | 385.43 | 384 |
| 33 | Me | Me | H | 4-carboxy-3-isopropoxyphenyl | 411.42 | 410 |
| 34 | Me | Me | H | 3-trifluoromethyl-4-(ethoxycarbonylmethyleneoxy)phenyl | 479.41 | 480 |
| 35 | Me | Me | H | 3-trifluoromethyl-4-(carboxymethyleneoxy)phenyl | 451.36 | 450 |

TABLE 1-continued

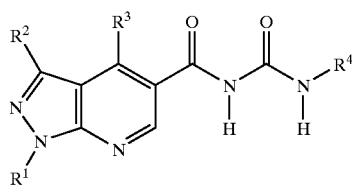

III

| Cmpd | R¹ | R² | R³ | R⁴ | MW | MS (m/z) |
|---|---|---|---|---|---|---|
| 36 | Me | Me | Cl | 3-chlorophenyl | 378.22 | 376, 378, 380 |
| 37 | Me | Me | Cl | 3,4-dichlorophenyl | 412.66 | 374, 376, 378 |
| 38 | Me | Me | Cl | 4-(trifluoromethyl)phenyl | 411.77 | 374 |
| 39 | Me | Me | Cl | 4-chlorophenyl | 378.22 | 340, 342 |
| 40 | Me | Me | H | 3-chloro-4-(carboxymethyleneoxy)-phenyl(Na salt) | 439.82 | 416 |
| 41 | Me | Me | H | 4-carboxyphenyl | 353.34 | 352 |
| 42 | Me | Me | H | 3-(trifluoromethyl)phenyl | 377.32 | 376 |

TABLE 2

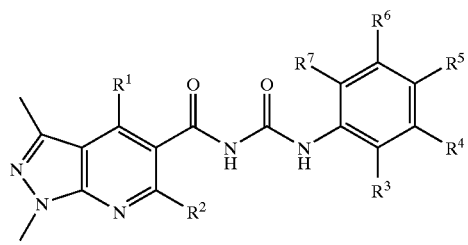

IV

| Cmpd | R¹ | R² | R³ | R⁴ | R⁵ | R⁶ | R⁷ | Salt | MW | MS (m/z) |
|---|---|---|---|---|---|---|---|---|---|---|
| 43 | OH | H | H | CF₃ | F | H | H | — | 411.31 | 410 |
| 44 | Me₂N— | H | H | CF₃ | F | H | H | — | 438.38 | 437 |
| 45 | Me₂NCH₂CH₂NH— | H | H | CF₃ | F | H | H | — | 481.45 | 480 |
| 46 | Me₂NCH₂CH₂NH— | H | H | CF₃ | F | H | H | HCl | 517.91 | ND |
| 47 | Me₂NCH₂CH₂N(Me)- | H | H | CF₃ | F | H | H | — | 495.48 | 494 |
| 48 | Me₂NCH₂CH₂N(Me)- | H | H | CF₃ | F | H | H | HCl | 531.94 | ND |
| 49 | Me₂N(CH₂)₃NH— | H | H | CF₃ | F | H | H | — | 495.48 | 494 |
| 50 | Me₂N(CH₂)₃NH— | H | H | CF₃ | F | H | H | HCl | 531.94 | ND |
| 51 | —N(CH₂CH₂OH)₂ | H | H | CF₃ | F | H | H | — | 498.44 | 497 |
| 52 | 2-(4-morpholinyl)-ethylamino | H | H | CF₃ | F | H | H | — | 523.49 | 522 |
| 53 | methyl (1-methyl-pyrrolidin-3-yl)amino | H | H | CF₃ | F | H | H | — | 507.49 | 506 |
| 54 | methyl (1-methyl-pyrrolidin-3-yl)amino | H | H | CF₃ | F | H | H | HCl | 543.95 | ND |
| 55 | (4-aminocyclohexyl)-amino | H | H | CF₃ | F | H | H | — | 507.49 | 506 |
| 56 | (4-aminocyclohexyl)-amino | H | H | CF₃ | F | H | H | HCl | 543.95 | ND |
| 57 | 2-perhydropyrrolizin-7α-ylmethylamino | H | H | CF₃ | F | H | H | — | 533.53 | 532 |
| 58 | 2-perhydropyrrolizin-7α-ylmethylamino | H | H | CF₃ | F | H | H | HCl | 569.99 | ND |
| 59 | 2-perhydropyrrolizin-7α-ylmethylamino | H | H | CF₃ | F | H | H | — | 547.56 | 546 |
| 60 | 2-perhydropyrrolizin-7α-ylmethylamino | H | H | CF₃ | F | H | H | HCl | 584.02 | ND |
| 61 | benzylamino | H | H | CF₃ | F | H | H | — | 500.46 | 499 |
| 62 | 3-(dimethylamino)-pyrrolidinyl | H | H | CF₃ | F | H | H | — | 507.49 | 506 |
| 63 | 3-(dimethylamino)-pyrrolidinyl | H | H | CF₃ | F | H | H | HCl | 543.95 | ND |
| 64 | piperidyl | H | H | CF₃ | F | H | H | — | 478.45 | 477 |
| 65 | 4-morpholyl | H | H | CF₃ | F | H | H | — | 480.43 | 479 |
| 66 | 4-piperazinyl | H | H | CF₃ | F | H | H | — | 479.44 | 478 |
| 67 | 4-piperazinyl | H | H | CF₃ | F | H | H | HCl | 515.90 | ND |
| 68 | 4-methylpiperazinyl | H | H | Cl | H | H | H | HCl | 478.38 | 440, 442 |
| 69 | 4-methylpiperazinyl | H | H | Br | H | H | H | HCl | 522.84 | 486 |
| 70 | 4-methylpiperazinyl | H | H | H | Cl | H | H | — | 441.92 | 440 |
| 71 | 4-methylpiperazinyl | H | H | Cl | Cl | H | H | — | 476.37 | 474, 476 |

TABLE 2-continued

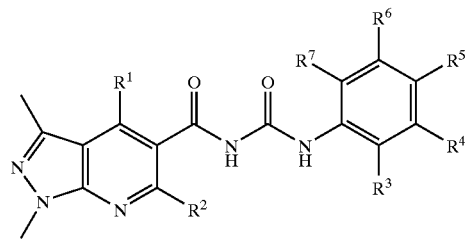

IV

| Cmpd | R¹ | R² | R³ | R⁴ | R⁵ | R⁶ | R⁷ | Salt | MW | MS (m/z) |
|---|---|---|---|---|---|---|---|---|---|---|
| 72 | 4-methylpiperazinyl | H | H | CF₃ | H | H | H | — | 475.47 | 474 |
| 73 | 4-methylpiperazinyl | H | H | CF₃ | H | H | H | HCl | 511.94 | 474 |
| 74 | 4-methylpiperazinyl | H | H | i-Pr | H | H | H | HCl | 486.02 | 448 |
| 75 | 4-methylpiperazinyl | H | H | O-i-Pr | H | H | H | HCl | 502.02 | 464 |
| 76 | 4-methylpiperazinyl | H | H | O-i-Pr | CO₂H | H | H | — | 509.57 | 508 |
| 77 | 4-methylpiperazinyl | H | H | OCF₃ | H | H | H | HCl | 527.93 | 490 |
| 78 | 4-methylpiperazinyl | H | H | 1,3-thiazol-2-yl | H | H | H | — | 490.59 | 489 |
| 79 | 4-methylpiperazinyl | H | H | 1,3-thiazol-2-yl | H | H | H | HCl | 527.05 | ND |
| 80 | 4-methylpiperazinyl | H | H | Ph | H | H | H | — | 483.58 | 482 |
| 81 | 4-methylpiperazinyl | H | H | Ph | H | H | H | HCl | 520.04 | 482 |
| 82 | 4-methylpiperazinyl | H | H | OPh | H | H | H | — | 499.57 | 498 |
| 83 | 4-methylpiperazinyl | H | H | CF₃ | Me | H | H | HCl | 525.96 | 488 |
| 84 | 4-methylpiperazinyl | H | H | CF₃ | F | H | H | — | 493.46 | 492 |
| 85 | 4-methylpiperazinyl | H | H | CF₃ | F | H | H | HCl | 529.93 | ND |
| 86 | 4-methylpiperazinyl | H | H | F | CF₃ | H | H | — | 493.46 | 492 |
| 87 | 4-methylpiperazinyl | H | H | CF₃ | OH | H | H | — | 491.47 | 490 |
| 88 | 4-methylpiperazinyl | H | H | CF₃ | OH | H | H | HCl | 527.93 | ND |
| 89 | 4-methylpiperazinyl | H | H | CF₃ | H | OH | H | — | 491.47 | 490 |
| 90 | 4-methylpiperazinyl | H | H | CF₃ | H | OH | H | HCl | 527.93 | ND |
| 91 | 4-methylpiperazinyl | H | H | CF₃ | H | CF₃ | H | HCl | 579.93 | 542 |
| 92 | 4-methylpiperazinyl | H | H | CO₂i-Pr | Cl | H | H | HCl | 564.47 | 526 |
| 93 | 4-methylpiperazinyl | H | H | PhC(=O)— | H | H | H | HCl | 548.05 | 510 |
| 94 | 4-phenylpiperazinyl | H | H | Cl | 4-morpholinyl-carbonyl | H | H | — | 555.04 | 553 |
| 95 | 4-methylpiperazinyl | H | H | 4-morpholinyl-carbonyl | Cl | H | H | HCl | 592.51 | 555, 557 |
| 96 | 4-methylpiperazinyl | H | H | 4-methylpiper-azinylcarbonyl | Cl | H | H | — | 568.08 | 566 |
| 97 | 4-methylpiperazinyl | H | H | Cl | 4-methylpiper-azinylcarbonyl | H | H | — | 568.08 | 566 |
| 98 | 4-methylpiperazinyl | H | H | CF₃ | F | H | H | Me-I | 635.40 | 508 |
| 99 | 4-ethylpiperazinyl | H | H | CF₃ | F | H | H | — | 507.49 | 506 |
| 100 | 4-ethylpiperazinyl | H | H | CF₃ | F | H | H | HCl | 543.95 | ND |
| 101 | 4-(2-hydroxyethyl)-piperazinyl | H | H | CF₃ | F | H | H | — | 523.49 | 522 |
| 102 | 4-(2-hydroxyethyl)-piperazinyl | H | H | CF₃ | F | H | H | HCl | 559.95 | ND |
| 103 | 4-phenylpiperazinyl | H | H | CF₃ | F | H | H | — | 555.54 | 554 |
| 104 | 4-benzylpiperazinyl | H | H | CF₃ | F | H | H | — | 569.56 | 568 |
| 105 | 4-benzylpiperazinyl | H | H | CF₃ | F | H | H | HCl | 606.02 | ND |
| 106 | 4-aminopyridinyl | H | H | CF₃ | F | H | H | HCl | 523.88 | 486 |
| 107 | 4-methyl-1,4-diaza-perhydroepinyl | H | H | CF₃ | F | H | H | — | 507.49 | 506 |
| 108 | 4-methyl-1,4-diaza-perhydroepinyl | H | H | CF₃ | F | H | H | HCl | 543.95 | ND |
| 140 | H | Me₂NCH₂CH₂N(Me) | H | O-iPr | H | H | H | HCl | | |
| 141 | H | H | H | Cl | 4-morpholinyl-carbonyl | H | H | — | | |
| 142 | H | H | H | Cl | 4-methylpiper-azinylcarbonyl | H | H | — | | |

TABLE 3

V

[Structure: 3-methyl-isoxazolo[5,4-b]pyridine with R at 4-position and 5-carboxamide-NH-C(O)-NH-(4-fluoro-3-(trifluoromethyl)phenyl)]

| Cmpd | R | MW | MS (M + H) (m/z) | MS (M − H) m/z |
|---|---|---|---|---|
| 134 | 4-methylpiperazinyl | 480.42 | 481 | 479 |
| 135 | 4-methylpiperazinyl (HCl salt) | 516.88 | 481 | 479 |
| 136 | dimethylamino | 425.34 | 426 | 424 |
| 137 | [2-(dimethylamino)ethyl]methylamino | 482.43 | 483 | 481 |
| 138 | [2-(dimethylamino)ethyl]-methylamino (HCl salt) | 518.89 | 483 | 481 |
| 139 | morpholinyl | 467.37 | 468 | 466 |

TABLE 4

VI

[Structure: pyrazolo[3,4-b]pyridine with R¹ on N1, R² at 3-position, R³ at 4-position, R⁴ at 6-position, and 5-carboxamide-NH-C(O)-NH-R⁵]

| Cmpd | R¹ | R² | R³ | R⁴ | R⁵ | MW | MS (m/z) (M − H) | MS (m/z) (M + H) |
|---|---|---|---|---|---|---|---|---|
| 109 | Me | Me | H | OH | 4-fluoro-3-(trifluoromethyl)phenyl | 411.32 | 410 | 412 |
| 110 | Me | Me | H | 1-methylethoxy | 4-fluoro-3-(trifluoromethyl)phenyl | 453.40 | 452 | 454 |
| 111 | Me | Me | H | phenylmethoxy | 4-fluoro-3-(trifluoromethyl)phenyl | 501.44 | 500 | 502 |
| 112 | Me | Me | H | methoxy | 4-fluoro-3-(trifluoromethyl)phenyl | 425.35 | 424 | 426 |
| 113 | Me | Me | H | morpholinyl | 4-fluoro-3-(trifluoromethyl)phenyl | 480.43 | 479 | 481 |
| 114 | Me | Me | H | dimethyl-amino | 4-fluoro-3-(trifluoromethyl)phenyl | 438.39 | 437 | 439 |
| 115 | Me | Me | H | 4-methyl-piperazinyl (HCl salt) | 4-fluoro-3-(trifluoromethyl)phenyl | 529.93 | 492 | 494 |
| 116 | Me | Me | H | [2-(dimethyl-amino)ethyl]-methylamino (HCl salt) | 4-fluoro-3-(trifluoromethyl)phenyl | 531.94 | 494 | 496 |
| 117 | Me | Me | H | 2-(dimethyl-amino)ethoxy (HCl salt) | 4-fluoro-3-(trifluoromethyl)phenyl | 518.90 | 481 | 483 |

TABLE 4-continued

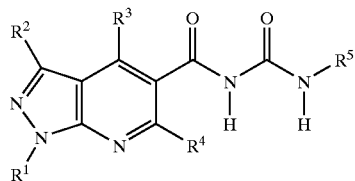

| Cmpd | R¹ | R² | R³ | R⁴ | R⁵ | MW | MS (m/z) (M − H) | MS (m/z) (M + H) |
|---|---|---|---|---|---|---|---|---|
| 118 | Me | Me | H | 2-(dimethyl-amino)-iso-propoxy (HCl salt) | 4-fluoro-3-(trifluoromethyl)phenyl | 532.93 | 495 | 497 |
| 119 | Me | Me | H | 3-(dimethyl-amino)propoxy (HCl salt) | 4-fluoro-3-(trifluoromethyl)phenyl | 532.93 | 495 | 497 |
| 120 | Me | Me | H | 2-(diethyl-amino)ethoxy (HCl salt) | 4-fluoro-3-(trifluoromethyl)phenyl | 546.96 | 509 | 511 |
| 121 | Me | Me | H | 2-pyrrolidinyl-ethoxy | 4-fluoro-3-(trifluoromethyl)phenyl | 544.94 | 507 | 509 |
| 122 | Me | Me | H | 2-piperidyl-ethoxy | 4-fluoro-3-(trifluoromethyl)phenyl | 558.97 | 521 | 523 |
| 123 | Me | Ph | H | H | 4-fluoro-3-(trifluoromethyl)phenyl | 457.39 | 456 | 458 |
| 124 | Me | H | H | H | 4-fluoro-3-(trifluoromethyl)phenyl | 381.29 | 380 | 382 |
| 125 | Ph | Me | H | H | 4-fluoro-3-(trifluoromethyl)phenyl | 457.39 | 456 | 458 |
| 126 | Ph | Ph | 4-methyl-piperazine | H | 4-fluoro-3-(trifluoro-methyl)phenyl | 617.61 | 616 | 618 |
| 127 | Ph | Ph | 4-methyl-piperazine HCl | H | 4-fluoro-3-(trifluoromethyl)phenyl | 654.07 | 616 | 618 |
| 127 | Me | Ph | 4-methyl-piperazine | H | 4-fluoro-3-(trifluoromethyl)phenyl | 555.54 | 554 | 556 |
| 129 | Me | Ph | 4-methyl-piperazine HCl | H | 4-fluoro-3-(trifluoromethyl)phenyl | 592.00 | 554 | 556 |
| 130 | Me | Me | H | Me | 4-fluoro-3-(trifluoromethyl)phenyl | 409.35 | 408 | 410 |
| 131 | Me | Me | ethyl-pipendine-4-carboxylate | H | 4-fluoro-3-(trifluoromethyl)phenyl | 522.61 | 521 | 523 |
| 132 | Me | Me | tert-butyl 2-amino-acetate | H | 4-fluoro-3-(trifluoromethyl)phenyl | 496.57 | 495 | 497 |
| 133 | Me | Me | tert-butyl 2-(methyl-amino)-acetate | H | 4-fluoro-3-(trifluoromethyl)phenyl | 510.60 | 509 | 511 |

The names of the compounds shown in Tables 1 to 4 are given in Tables 5 and 6. These were generated with the Chemistry 4-D Draw™ software from ChemInnovation Inc. (San Diego, Calif).

TABLE 5

| Cmpd | Name |
|---|---|
| 1 | (1,3-Dimethylpyrazolo[5,4-b]pyridin-5-yl)-N-{[(4-fluorophenyl)amino]carbonyl}-carboxamide |
| 2 | N-{[(3,4-Dichlorophenyl)amino]carbonyl}(1,3-dimethylpyrazolo[5,4-b]-pyridin-5-yl)carboxamide |
| 3 | (1,3-Dimethylpyrazolo[5,4-b]pyridin-5-yl)-N-{[(3-chlorophenyl)amino]carbonyl}-carboxamide |
| 4 | N-{[(2,4-Dichlorophenyl)amino]carbonyl}(1,3-dimethylpyrazolo[5,4-b]-pyridin-5-yl)carboxamide |
| 5 | (1,3-Dimethylpyrazolo[5,4-b]pyridin-5-yl)-N-{[(4-chlorophenyl)amino]carbonyl}-carboxamide |
| 6 | (1,3-Dimethylpyrazolo[5,4-b]pyridin-5-yl)-N-{[(4-iodophenyl)amino]carbonyl}-carboxamide |
| 7 | (1,3-Dimethylpyrazolo[5,4-b]pyridin-5-yl)-N-{[(3-cyanophenyl)amino]carbonyl}-carboxamide |
| 8 | (1,3-Dimethylpyrazolo[5,4-b]pyridin-5-yl)-N-{[(3-bromophenyl)amino]carbonyl}-carboxamide |
| 9 | (1,3-Dimethylpyrazolo[5,4-b]pyridin-5-yl)-N-{[(3-chloro-4-hydroxyphenyl)amino]-carbonyl}carboxamide |
| 10 | (1,3-Dimethylpyrazolo[5,4-b]pyridin-5-yl)-N-({[3,5-bis(trifluoromethyl)phenyl]-amino}carbonyl)carboxamide |
| 11 | (1,3-Dimethylpyrazolo[5,4-b]pyridin-5-yl)-N-({[4-fluoro-3-(trifluoromethyl)phenyl]-amino}carbonyl)carboxamide |
| 12 | (1,3-Dimethylpyrazolo[5,4-b]pyridin-5-yl)-N-({[3-fluoro-4-(trifluoromethyl)phenyl]-amino}carbonyl)carboxamide |
| 13 | (1,3-Dimethylpyrazolo[5,4-b]pyridin-5-yl)-N-({[4-nitro-3-(trifluoromethyl)phenyl]-amino}carbonyl)carboxamide |
| 14 | N-{[(2,3-Dichlorophenyl)amino]carbonyl}(1,3-dimethylpyrazolo[5,4-b]-pyridin-5-yl)carboxamide |
| 15 | N-{[(2,6-Dichlorophenyl)amino]carbonyl}(1,3-dimethylpyrazolo[5,4-b]-pyridin-5-yl)carboxamide |
| 16 | N-{[(2,5-Dichlorophenyl)amino]carbonyl}(1,3-dimethylpyrazolo[5,4-b]-pyridin-5-yl)carboxamide |
| 17 | N-{[(3,5-Dichlorophenyl)amino]carbonyl}(1,3-dimethylpyrazolo[5,4-b]-pyridin-5-yl)carboxamide |
| 18 | (1,3-Dimethylpyrazolo[5,4-b]pyridin-5-yl)-N-({[2-chloro-5-(trifluoromethyl)phenyl]-amino}carbonyl)carboxamide |
| 19 | (1,3-Dimethylpyrazolo[5,4-b]pyridin-5-yl)-N-({[4-chloro-2-(trifluoromethyl)phenyl]-amino}carbonyl)carboxamide |
| 20 | (1,3-Dimethylpyrazolo[5,4-b]pyridin-5-yl)-N-({[2-chloro-4-(trifluoromethyl)phenyl)-amino}carbonyl)carboxamide |
| 21 | (1,3-Dimethylpyrazolo[5,4-b]pyridin-5-yl)-N-({[4-chloro-3-(trifluoromethyl)phenyl]-amino}carbonyl)carboxamide |
| 22 | (1,3-Dimethylpyrazolo[5,4-b]pyridin-5-yl)-N-({[2,5-bis(trifluoromethyl)phenyl]-amino}carbonyl)carboxamide |
| 23 | (1,3-Dimethylpyrazolo[5,4-b]pyridin-5-yl)-N-({[3,4-bis(trifluoromethyl)phenyl]-amino}carbonyl)carboxamide |
| 24 | (1,3-Dimethylpyrazolo[5,4-b]pyridin-5-yl)-N-{[3-iodophenyl)amino]carbonyl}-carboxamide |
| 25 | 2-[4-({[[(1,3-Dimethylpyrazolo[5,4-b]pyridin-5-yl)carbonylamino]carbonyl}amino)-2-chlorophenoxy]acetic acid |
| 26 | (1,3-Dimethylpyrazolo[5,4-b]pyridin-5-yl)-N-({[3-(trifluoromethyl)phenyl]amino}-carbonyl)carboxamide |
| 27 | (1,3-Dimethylpyrazolo[5,4-b]pyridin-5-yl)-N-({[4-hydroxy-3-(trifluoromethyl)-phenyl]amino}carbonyl)carboxamide |
| 28 | (1,3-Dimethylpyrazolo[5,4-b]pyridin-5-yl)-N-({[5-hydroxy-3-(trifluoromethyl)-phenyl]amino}carbonyl)carboxamide |
| 29 | 3-({[[(1,3-Dimethylpyrazolo[5,4-b]pyridin-5-yl)carbonylamino]carbonyl}amino)-5-trifluoromethyl)benzoic acid |
| 30 | (1,3-Dimethylpyrazolo[5,4-b]pyridin-5-yl)-N-({[3-(1-methylethoxy)phenyl]-amino}carbonyl)carboxamide |
| 31 | (1,3-Dimethylpyrazolo[5,4-b]pyridin-5-yl)-N-{[(3-phenoxyphenyl)amino]-carbonyl}carboxamide |
| 32 | (1,3-Dimethylpyrazolo[5,4-b]pyridin-5-yl)-N-{[(3-phenylphenyl)amino]-carbonyl}carboxamide |
| 33 | 4-({[[(1,3-Dimethylpyrazolo[5,4-b]pyridin-5-yl)carbonylamino]carbonyl}amino)2-(1-methylethoxy)benzoic acid |
| 34 | Ethyl 2-[4-({[[(1,3-dimethypyrazolo[5,4-b]pyridin-5-yl)carbonylamino]-carbonyl}amino)-2-(trifluoromethyl)phenoxy]acetate |
| 35 | 2-[4-({[[(1,3-Dimethypyrazolo[5,4-b]pyridin-5-yl)carbonylamino]carbonyl}-amino)-2-(trifluoromethyl)phenoxy]acetic acid |

TABLE 5-continued

| Cmpd | Name |
|---|---|
| 36 | (4-Chloro-1,3-dimethylpyrazolo[5,4-b]pyridin-5-yl)-N-{[(3-chlorophenyl)-amino]carbonyl}carboxamide |
| 37 | N-{[(3,4-dichlorophenyl)amino]carbonyl}(4-chloro-1,3-dimethylpyrazolo-[5,4-b]pyridin-5-yl)carboxamide |
| 38 | (4-Chloro-1,3-dimethylpyrazolo[5,4-b]pyridin-5-yl)-N-({[4-(trifluoromethyl)-phenyl]amino}carbonyl)carboxamide |
| 39 | (4-Chloro-1,3-dimethylpyrazolo[5,4-b]pyridin-5-yl)-N-{[(4-chlorophenyl)-amino]carbonyl}carboxamide |
| 40 | Sodium 2-[4-({[(1,3-dimethylpyrazolo[5,4-b]pyridin-5-yl)carbonylamino]-carbonyl}amino)-2-chlorophenoxy]acetate |
| 41 | 4-({[(1,3-Dimethylpyrazolo[5,4-b]pyridin-5-yl)carbonylamino]carbonyl}amino)-benzoic acid |
| 42 | (1,3-Dimethylpyrazolo[5,4-b]pyridin-5-yl)-N-({[3-(trifluoromethyl)phenyl]amino}-carbonyl)carboxamide |

TABLE 6

| Cmpd | Name |
|---|---|
| 43 | N-({[4-Fluoro-3-(trifluoromethyl)phenyl]amino}carbonyl)(4-hydroxy-1,3-dimethylpyrazolo[5,4-b]pyridin-5-yl)carboxamide |
| 44 | [4-(Dimethylamino)-1,3-dimethylpyrazolo[5,4-b]pyridin-5-yl]-N-({[4-fluoro-3-(trifluoromethyl)phenyl]amino}carbonyl)carboxamide |
| 45 | (4-{[2-(Dimethylamino)ethyl]amino}-1,3-dimethylpyrazolo[5,4-b]pyridin-5-yl)-N-({[4-fluoro-3-(trifluoromethyl)phenyl]amino}carbonyl)carboxamide |
| 46 | (4-{[2-(Dimethylamino)ethyl]amino}-1,3-dimethylpyrazolo[5,4-b]pyridin-5-yl)-N-({[4-fluoro-3-(trifluoromethyl)phenyl]amino}carbonyl)carboxamide hydrochloride |
| 47 | (4-{[2-(Dimethylamino)ethyl]methylamino}-1,3-dimethylpyrazolo[5,4-b]pyridin-5-yl)-N-({[4-fluoro-3-(trifluoromethyl)phenyl]amino}carbonyl)carboxamide |
| 48 | (4-{[2-(Dimethylamino)ethyl]methylamino}-1,3-dimethylpyrazolo[5,4-b]pyridin-5-yl)-N-({[4-fluoro-3-(trifluoromethyl)phenyl]amino}carbonyl)carboxamide hydrochloride |
| 49 | (4-{[3-(Dimethylamino)propyl]amino}-1,3-dimethylpyrazolo[5,4-b]pyridin-5-yl)-N-({[4-fluoro-3-(trifluoromethyl)phenyl]amino}carbonyl)carboxamide |
| 50 | (4-{[3-(Dimethylamino)propyl]amino}-1,3-dimethylpyrazolo[5,4-b]pyridin-5-yl)-N-({[4-fluoro-3-(trifluoromethyl)phenyl]amino}carbonyl)carboxamide hydrochloride |
| 51 | {4-[bis(2-Hydroxyethyl)amino]-1,3-dimethylpyrazolo[5,4-b]pyridin-5-yl}-N-({[4-fluoro-3-(trifluoromethyl)phenyl]amino}carbonyl)carboxamide |
| 52 | 1,3-dimethyl-4-[(2-morpholin-4-ylethyl)amino]pyrazolo[5,4-b]pyridin-5-yl}-N-({[4-fluoro-3-(trifluoromethyl)phenyl]amino}carbonyl)carboxamide |
| 53 | {1,3-Dimethyl-4-[methyl(1-methylpyrrolidin-3-yl)amino]pyrazolo[5,4-b]pyridin-5-yl}-N-({[4-fluoro-3-(trifluoromethyl)phenyl]amino}carbonyl)carboxamide |
| 54 | {1,3-Dimethyl-4-[methyl(1-methylpyrrolidin-3-yl)amino]pyrazolo[5,4-b]pyridin-5-yl}-N-({[4-fluoro-3-(trifluoromethyl)phenyl]amino}carbonyl)carboxamide hydrochloride |
| 55 | {4-[(4-Aminocyclohexyl)amino]-1,3-dimethylpyrazolo[5,4-b]pyridin-5-yl}-N-({[4-fluoro-3-(trifluoromethyl)phenyl]amino}carbonyl)carboxamide |
| 56 | {4-[(4-Aminocyclohexyl)amino]-1,3-dimethylpyrazolo[5,4-b]pyridin-5-yl}-N-({[4-fluoro-3-(trifluoromethyl)phenyl]amino}carbonyl)carboxamide hydrochloride |
| 57 | {1,3-Dimethyl-4-[(perhydropyrrolizin-7a-ylmethyl)amino]pyrazolo[5,4-b]pyridin-5-yl}-N-({[4-fluoro-3-(trifluoromethyl)phenyl]amino}carbonyl)carboxamide |
| 58 | {1,3-Dimethyl-4-[(perhydropyrrolizin-7a-ylmethyl)amino]pyrazolo[5,4-b]pyridin-5-yl}-N-({[4-fluoro-3-(trifluoromethyl)phenyl]amino}carbonyl)carboxamide hydrochloride |
| 59 | {1,3-Dimethyl-4-[(2-perhydropyrrolizin-7a-ylethyl)amino]pyrazolo[5,4-b]pyridin-5-yl}-N-({[4-fluoro-3-(trifluoromethyl)phenyl]amino}carbonyl)carboxamide |
| 60 | {1,3-Dimethyl-4-[(2-perhydropyrrolizin-7a-ylethyl)amino]pyrazolo[5,4-b]pyridin-5-yl}-N-({[4-fluoro-3-(trifluoromethyl)phenyl]amino}carbonyl)carboxamide hydrochloride |
| 61 | {1,3-Dimethyl-4-[benzylamino]pyrazolo[5,4-b]pyridin-5-yl}-N-({[4-fluoro-3-(trifluoromethyl)phenyl]amino}carbonyl)carboxamide |
| 62 | {4-[3-(Dimethylamino)pyrrolidinyl]-1,3-dimethylpyrazolo[5,4-b]pyridin-5-yl}-N-({[4-fluoro-3-(trifluoromethyl)phenyl]amino}carbonyl)carboxamide |
| 63 | {4-[3-(Dimethylamino)pyrrolidinyl]-1,3-dimethylpyrazolo[5,4-b]pyridin-5-yl}-N-({[4-fluoro-3-(trifluoromethyl)phenyl]amino}carbonyl)carboxamide hydrochloride |
| 64 | (1,3-Dimethyl-4-piperidylpyrazolo[5,4-b]pyridin-5-yl)-N-({[4-fluoro-3-(trifluoromethyl)phenyl]amino}carbonyl)carboxamide |
| 65 | (1,3-Dimethyl-4-morpholin-4-ylpyrazolo[5,4-b]pyridin-5-yl)-N-({[4-fluoro-3-(trifluoromethyl)phenyl]amino}carbonyl)carboxamide |

TABLE 6-continued

| Cmpd | Name |
|---|---|
| 66 | (1,3-Dimethyl-4-piperazinylpyrazolo[5,4-b]pyridin-5-yl)-N-({[4-fluoro-3-(trifluoromethyl)phenyl]amino}carbonyl)carboxamide |
| 67 | (1,3-Dimethyl-4-piperazinylpyrazolo[5,4-b]pyridin-5-yl)-N-({[4-fluoro-3-(trifluoromethyl)phenyl]amino}carbonyl)carboxamide hydrochloride |
| 68 | [1,3-Dimethyl-4-(4-methylpiperazinyl)pyrazolo[5,4-b]pyridin-5-yl]-N-{[(3-chlorophenyl)amino]carbonyl}carboxamide hydrochloride |
| 69 | [1,3-Dimethyl-4-(4-methylpiperazinyl)pyrazolo[5,4-b]pyridin-5-yl]-N-{[(3-bromophenyl)amino]carbonyl}carboxamide hydrochloride |
| 70 | [1,3-Dimethyl-4-(4-methylpiperazinyl)pyrazolo[5,4-b]pyridin-5-yl]-N-{[(4-chlorophenyl)amino]carbonyl}carboxamide |
| 71 | N-{[(3,4-Dichlorophenyl)amino]carbonyl}[1,3-dimethyl-4-(4-methylpiperazinyl)pyrazolo[5,4-b]pyridin-5-yl]carboxamide |
| 72 | [1,3-Dimethyl-4-(4-methylpiperazinyl)pyrazolo[5,4-b]pyridin-5-yl]-N-({[3-(trifluoromethyl)phenyl]amino}carbonyl)carboxamide |
| 73 | [1,3-Dimethyl-4-(4-methylpiperazinyl)pyrazolo[5,4-b]pyridin-5-yl]-N-({[3-(trifluoromethyl)phenyl]amino}carbonyl)carboxamide hydrochloride |
| 74 | [1,3-Dimethyl-4-(4-methylpiperazinyl)pyrazolo[5,4-b]pyridin-5-yl]-N-({[3-(methylethyl)phenyl]amino}carbonyl)carboxamide hydrochloride |
| 75 | [1,3-Dimethyl-4-(4-methylpiperazinyl)pyrazolo[5,4-b]pyridin-5-yl]-N-({[3-(1-methylethoxy)phenyl]amino}carbonyl)carboxamide hydrochloride |
| 76 | 4-[({[1,3-Dimethyl-4-(4-methylpiperazinyl)pyrazolo[5,4-b]pyridin-5-yl]-carbonylamino}carbonyl)amino]-2-(1-methylethoxy)benzoic acid |
| 77 | [1,3-Dimethyl-4-(4-methylpiperazinyl)pyrazolo[5,4-b]pyridin-5-yl]-N-({[3-(trifluoromethoxy)phenyl]amino}carbonyl)carboxamide, hydrochloride |
| 78 | [1,3-Dimethyl-4-(4-methylpiperazinyl)pyrazolo[5,4-b]pyridin-5-yl]-N-{[(3-(1,3-thiazol-2-yl)phenyl)amino]carbonyl}carboxamide |
| 79 | [1,3-Dimethyl-4-(4-methylpiperazinyl)pyrazolo[5,4-b]pyridin-5-yl]-N-{[(3-(1,3-thiazol-2-yl)phenyl)amino]carbonyl}carboxamide hydrochloride |
| 80 | [1,3-Dimethyl-4-(4-methylpiperazinyl)pyrazolo[5,4-b]pyridin-5-yl]-N-{[(3-phenylphenyl)amino]carbonyl}carboxamide |
| 81 | [1,3-Dimethyl-4-(4-methylpiperazinyl)pyrazolo[5,4-b]pyridin-5-yl]-N-{[(3-phenylphenyl)amino]carbonyl}carboxamide hydrochloride |
| 82 | [1,3-Dimethyl-4-(4-methylpiperazinyl)pyrazolo[5,4-b]pyridin-5-yl]-N-{[(3-phenoxyphenyl)amino]carbonyl}carboxamide |
| 83 | [1,3-Dimethyl-4-(4-methylpiperazinyl)pyrazolo[5,4-b]pyridin-5-yl]-N-({[4-methyl-3-(trifluoromethyl)phenyl]amino}carbonyl)carboxamide hydrochloride |
| 84 | [1,3-Dimethyl-4-(4-methylpiperazinyl)pyrazolo[5,4-b]pyridin-5-yl]-N-({[4-fluoro-3-(trifluoromethyl)phenyl]amino}carbonyl)carboxamide |
| 85 | [1,3-Dimethyl-4-(4-methylpiperazinyl)pyrazolo[5,4-b]pyridin-5-yl]-N-({[4-fluoro-3-(trifluoromethyl)phenyl]amino}carbonyl)carboxamide hydrochloride |
| 86 | [1,3-Dimethyl-4-(4-methylpiperazinyl)pyrazolo[5,4-b]pyridin-5-yl]-N-({[3-fluoro-4-(trifluoromethyl)phenyl]amino}carbonyl)carboxamide |
| 87 | [1,3-Dimethyl-4-(4-methylpiperazinyl)pyrazolo[5,4-b]pyridin-5-yl]-N-({[4-hydroxy-3-(trifluoromethyl)phenyl]amino}carbonyl)carboxamide |
| 88 | [1,3-Dimethyl-4-(4-methylpiperazinyl)pyrazolo[5,4-b]pyridin-5-yl]-N-({[4-hydroxy-3-(trifluoromethyl)phenyl]amino}carbonyl)carboxamide hydrochloride |
| 89 | [1,3-Dimethyl-4-(4-methylpiperazinyl)pyrazolo[5,4-b]pyridin-5-yl]-N-({[3-hydroxy-5-(trifluoromethyl)phenyl]amino}carbonyl)carboxamide |
| 90 | [1,3-Dimethyl-4-(4-methylpiperazinyl)pyrazolo[5,4-b]pyridin-5-yl]-N-({[3-hydroxy-5-(trifluoromethyl)phenyl]amino}carbonyl)carboxamide hydrochloride |
| 91 | [1,3-Dimethyl-4-(4-methylpiperazinyl)pyrazolo[5,4-b]pyridin-5-yl]-N-({[3,5-bis(trifluoromethyl)phenyl]amino}carbonyl)carboxamide hydrochloride |
| 92 | Methylethyl 5-[({[1,3-dimethyl-4-(4-methylpiperazinyl)pyrazolo[5,4-b]pyridin-5-yl]carbonylamino}carbonyl)amino]-2-chlorobenzoate hydrochloride |
| 93 | [1,3-Dimethyl-4-(4-methylpiperazinyl)pyrazolo[5,4-b]pyridin-5-yl]-N-({[3-(phenylcarbonyl)phenyl]amino}carbonyl)carboxamide hydrochloride |
| 94 | [1,3-Dimethyl-4-(4-methylpiperazinyl)pyrazolo[5,4-b]pyridin-5-yl]-N-({[3-chloro-4-(morpholin-4-ylcarbonyl)phenyl]amino}carbonyl)carboxamide |
| 95 | [1,3-Dimethyl-4-(4-methylpiperazinyl)pyrazolo[5,4-b]pyridin-5-yl]-N-({[4-chloro-3-(morpholin-4-ylcarbonyl)phenyl]amino}carbonyl)carboxamide hydrochloride |
| 96 | [1,3-Dimethyl-4-(4-methylpiperazinyl)pyrazolo[5,4-b]pyridin-5-yl]-N-[({4-chloro-3-[(4-methylpiperazinyl)carbonyl]phenyl}amino)carbonyl]carboxamide |
| 97 | [1,3-Dimethyl-4-(4-methylpiperazinyl)pyrazolo[5,4-b]pyridin-5-yl]-N-[({3-chloro-4-[(4-methylpiperazinyl)carbonyl]phenyl}amino)carbonyl]carboxamide |
| 98 | [4-(4,4-Dimethylpiperazinyl)-1,3-dimethylpyrazolo[5,4-b]pyridin-5-yl]-N-({[4-fluoro-3-(trifluoromethyl)phenyl]amino}carbonyl)carboxamide iodide |
| 99 | [4-(4-Ethylpiperazinyl)-1,3-dimethylpyrazolo[5,4-b]pyridin-5-yl]-N-({[4-fluoro-3-(trifluoromethyl)phenyl]amino}carbonyl)carboxamide |
| 100 | [4-(4-Ethylpiperazinyl)-1,3-dimethylpyrazolo[5,4-b]pyridin-5-yl]-N-({[4-fluoro-3-(trifluoromethyl)phenyl]amino}carbonyl)carboxamide hydrochloride |
| 101 | N-({[4-Fluoro-3-(trifluoromethyl)phenyl]amino}carbonyl){4-[4-(2-hydroxyethyl)-piperazinyl]-1,3-dimethylpyrazolo[5,4-b]pyridin-5-yl}carboxamide |
| 102 | N-({[4-Fluoro-3-(trifluoromethyl)phenyl]amino}carbonyl){4-[4-(2-hydroxyethyl)-piperazinyl]-1,3-dimethylpyrazolo[5,4-b]pyridin-5-yl}carboxamide hydrochloride |
| 103 | [1,3-Dimethyl-4-(4-phenylpiperazinyl)pyrazolo[5,4-b]pyridin-5-yl]-N-({[4-fluoro-3-(trifluoromethyl)phenyl]amino}carbonyl)carboxamide |

TABLE 6-continued

| Cmpd | Name |
|---|---|
| 104 | {1,3-Dimethyl-4-[4-benzylpiperazinyl]pyrazolo[5,4-b]pyridin-5-yl}-N-({[4-fluoro-3-(trifluoromethyl)phenyl]amino}carbonyl)carboxamide |
| 105 | {1,3-Dimethyl-4-[4-benzylpiperazinyl]pyrazolo[5,4-b]pyridin-5-yl}-N-({[4-fluoro-3-(trifluoromethyl)phenyl]amino}carbonyl)carboxamide hydrochloride |
| 106 | 4-Amino-1-{5-[N-({[4-fluoro-3-(trifluoromethyl)phenyl]amino}carbonyl)-carbamoyl]-1,3-dimethylpyrazolo[5,4-b]pyridin-4-yl}pyridinium chloride |
| 107 | [1,3-Dimethyl-4-(4-methyl(1,4-diazaperhydroepinyl))pyrazolo[5,4-b]pyridin-5-yl]-N-({[4-fluoro-3-(trifluoromethyl)phenyl]amino}carbonyl)carboxamide |
| 108 | [1,3-Dimethyl-4-(4-methyl(1,4-diazaperhydroepinyl))pyrazolo[5,4-b]pyridin-5-yl]-N-({[4-fluoro-3-(trifluoromethyl)phenyl]amino}carbonyl)carboxamide hydrochloride |
| 109 | N-({[4-Fluoro-3-(trifluoromethyl)phenyl]amino}carbonyl)-(6-hydroxy-1,3-dimethylpyrazolo[5,4-b]pyridin-5-yl)carboxamide |
| 110 | [1,3-Dimethyl-6-(1-methylethoxy)pyrazolo[5,4-b]pyridin-5-yl]-N-({[4-fluoro-3-(trifluoromethyl)phenyl]amino}carbonyl)carboxamide |
| 111 | [1,3-Dimethyl-6-(phenylmethoxy)pyrazolo[5,4-b]pyridin-5-yl]-N-({[4-fluoro-3-(trifluoromethyl)phenyl]amino}carbonyl)carboxamide |
| 112 | N-({[4-Fluoro-3-(trifluoromethyl)phenyl]amino}carbonyl)-(6-methoxy-1,3-dimethylpyrazolo[5,4-b]pyridin-5-yl)carboxamide |
| 113 | (1,3-Dimethyl-6-morpholin-4-ylpyrazolo[5,4-b]pyridin-5-yl)-N-({[4-fluoro-3-(trifluoromethyl)phenyl]amino}carbonyl)carboxamide |
| 114 | [6-(Dimethylamino)-1,3-dimethylpyrazolo[5,4-b]pyridin-5-yl]-N-({[4-fluoro-3-(trifluoromethyl)phenyl]amino}carbonyl)carboxamide |
| 115 | [1,3-Dimethyl-6-(4-methylpiperazinyl)pyrazolo[5,4-b]pyridin-5-yl]-N-({[4-fluoro-3-(trifluoromethyl)phenyl]amino}carbonyl)carboxamide hydrochloride |
| 116 | (6-{[2-(Dimethylamino)ethyl]methylamino}-1,3-dimethylpyrazolo[5,4-b]pyridin-5-yl)-N-({[4-fluoro-3-(trifluoromethyl)phenyl]amino}carbonyl)carboxamide hydrochloride |
| 117 | {6-[2-(Dimethylamino)ethoxy]-1,3-dimethylpyrazolo[5,4-b]pyridin-5-yl}-N-({[4-fluoro-3-(trifluoromethyl)phenyl]amino}carbonyl)carboxamide hydrochloride |
| 118 | {6-[2-(Dimethylamino)-isopropoxy]-1,3-dimethylpyrazolo[5,4-b]pyridin-5-yl}-N-({[4-fluoro-3-(trifluoromethyl)phenyl]amino}carbonyl)carboxamide hydrochloride |
| 119 | {6-[3-(Dimethylamino)propoxy]-1,3-dimethylpyrazolo[5,4-b]pyridin-5-yl}-N-({[4-fluoro-3-(trifluoromethyl)phenyl]amino}carbonyl)carboxamide hydrochloride |
| 120 | {6-[2-(Diethylamino)ethoxy]-1,3-dimethylpyrazolo[5,4-b]pyridin-5-yl}-N-({[4-fluoro-3-(trifluoromethyl)phenyl]amino}carbonyl)carboxamide hydrochloride |
| 121 | [1,3-Dimethyl-6-(2-pyrrolidinylethoxy)pyrazolo[5,4-b]pyridin-5-yl]-N-({[4-fluoro-3-(trifluoromethyl)phenyl]amino}carbonyl)carboxamide hydrochloride |
| 122 | [1,3-Dimethyl-6-(2-piperidylethoxy)pyrazolo[5,4-b]pyridin-5-yl]-N-({[4-fluoro-3-(trifluoromethyl)phenyl]amino}carbonyl)carboxamide hydrochloride |
| 123 | N-({[4-Fluoro-3-(trifluoromethyl)phenyl]amino}carbonyl)-(1-methyl-3-phenyl-pyrazolo[5,4-b]pyridin-5-yl)carboxamide |
| 124 | N-({[4-Fluoro-3-(trifluoromethyl)phenyl]amino}carbonyl)-(1-methyl-pyrazolo[5,4-b]pyridin-5-yl)carboxamide |
| 125 | N-({[4-Fluoro-3-(trifluoromethyl)phenyl]amino}carbonyl)-(3-methyl-1-phenyl-pyrazolo[5,4-b]pyridin-5-yl)carboxamide |
| 126 | N-({[4-Fluoro-3-(trifluoromethyl)phenyl]amino}carbonyl)-[4-(4-methylpiperazinyl)-1,3-diphenylpyrazolo[5,4-b]pyridin-5-yl]carboxamide |
| 127 | N-({[4-Fluoro-3-(trifluoromethyl)phenyl]amino}carbonyl)-[4-(4-methylpiperazinyl)-1,3-diphenylpyrazolo[5,4-b]pyridin-5-yl]carboxamide hydrochloride |
| 128 | N-({[4-Fluoro-3-(trifluoromethyl)phenyl]amino}carbonyl)-[1-methyl-4-(4-methylpiperazinyl)-3-phenylpyrazolo[5,4-b]pyridin-5-yl]carboxamide |
| 129 | N-({[4-Fluoro-3-(trifluoromethyl)phenyl]amino}carbonyl)-[1-methyl-4-(4-methylpiperazinyl)-3-phenylpyrazolo[5,4-b]pyridin-5-yl]carboxamide hydrochloride |
| 130 | N-({[4-Fluoro-3-(trifluoromethyl)phenyl]amino}carbonyl)-(1,3,6-trimethylpyrazolo[5,4-b]pyridin-5-yl)carboxamide |
| 131 | Ethyl 1-{1,3-dimethyl-5-[N-({[3-(1-methylethoxy)phenyl]amino}carbonyl)-carbamoyl]pyrazolo[5,4-b]pyridin-4-yl}piperidine-4-carboxylate |
| 132 | tert-Butyl 2-({1,3-dimethyl-5-[N-({[3-(1-methylethoxy)phenyl]amino}carbonyl)-carbamoyl]pyrazolo[5,4-b]pyridin-4-yl}amino)acetate carboxamide |
| 133 | tert-Butyl 2-({1,3-dimethyl-5-[N-({[3-(1-methylethoxy)phenyl]amino}carbonyl)-carbamoyl]pyrazolo[5,4-b]pyridin-4-yl}methylamino)acetate |
| 134 | N-({[4-Fluoro-3-(trifluoromethyl)phenyl]amino}carbonyl)-[3-methyl-4-(4-methylpiperazinyl)isoxazolo[5,4-b]pyridin-5-yl]carboxamide |
| 135 | N-({[4-Fluoro-3-(trifluoromethyl)phenyl]amino}carbonyl)-[3-methyl-4-(4-methylpiperazinyl)isoxazolo[5,4-b]pyridin-5-yl]carboxamide hydrochloride |
| 136 | [4-(Dimethylamino)-3-methylisoxazolo[5,4-b]pyridin-5-yl]-N-({[4-fluoro-3-(trifluoromethyl)phenyl]amino}carbonyl)carboxamide |
| 137 | (4-{[2-(Dimethylamino)ethyl]methylamino}-3-methylisoxazolo[5,4-b]pyridin-5-yl)-N-({[4-fluoro-3-(trifluoromethyl)phenyl]amino}carbonyl)carboxamide |

TABLE 6-continued

| Cmpd | Name |
|---|---|
| 138 | (4-{[2-(Dimethylamino)ethyl]methylamino}-3-methylisoxazolo[5,4-b]pyridin-5-yl)-N-({[4-fluoro-3-(trifluoromethyl)phenyl]amino}carbonyl)carboxamide hydrochloride |
| 139 | N-({[4-Fluoro-3-(trifluoromethyl)phenyl]amino}carbonyl)-(3-methyl-4-morpholin-4-ylisoxazolo[5,4-b]pyridin-5-yl)carboxamide |
| 140 | (6-{[2-(Dimethylamino)ethyl]methylamino}-1,3-dimethylpyrazolo[5,4-b]pyridin-5-yl)-N-({[3-(1-methylethoxy)phenyl]amino}carbonyl)carboxamide |
| 141 | (1,3-Dimethylpyrazolo[5,4-b]pyridin-5-yl)-N-({[3-chloro-4-(morpholin-4-yl-carbonyl)phenyl]amino}carbonyl)carboxamide |
| 142 | (1,3-dimethylpyrazolo[5,4-b]pyridin-5-yl)-N-[({3-chloro-4-[(4-methylpiperazinyl)-carbonyl]phenyl}amino)carbonyl]carboxamide |

Example 16

Inhibition of MCP-1-Induced Chemotaxis

A 96-well microchemotaxis chamber with a 5 μm-pore size, PVP-coated polycarbonate filter membrane (Neuro Probe Inc., Cabin John, Md.) was used for testing. Compounds were prepared as 10 mM stock solution in DMSO. THP-1 cells ($2 \times 10^6$ cells/mL) were labeled with 5 μM Calcein AM containing 0.1% F127 (Molecular Probe, Eugene, Oreg.) at 37° C. for 30 min, and then pretreated with compound at room temperature for an additional 30 min. The lower chamber was loaded with medium containing 12.5 nM hMCP-1. The filter membrane was placed over the lower chamber, followed by a silicon gasket and the upper chamber. The pretreated THP-1 cell ($4 \times 10^5$ cells/50 μL of RPMI1640 medium per well) were added to the upper chamber and incubated in 5% $CO_2$ at 37° C. for 2 h. The migrated cells were determined with a fluorescent plate reader (LJL BioSystems, Sunnyvale, Calif.) Table 7 shows the $IC_{50}$ (concentration of compound that inhibited migration of 50% of the cell relative to control) for several compounds of the present invention.

TABLE 7

Effect of Selected Compounds on MCP-1 Induced Chemotaxis

| Compound | $IC_{50}$ (μM) |
|---|---|
| 2 | 0.8 |
| 8 | 8.1 |
| 10 | 2.0 |
| 11 | 12.5 |
| 16 | 10.1 |
| 37 | 12.7 |
| 39 | 3.0 |

Example 17

Thioglycollate-Induced Inflammation Model

3% Brewer's thioglycollate broth (Difco, Detroit, Mich.) was injected into the peritoneal cavity of ICR male mice, followed by subcutaneous administration of the test compound. The same dose of test compound was again administered immediately after the broth injection and 3 h later. After 72 h, the number of total elicited cells and MOMA2-positive cells in the peritoneal cavity was analyzed using an EPICS XL Beckman Coulter. The results are shown in Table 8.

TABLE 8

Effect of Compound 11 on a Thioglycollate-Induced Inflammation Model

| Compound | Dose (mg/kg) | Total Cells (× $10^6$) | MOMA2-positive Cells (× $10^6$) |
|---|---|---|---|
| No treatment | — | 2.1 ± 0.3** | 1.2 ± 0.2** |
| Control | — | 24.4 ± 1.1 | 18.5 ± 0.9 |
| 11 | 5 | 19.7 ± 1.6 | 14.3 ± 1.2* |
| Anti-MCP-1 Ab | 1 | 12.3 ± 1.8** | 8.8 ± 1.2** |

Anti-MCP-1 Ab was intraperitoneally injected.
Significant difference from control group:
*$P < 005$,
**$P < 0.01$ (ANOVA).

Example 18

Thioglycollate-Induced Inflammation Model

3% Brewer's thioglycollate broth (Difco, Detroit, Mich.) was injected into the peritoneal cavity of ICR male mice, followed by subcutaneous administration of the test compound. The same dose of test compound was again administered immediately after the broth injection and 3 h later. After 72 h, the number of total elicited cells and MOMA2-positive cells in the peritoneal cavity was analyzed using an EPICS XL Beckman Coulter. The results are shown in Table 9.

TABLE 9

Effect of Compounds on a Thioglycollate-Induced Inflammation Model

| Compound | Dose (mg/kg) | Total Cells (× $10^6$) | MOMA2-positive Cells (× $10^6$) |
|---|---|---|---|
| No treatment | — | 1.9 ± 0.2** | 0.9 ± 0.1** |
| Control | — | 9.6 ± 0.7 | 7.8 ± 0.6 |
| 142 | 10 | 7.5 ± 1.2 | 5.5 ± 0.4 |
| 140 | 10 | 7.3 ± 1.1 | 5.2 ± 0.6* |
| 116 | 10 | 4.2 ± 1.1* | 3.0 ± 0.8** |
| 97 | 2 | 6.4 ± 0.6 | 4.1 ± 0.3** |

Significant difference from control group:
*$P < 0.05$,
**$P < 0.01$ (Least Significant Difference Method).

Example 19

Anti-Thy-1 Antibody-Induced Nephritis Model

The efficacy of the compounds of the present invention was also evaluated in an animal model of nephritis. This model very closely simulates the conditions found in human mesangial proliferative glomerulonephritis.

Anti-Thy-1 nephritis was induced by intravenous injection of anti-Thy-1-antibody to male Wistar rats. The test compound was subcutaneously administered 2 h before, immediately after, and 5 h after the anti-Thy-1 antibody treatment, and then twice a day for the following 2 days. Anti-MCP-1 antibody was intraperitoneally injected once a day for 3 days. Seven days after the anti-Thy-1 antibody treatment, the rats were sacrificed. The kidneys were perfused with 10% formaldehyde in PBS, surgically removed, and immersed in 10% formaldehyde. The kidneys were then embedded in paraffin for glomerular histopathology or in OCT compound (Miles Inc., Elkhart, Ind.) in liquid nitrogen after immersion in 30% sucrose overnight. Immunohistochemical staining was performed with a mouse anti-rat ED-1 monoclonal antibody. Briefly, 5 μm renal sections were prepared and endogenous peroxidase blocked with 0.3% hydrogen peroxide. The sections were then blocked with Protein Block (DAKO, Japan) and stained with anti-ED-1 antibody for 45 min. The ED-1 antigen was visualized by peroxidase-labeled anti-mouse IgG and diaminobenzidine. The amount of urinary protein was determined with the DC protein assay kit (Bio-rad, Hercules, Calif.). The effect of a representative test compound on the level of urinary protein excretion and the infiltration of ED-1 positive cells into the glomeruli is shown in Table 10.

TABLE 10

Effect of Compound 11 on Anti-Thy-1 Antibody Induced Nephritis

| Compound | Dose (mg/kg) | Urinary protein (mg/day) | ED-1 positive cells/glomeruli (mean ± SE) |
|---|---|---|---|
| No treatment | — | 20.5 ± 3.4** | 0.2 ± 0.1 |
| Control | — | 277.8 ± 24.2 | 7.8 ± 1.1 |
| 11 | 0.1 | 182.2 ± 28.0 | 5.3 ± 0.7 |
| 11 | 2 | 117.4 ± 26.3 | 2.3 ± 0.6** |
| Anti-MCP-1 Ab | 1 | 137.2 ± 57.4** | 6.2 ± 0.9 |

Significant difference from control group:
**$P < 0.01$ (ANOVA).

Example 20

Apolipoprotein E-Deficient Mouse Model

Apolipoprotein E (apoE) is a component of several plasma lipoproteins, including chylomicrons, VLDL, and HDL. Receptor-mediated catabolism of these lipoprotein particles is mediated through the interaction of apoE with the LDL receptor (LDLR) or with LDLR-related protein (LRP). ApoE-deficient mice exhibit hypercholesterolemia and develop complex atheromatous lesions similar to those seen in humans. The efficacy of the compounds of the present invention was also evaluated using this animal model.

Male, 4 week-old apoE-deficient mice were fed on high-fat diet (15% fat, 1.25% cholesterol. The test compound was administered as food admixture for 8 weeks. At 12 week-old, the mice were fasted for 4 hours and then sacrificed under ether anesthesia. Blood was collected in the presence of heparin, and the hearts were perfused in situ with PBS (pH 7.4), followed by 4% paraformaldehyde for 5 min.

To determine cross-sectional lesion areas, the hearts were embedded in OCT compound and sectioned at 10 μm using cryostat. The sections were stained with oil red O. Each section of the aortic valve was evaluated for oil red O staining by capturing images directly from a RGB camera attached to a light microscope; image analysis was performed with the IPAP-WIN software (Sumika Tekuno, Japan). Five sections were examined for each animal, and the sum of the lesion areas was calculated and expressed as the percent of the total cross-sectional wall area. Total cholesterol was determined with a Determiner assay kit (Kyowa medex, Japan).

The effect of a representative test compound in this animal model of atherosclerosis is shown in Table 11.

TABLE 11

Effect of Compound 11 on the ApoE-Deficient Mouse Model of Atherosclerosis

| Compound | Dose (mg/kg) | % Atherosclerotic Lesion (mean ± SD) |
|---|---|---|
| Control | — | 25.08 ± 6.93 |
| 11 | 10 | 18.72 ± 5.27* |

Significant difference from control group:
*$P < 0.05$ (t-test).

Compound 11 reduced the percent of atherosclerotic lesion area and this reduction was statistically significant. There were no significant differences in plasma total cholesterol level and body weight between the control and the test compound-treated groups (data not shown).

Example 21

Inhibition of MCP-1-Induced Chemotaxis

A 48-well microchemotaxis chamber with a 5 μm-pore size, PVP-coated polycarbonate filter membrane (Neuro Probe Inc., Cabin John, Md.) was used for testing. Compounds were prepared as 10 mM stock solution in DMSO. THP-1 cells were washed with RPMI 1640 medium supplemented with 0.5% BSA and 25 mM HEPES, pH 7.4, and suspended at a density of $4 \times 10^6$ cells/mL in the same medium A 150 μL aliquot of this suspension was treated with an equal volume of test compound solution and the mixture incubated at 37° C. for 15 min. The lower chamber was loaded with 26 μL of a 2.5 nM solution of hMCP-1 (PeproTech) in medium. The filter was placed over the lower chamber, followed by a silicon rubber gasket and the upper chamber. 50 μL aliquot of the THP-1 cell suspension containing the test compound was added to the upper chamber and the assembly incubated in a 5% $CO_2$ atmosphere at 37° C. for 2 hr. The chamber was then disassembled and the cells remaining on the upper surface of the filter were scrapped off with a rubber scrapper. The filter was fixed with methanol, stained with Diff-Quik solution, and mounted on a slide glass. The cells that had migrated across the filter onto the lower surface were then counted by microscopic observation. Table 12 shows the $IC_{50}$ (concentration of compound that inhibited migration of 50% of the cells relative to control) for several compounds of the present invention.

TABLE 12

Effect of Selected Compounds on MCP-1-Induced Chemotaxis

| Cmpd | IC$_{50}$ (μM) |
|---|---|
| 43 | 7.7 |
| 44 | 8.2 |
| 46 | 2 |
| 48 | 2 |
| 50 | 10 |
| 51 | 1.6 |
| 54 | 0.4 |
| 56 | 0.4 |
| 58 | 10 |
| 60 | 1.2 |
| 61 | 20 |
| 63 | 1.2 |
| 64 | 2 |
| 65 | 10 |
| 67 | 1.8 |
| 68 | 4 |
| 69 | 4 |
| 70 | 4 |
| 71 | 4 |
| 72 | 3.6 |
| 73 | 1.7 |
| 74 | 4 |
| 75 | 0.7 |
| 76 | 4 |
| 77 | 0.7 |
| 78 | 0.9 |
| 79 | 3 |
| 80 | 4 |
| 81 | 4 |
| 83 | 4 |
| 85 | 0.09 |
| 87 | 4 |
| 88 | 4 |
| 89 | 4 |
| 90 | 4 |
| 91 | 3 |
| 92 | 2.1 |
| 94 | 1.2 |
| 95 | 1.9 |
| 97 | 1.1 |
| 100 | 0.38 |
| 102 | 2 |
| 103 | 2 |
| 105 | 2 |
| 106 | 0.4 |
| 108 | 2 |

Example 22

Adjuvant Arthritis Model in Rat

Adjuvant arthritis was induced in male Lewis rats as follows. Complete Freund's adjuvant (CFA) was mixed with PBS and 0.1 ml of the resulting emulsion was injected subcutaneously into the foot pad of the right hind paw (day=0). The test compound was administered p.o. at day 0 and then once a day for 26 days. Paw swelling was measured by the increased thickness of the foot pad. Table 13 shows the change in the foot pad edema expressed as percent swelling relative to the pad thickness on day 0.

TABLE 13

Effect of Compound 85 on the Adjuvant Arthritis Model

| Compound | Dose (mg/kg) | Percent Swelling Days after immunization | | | | | |
|---|---|---|---|---|---|---|---|
| | | 11 | 14 | 17 | 21 | 22 | 26 |
| No treatment | — | 8 | 12 | 9 | 12 | 10 | 8 |
| Control | — | 38 | 46 | 45 | 48 | 42 | 40 |
| 85 | 10 | 39 | 40 | 34 | 30 | 26 | 27 |

Example 23

Collagen-induced Arthritis Model in Rat

Collagen-induced arthritis was induced in female Lewis rats as follows. Rats were injected subcutaneously with the emulsion of bovine collagen type II (3.3 mg/kg at day 0 and 1.67 mg/kg at day 7) and complete Freund's adjuvant (CFA) at the base of the tail at day 0 and immunized additionally at day 7. The test compounds were administered i.p. at day 0 and then once a day for 18 days or p.o. (methotrexate) at day 0 and then 3 times a week until day 18. Paw swelling was measured by the increased volume of the legs using a plethysmometer. Table 14 shows the change in the swelling expressed as percent swelling relative to the volume of legs on day 0.

TABLE 14

Effect of Compounds on the Collagen-induced Arthritis Model

| Compound | Dose (mg/kg) | Percent Swelling day 18 |
|---|---|---|
| No treatment | — | 16.2 ± 2.8 |
| Control | — | 39.4 ± 11.7 |
| 141 | 10 | 12.3 ± 1.5* |
| Methotrexate | 1 | 8.9 ± 1.2* |

Significant difference from control group:
*$P < 0.05$,
** $P < 0.01$ (Least Significant Difference Method).

Example 24

Collagen-induced Arthritis Model in Rat

Collagen-induced arthritis was induced in female Lewis rats as follows. Rats were injected subcutaneously with the emulsion of bovine collagen type II (3.3 mg/kg at day 0 and 1.67 mg/kg at day 7) and complete Freund's adjuvant (CFA) at the base of the tail at day 0 and immunized additionally at day 7. The test compounds were administered p.o. at day 0 and then twice a day for 21 days or 3 times a week until day 21 was also administered p.o. from day 13 to day 21 in another group. Paw swelling was measured by the increased volume of the legs using a plethysmometer. Table 15 shows the change in the swelling expressed as percent swelling relative to the volume of legs on day 0.

TABLE 15

Effect of Compounds on the Collagen-induced Arthritis Model

| Compound | Dose (mg/kg) | Percent Swelling day 14 | Percent Swelling day 21 |
|---|---|---|---|
| No treatment | — | 8.1 ± 1.0** | 6.7 ± 1.2** |
| Control | — | 28.8 ± 6.1 | 77.7 ± 4.8 |
| 142 | 10 | 12.8 ± 3.6* | 61.2 ± 9.1* |
| 140 | 2 | 14.2 ± 3.3* | 49.2 ± 14.1* |
| 140 | 10 | 7.5 ± 1.0** | 28.0 ± 6.4** |
| Methotrexate | 1 | −0.4 ± 1.1** | −0.7 ± 1.0** |
| 140 (day 13-) | 10 | 10.1 ± 1.6** | 73.5 ± 6.3 |

Significant difference from control group:
*$P < 0.05$,
**$P < 0.01$ (Least Significant Difference Method).
Methotrexate is used as a positive control.

Example 25

Restenosis Model in Rat

Effects of MCP-1 antagonists on rat carotid artery responses to the balloon catheter injury.

Male, 8 weeks old Sprague-Dawley rats were anaesthetized with sodium pentobarbital (50 mg/kg, i.p.) The endothelium of the left common carotid artery was denuded by 3 passages of an inflated 2F Fogarty embolectomy catheter. Test compounds were administered as food admixture to 7 days prior to balloon injury and continued for 14 days after injury. Two weeks after injury, rats were sacrificed under ether anesthesia. The carotid arteries were removed and fixed with 10% neutral buffered formalin for 24 hours. To determine cross-sectional lesion areas, the carotid arteries were embedded in paraffin and sectioned 4~6 μm. Four cross sections of each artery were stained with elastic van Gieson. Intimal and medial areas were measured by a computer-based image analyzing system (IPAP-WIN, Sumika Technos). Serum MCP-1 volume was determined with rat MCP-1 ELISA kit (Cosmo Bio).

TABLE 16

Intimal and Medial areas of rat carotid arteries 14 days after balloon injury.

| Compound | Dose (mg/kg) | n | Intima/media ratio (%) |
|---|---|---|---|
| Control | — | 10 | 1.096 ± 0.067 |
| 11 | 6 | 7 | 0.830 ± 0.072* |

Data are shown as mean ± SE.
*, ***Significantly different from the control at $p < 0.05$ and $p < 0.001$, respectively.

Example 26

Anti-Thy-1 Antibody Induced Nephritis Model

Anti-Thy-1 nephritis was induced by intravenous injection of anti-Thy-1-antibody to male Wistar rats. The test compound was per os administered 2 h before, immediately after, and 5 h after the anti-Thy-1 antibody treatment, and then twice a day for the following 2 days. Seven days after the anti-Thy-1 antibody treatment, the rats were sacrificed. The amount of urinary protein was determined with the DC protein assay kit (Bio-Rad, Hercules, Calif.). The effect of a representative test compound on the level of urinary protein excretion is shown in Table 17.

TABLE 17

[a] Effect of Compound on Anti-Thy-1 Antibody Induced Nephritis

| Compound | Dose (mg/kg) | Urinary Protein (mg/mg creatinine) |
|---|---|---|
| No treatment | — | 4.6 ± 1.1** |
| Control | — | 36.0 ± 9.2 |
| 85 | 0.1 | 33.4 ± 5.1 |
| 85 | 1 | 32.4 ± 5.9 |
| 85 | 10 | 23.5 ± 7.2 |

Example 27

Oral Pharmaceutical Composition—Solid Dosage Formulation

A pharmaceutical composition for oral administration may be prepared by combining the following:

| | % w/w |
|---|---|
| Compound of this invention | 10.0 |
| Magnesium stearate | 0.5 |
| Starch | 2.0 |
| Hydroxypropylmethylcellulose | 1.0 |
| Microcrystalline cellulose | 86.5 |

The mixture may be compressed into tablets, or filled into hard gelatin capsules. The tablet may be coated by applying a suspension of film former (e.g., hydroxypropylmethylcellulose), pigment (e.g., titanium dioxide) and plasticiser (e.g., diethyl phthalate) and drying the film by evaporation of the solvent. The film coat can comprise 2.0% to 6.0% of the tablet weight, preferably about 3.0%.

Example 28

Oral Pharmaceutical Composition Preparation—Capsule

A pharmaceutical composition of a compound of the invention suitable for oral administration may also be prepared by combining the following:

| | % w/w |
|---|---|
| Compound of this invention | 20 |
| Polyethylene glycol 400 | 80 |

The medicinal compound is dispersed or dissolved in the liquid carrier, with a thickening agent added, if required. The formulation is then enclosed in a soft gelatin capsule by suitable technology.

Example 29

Pharmaceutical Composition for Parenteral Administration

A pharmaceutical composition for parenteral administration may be prepared by combining the following:

|  | % w/w |
|---|---|
| Compound of this invention | 1.0 |
| Saline | 99.0 |

The solution is sterilized and sealed in sterile containers.

Various modifications and variations of the present invention will be apparent to those sidled in the art without departing from the scope and spirit of the invention. Although the invention has been described in connection with specific preferred embodiments, it should be understood that the invention as disclosed should not be unduly limited to such specific embodiments. Various modifications of the described modes for carrying out the invention which are obvious to those skilled in the art are intended to be within the scope of this invention.

We claim:

1. A compound of formula A or formula B:

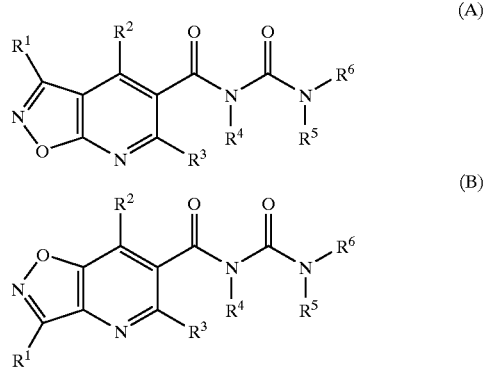

where $R^1$, $R^2$, and $R^3$ are independently, hydrogen, or optionally substituted lower alkyl, alkenyl, alkynyl, cycloalkyl, cycloalkyl(lower alkyl), optionally substituted heterocycloalkyl, optionally substituted aryl, optionally substituted heteroaryl, optionally substituted aryl(lower alkyl), halo(lower alkyl), —$CF_3$, halogen, nitro, —CN, —$OR^9$, —$SR^9$, —$NR^9R^{10}$, —$NR^9$(carboxy(lower alkyl)), —C(=O)$R^9$, —C(=O)$OR^9$, —C(=O)$NR^9R^{10}$, —OC(=O)$R^9$, —$SO_2R^9$, —$OSO_2R^9$, —$SO_2NR^9R^{10}$, —$NR^9SO_2R^{10}$ or —$NR^9C(=O)R^{10}$, where $R^9$ and $R^{10}$ are independently, hydrogen, optionally substituted lower alkyl, lower alkyl-N($C_{1-2}$ alkyl)$_2$, lower alkyl(optionally substituted heterocycloalkyl), alkenyl, alkynyl, optionally substituted cycloalkyl, cycloalkyl(lower alkyl), optionally substituted heterocycloalkyl(lower alkyl), aryl(lower alkyl), optionally substituted aryl, optionally substituted aryloxy, heteroaryl, heteroaryl(lower alkyl), or $R^9$ and $R^{10}$ together are —(CH$_2$)$_{4-6}$— optionally interrupted by one O, S, NH, N-(aryl), N-(aryl(lower alkyl)), N-(carboxy(lower alkyl)) or N-(optionally substituted $C_{1-2}$ alkyl) group, $R^4$ and $R^5$ are independently, hydrogen or lower alkyl, $R^6$ is hydrogen, optionally substituted lower alkyl, alkenyl, alkynyl, cycloalkyl, cycloalkyl(lower alkyl), optionally substituted heterocycloalkyl, optionally substituted aryl, optionally substituted aryl(lower alkyl), optionally substituted heteroaryl, optionally substituted heteroaryl(lower alkyl), —C(=O)$R^{11}$, —C(=O) $OR^{11}$, —C(=O)$NR^{11}R^{12}$, —$SO_2R^{11}$, or —$SO_2NR^{11}R^{12}$, where $R^{11}$ and $R^{12}$ are independently, hydrogen, optionally substituted lower alkyl, alkenyl, alkynyl, cycloalkyl, cycloalkyl(lower alkyl), aryl, optionally substituted aryloxy, heteroaryl, heteroaryl (lower alkyl), or $R^{11}$ and $R^{12}$ together are —(CH$_2$)$_{4-6}$—, or a pharmaceutically acceptable salt thereof, optionally in the form of a single stereoisomer or mixture of stereoisomers thereof.

2. The compound of claim 1, where said compound is a compound of Formula A or a pharmaceutically acceptable salt thereof, optionally in the form of a single stereoisomer or mixture of stereoisomers thereof.

3. The compound of claim 1, where said compound is a compound of Formula B or a pharmaceutically acceptable salt thereof, optionally in the form of a single stereoisomer or mixture of stereoisomer thereof.

4. The compound of claim 1, where $R^1$ is hydrogen, optionally substituted lower alkyl, optionally substituted heterocycloalkyl, optionally substituted aryl, optionally substituted heteroaryl, optionally substituted aryl(lower alkyl), halogen, —$OR^9$, —$NR^9R^{10}$, —C(=O)$OR^9$, —C(=O) $NR^9R^{10}$, —$SO_2NR^9R^{10}$, or —$NR^9C(=O)R^{10}$, where $R^9$ and $R^{10}$ are independently, hydrogen, optionally substituted lower alkyl, lower alkyl-N($C_{1-2}$ alkyl)$_2$, lower alkyl(optionally substituted heterocycloalkyl), aryl(lower alkyl), optionally substituted aryl, heteroaryl, or heteroaryl(lower alkyl).

5. The compound of claim 4, where $R^1$ is optionally substituted lower alkyl, optionally substituted heterocycloalkyl, optionally substituted aryl, optionally substituted heteroaryl, optionally substituted aryl(lower alkyl), halogen, —$OR^9$, —$NR^9R^{10}$, —C(=O)$OR^9$, —C(=O)$NR^9R^{10}$, —$SO_2NR^9R^{10}$, or —$NR^9C(=O)R^{10}$, where $R^9$ and $R^{10}$ are independently, hydrogen, optionally substituted lower alkyl, lower alkyl-N($C_{1-2}$ alkyl)$_2$, lower alkyl(optionally substituted heterocycloalkyl), aryl(lower alkyl), optionally substituted aryl, heteroaryl, or heteroaryl(lower alkyl).

6. The compound of claim 1, where $R^2$ is hydrogen, optionally substituted lower alkyl, cycloalkyl, optionally substituted heterocycloalkyl, optionally substituted aryl, optionally substituted heteroaryl, optionally substituted aryl (lower alkyl), halogen, —$OR^9$, —$NR^9$(carboxy(lower alkyl)), —C(=O)$OR^9$, —C(=O)$NR^9R^{10}$, —$SO_2NR^9R^{10}$, or —$NR^9C(=O)R^{10}$, where $R^9$ and $R^{10}$ are independently, hydrogen, optionally substituted lower alkyl, lower alkyl-N ($C_{1-2}$ alkyl)$_2$, lower alkyl(optionally substituted heterocycloalkyl), optionally substituted cycloalkyl, cycloalkyl (lower alkyl), optionally substituted aryl, optionally substituted aryloxy, heteroaryl, heteroaryl(lower alkyl), or $R^9$ and $R^{10}$ together are —(CH$_2$)$_{4-6}$— optionally interrupted by one O, S, NH, N-(aryl), N-(aryl(lower alkyl)), N-(carboxy(lower alkyl)) or N-(optionally substituted $C_{1-2}$ alkyl) group.

7. The compound of claim 6, where $R^2$ is optionally substituted lower alkyl, cycloalkyl, optionally substituted heterocycloalkyl, optionally substituted aryl, optionally substituted heteroaryl, optionally substituted aryl(lower alkyl), halogen, —$OR^9$, —$NR^9$(carboxy(lower alkyl)), —C(=O) $OR^9$, —C(=O)$NR^9R^{10}$, —$SO_2NR^9R^{10}$, or —$NR^9C(=O) R^{10}$, where $R^9$ and $R^{10}$ are independently, hydrogen, optionally substituted lower alkyl, lower alkyl-N($C_{1-2}$ alkyl)$_2$, lower alkyl(optionally substituted heterocycloalkyl), optionally substituted cycloalkyl, cycloalkyl(lower alkyl), optionally substituted aryl, optionally substituted aryloxy, heteroaryl, heteroaryl(lower alkyl), or $R^9$ and $R^{10}$ together are —(CH$_2$)$_{4-6}$— optionally interrupted by one O, S, NH, N-(aryl), N-(aryl(lower alkyl)), N-(carboxy(lower alkyl)) or N-(optionally substituted $C_{1-2}$ alkyl) group.

8. The compound of claim 1, where $R^3$ is hydrogen, optionally substituted lower alkyl, optionally substituted heterocycloalkyl, optionally substituted aryl, optionally substituted heteroaryl, optionally substituted aryl(lower alkyl), halo(lower alkyl), halogen, —$OR^9$, —$NR^9R^{10}$, —$C(=O)OR^9$, or —$C(=O)NR^9R^{10}$, where $R^9$ and $R^{10}$ are independently, hydrogen, optionally substituted lower alkyl, lower alkyl-N($C_{1-2}$ alkyl)$_2$, lower alkyl(optionally substituted heterocycloalkyl), optionally substituted cycloalkyl, cycloalkyl(lower alkyl), optionally substituted aryl, optionally substituted aryloxy, heteroaryl, heteroaryl(lower alkyl), or $R^9$ and $R^{10}$ together are —$(CH_2)_{4-6}$— optionally interrupted by one O, S, NH, N-(aryl), N-(aryl(lower alkyl)), N-(carboxy(lower alkyl)) or N-(optionally substituted $C_{1-2}$ alkyl) group.

9. The compound of claim 8, where $R^3$ is optionally substituted lower alkyl, optionally substituted heterocycloalkyl, optionally substituted aryl, optionally substituted heteroaryl, optionally substituted aryl(lower alkyl), halo(lower alkyl), halogen, —$OR^9$, —$NR^9R^{10}$, —$C(=O)OR^9$, or —$C(=O)NR^9R^{10}$, where $R^9$ and $R^{10}$ are independently, hydrogen, optionally substituted lower alkyl, lower alkyl-N($C_{1-2}$ alkyl)$_2$, lower alkyl(optionally substituted heterocycloalkyl), optionally substituted cycloalkyl, cycloalkyl(lower alkyl), optionally substituted aryl, optionally substituted aryloxy, heteroaryl, heteroaryl(lower alkyl), or $R^9$ and $R^{10}$ together are —$(CH_2)_{4-6}$— optionally interrupted by one O, S, NH, N-(aryl), N-(aryl(lower alkyl)), N-(carboxy(lower alkyl)) or N-(optionally substituted $C_{1-2}$ alkyl) group.

10. The compound of claim 1, where $R^6$ is hydrogen, optionally substituted lower alkyl, alkenyl, cycloalkyl, cycloalkyl(lower alkyl), optionally substituted heterocycloalkyl, optionally substituted aryl, optionally substituted aryl(lower alkyl), optionally substituted heteroaryl, optionally substituted heteroaryl(lower alkyl), —$C(=O)R^{11}$, —$C(=O)OR^{11}$, —$C(=O)NR^{11}R^{12}$, —$SO_2R^{11}$, or —$SO_2NR^{11}R^{12}$, where $R^{11}$ and $R^{12}$ are independently, hydrogen, optionally substituted lower alkyl, cycloalkyl, cycloalkyl(lower alkyl), aryl heteroaryl, heteroaryl(lower alkyl), or $R^{11}$ and $R^{12}$ together are —$(CH_2)_{4-6}$—.

11. The compound of claim 1 that is a compound of formula Aa or formula Ba:

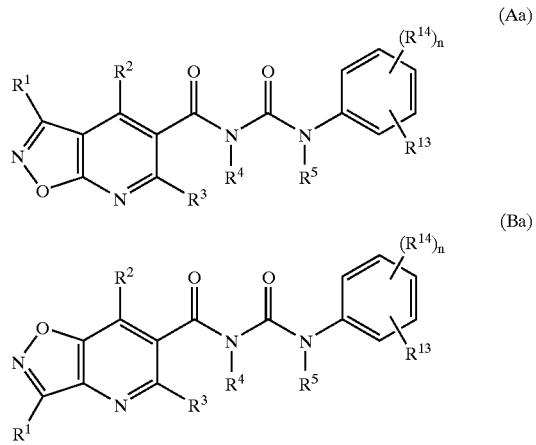

where:
$R^1$, $R^2$, $R^3$, $R^4$, and $R^5$ are as defined in claim 1, $R^{13}$ is hydrogen, optionally substituted lower alkyl, alkenyl, alkynyl, cycloalkyl, cycloalkyl(lower alkyl), heterocycloalkyl, optionally substituted aryl, optionally substituted aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, —$NR^{15}R^{16}$, —$C(=O)R^{15}$, —$C(=O)OR^{15}$, —$C(=O)NR^{15}R^{16}$, —$OC(=O)R^{15}$, —$SO_2R^{15}$, —$SO_2NR^{15}R^{16}$, —$NR^{15}SO_2R^{16}$ or —$NR^{15}C(=O)R^{16}$, where $R^{15}$ and $R^{16}$ are independently, hydrogen, optionally substituted lower alkyl, alkenyl, alkynyl, —$CF_3$, cycloalkyl, optionally substituted heterocycloalkyl, cycloalkyl(lower alkyl), optionally substituted aryl, optionally substituted aryloxy, optionally substituted heteroaryl, optionally substituted heteroaryl(lower alkyl), or, together, are —$(CH_2)_{4-6}$— optionally interrupted by one O, S, NH or N—($C_{1-2}$ alkyl) group, each $R^{14}$ is independently selected from optionally substituted lower alkyl, optionally substituted aryl, optionally substituted heteroaryl, hydroxy, halogen, —$CF_3$, —$OR^{17}$, —$NR^{17}R^{18}$, —$C(=O)R^{18}$, —$C(=O)OR^{18}$, —$C(=O)NR^{17}R^{18}$, where $R^{17}$ and $R^{18}$ are independently, hydrogen, lower alkyl, alkenyl, alkynyl, —$CF_3$, optionally substituted heterocycloalkyl, cycloalkyl, cycloalkyl(lower alkyl), optionally substituted aryl, optionally substituted aryloxy, heteroaryl, heteroaryl (lower alkyl), or, together, are —$(CH_2)_{4-6}$—, optionally interrupted by one O, S, NH or N—($C_{1-2}$ alkyl) group, and where n is an integer of 0 to 4, or a pharmaceutically acceptable salt thereof, optionally in the form of a single stereoisomer or mixture of stereoisomers.

12. The compound of claim 11, where said compound is a compound of Formula Aa or a pharmaceutically acceptable salt thereof, optionally in the form of a single stereoisomer or mixture of stereoisomers.

13. The compound of claim 11, where said compound is a compound of Formula Ba or a pharmaceutically acceptable salt thereof, optionally in the form of a single stereoisomer or mixture of stereoisomers.

14. The compound of claim 11, where $R^{13}$ is —$OR^{15}$, and $R^{15}$ is hydrogen, lower alkyl optionally substituted with —$C(=O)OR^{19}$, where $R^{19}$ is hydrogen or lower alkyl, alkenyl, alkynyl, —$CF_3$, cycloalkyl, optionally substituted heterocycloalkyl, cycloalkyl(lower alkyl), optionally substituted aryl, optionally substituted heteroaryl, or optionally substituted heteroaryl(lower alkyl).

15. The compound of claim 11, where $R^{13}$ is hydrogen, optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, —$NR^{15}R^{16}$, —$C(=O)R^{15}$, —$C(=O)OR^{15}$, —$C(=O)NR^{15}R^{16}$, —$OC(=O)R^{15}$, —$SO_2R^{15}$, —$SO_2NR^{15}R^{16}$, or —$NR^{15}C(=O)R^{16}$, where $R^{15}$ and $R^{16}$ are independently, hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl(lower alkyl) or, together, are —$(CH_2)_{4-6}$— optionally interrupted by one O, S, NH or N—($C_{1-2}$ alkyl) group.

16. The compound of claim 15, where $R^{13}$ is optionally substituted lower alkyl, alkenyl, heterocycloalkyl, optionally substituted aryl, optionally substituted aryl(lower alkyl), optionally substituted heteroaryl, optionally substituted heteroaryl(lower alkyl), halo(lower alkyl), —$CF_3$, halogen, nitro, —CN, —$OR^{15}$, —$SR^{15}$, —$NR^{15}R^{16}$, —C(=O)$R^{15}$, —C(=O)$OR^{15}$, —C(=O)$NR^{15}R^{16}$, —OC(=O)$R^{15}$, —$SO_2R^{15}$, —$SO_2NR^{15}R^{16}$, or —$NR^{15}$C(=O)$R^{16}$, where $R^{15}$ and $R^{16}$ are independently, hydrogen, optionally substituted lower alkyl, alkenyl, cycloalkyl, optionally substituted heterocycloalkyl, cycloalkyl(lower alkyl), optionally substituted aryl, optionally substituted heteroaryl, optionally substituted heteroaryl(lower alkyl) or, together, are —$(CH_2)_{4-6}$— optionally interrupted by one O, S, NH or N—($C_{1-2}$ alkyl) group.

17. The compound of claim 11, where $R^{14}$ is independently selected from optionally substituted lower alkyl, optionally substituted aryl, optionally substituted heteroaryl, hydroxy, halogen, —$CF_3$, —$OR^{17}$ —$NR^{17}R^{18}$, —C(=O)$R^{18}$, —C(=O)$OR^{18}$, —C(=O)$NR^{17}R^{18}$, where $R^{17}$ and $R^{18}$ are, independently, hydrogen, lower alkyl, alkenyl, or optionally substituted aryl.

18. The compound of claim 16, where n is an integer of 1 to 2.

19. The compound of claim 18, where n is 1.

20. The compound of claim 11, where $R^1$ is lower alkyl.

21. The compound of claim 11, where $R^2$ and $R^3$ are independently selected from hydrogen, lower alkyl, halogen, $OR^9$, —$NR^9R^{10}$, where $R^9$ and $R^{10}$ are independently lower alkyl, substituted lower alkyl, or substituted aryl, or $R^9$ and $R^{10}$ together are —$(CH_2)_{4-6}$— optionally interrupted by one O, S, NH, N-(aryl), N-(aryl(lower alkyl)), N-(carboxy(lower alkyl)) or N-(optionally substituted $C_{1-2}$ alkyl) group.

22. The compound of claim 16, where $R^{13}$ is independently selected from halogen, optionally substituted aryl, —$CF_3$, —$CH_3$, —CN, —$OR^{15}$, —C(=O)$R^{15}$, —C(=O)$OR^{15}$, —C(=O)$NR^{15}R^{16}$, or —$CO_2H$.

23. The compound of claim 11, where $R^{14}$ is independently selected from halogen, optionally substituted lower alkyl, —$CF_3$, —$OR^{17}$, aryl, heteroaryl, —$NR^{17}R^{18}$, —C(=O)$R^{17}$, —C(=O)$OR^{17}$, —C(=O)$NR^{17}R^{18}$, or —$CO_2H$, where $R^{17}$ and $R^{18}$ are, independently, lower alkyl, substituted lower alkyl, or substituted aryl, or, together, are —$(CH_2)_{4-6}$— optionally interrupted by one O, S, NH or N—($C_{1-2}$ alkyl) group.

24. The compound of claim 11, where $R^3$ is 4-methylpiperazinyl, $R^{13}$ is 3-$CF_3$, and $R^{14}$ is 4-F.

25. A pharmaceutical composition comprising:
(a) a therapeutically effective amount of a compound of claim 1; and
(b) a pharmaceutically acceptable excipient.

26. A method of treating an allergic, inflammatory, or autoimmune disorder or disease selected from the group consisting of asthma, atherosclerosis, glomerulonephritis, pancreatitis, restenosis, rheumatoid arthritis, diabetic nephropathy, pulmonary fibrosis, inflammatory bowel disease, Crohn's disease, transplant rejection, and multiple sclerosis, comprising administering a therapeutically effective dose of at least one compound of claim 1 to a mammal in need of such treatment.

* * * * *